(12) United States Patent
Zhou et al.

(10) Patent No.: US 12,176,068 B2
(45) Date of Patent: Dec. 24, 2024

(54) METHODS FOR PREDICTING GENOMIC VARIATION EFFECTS ON GENE TRANSCRIPTION

(71) Applicants: The Trustees of Princeton University, Princeton, NJ (US); The Simons Foundation, Inc., New York, NY (US)

(72) Inventors: Jian Zhou, Dallas, TX (US); Chandra Theesfeld, Princeton, NJ (US); Olga G. Troyanskaya, Princeton, NJ (US)

(73) Assignees: The Trustees of Princeton University, Princeton, NJ (US); The Simons Foundation, Inc., New York, NY (US)

( * ) Notice: Subject to any disclaimer, the term of this patent is extended or adjusted under 35 U.S.C. 154(b) by 1058 days.

(21) Appl. No.: 17/041,836

(22) PCT Filed: Mar. 26, 2019

(86) PCT No.: PCT/US2019/024108
§ 371 (c)(1),
(2) Date: Sep. 25, 2020

(87) PCT Pub. No.: WO2019/191123
PCT Pub. Date: Oct. 3, 2019

(65) Prior Publication Data
US 2021/0027855 A1    Jan. 28, 2021

Related U.S. Application Data

(60) Provisional application No. 62/648,355, filed on Mar. 26, 2018.

(51) Int. Cl.
*G16B 20/20*    (2019.01)
*G16B 20/50*    (2019.01)
*G16B 25/10*    (2019.01)

(52) U.S. Cl.
CPC ............. *G16B 20/20* (2019.02); *G16B 20/50* (2019.02); *G16B 25/10* (2019.02)

(58) Field of Classification Search
None
See application file for complete search history.

(56) References Cited

U.S. PATENT DOCUMENTS

2014/0193821 A1    7/2014    Sanford et al.
2016/0357903 A1    12/2016    Shendure et al.
(Continued)

FOREIGN PATENT DOCUMENTS

WO    WO-2016182893 A1 * 11/2016 ........... C12N 15/102
WO    2017033154 A1    3/2017
(Continued)

OTHER PUBLICATIONS

Singh, Ritambhara, et al. "DeepChrome: deep-learning for predicting gene expression from histone modifications." Bioinformatics 32.17 (2016): 1639-i648. (Year: 2016).*
(Continued)

*Primary Examiner* — Olivia M. Wise
*Assistant Examiner* — Mary C Leverett
(74) *Attorney, Agent, or Firm* — KPPB LLP

(57) ABSTRACT

Processes to determine the effect of genetic sequence on gene expression levels are described. Generally, models are used to determine spatial chromatin profile from genetic sequence, which can be used in several downstream applications. The effect of the spatial chromatin profile on gene expression is also determined in some instances. Various methods further develop research tools, perform diagnostics, and treat individuals based on sequence effects on gene expression levels.

17 Claims, 37 Drawing Sheets

Specification includes a Sequence Listing.

(56) References Cited

U.S. PATENT DOCUMENTS

| | | | |
|---|---|---|---|
| 2016/0364522 A1 | 12/2016 | Frey et al. | |
| 2017/0175189 A1 | 6/2017 | Hensel | |
| 2021/0074378 A1 | 3/2021 | Zhou et al. | |

FOREIGN PATENT DOCUMENTS

| | | |
|---|---|---|
| WO | 2019148141 A1 | 8/2019 |
| WO | 2019191123 A1 | 10/2019 |

OTHER PUBLICATIONS

Lo, Albert, and Lei Qi. "Genetic and epigenetic control of gene expression by CRISPR-Cas systems." F1000Research 6 (2017). (Year: 2017).*

Zhou, Jian, and Olga G. Troyanskaya. "Predicting effects of noncoding variants with deep learning-based sequence model." Nature methods 12.10 (2015): 931-934. (Year: 2015).*

Khan, Javed, et al. "Classification and diagnostic prediction of cancers using gene expression profiling and artificial neural networks." Nature medicine 7.6 (2001): 673-679. (Year: 2001).*

Lieb, Jason D., et al. "Applying whole-genome studies of epigenetic regulation to study human disease." Cytogenetic and genome research 114.1 (2006): 1-15. (Year: 2006).*

Roadmap Epigenomics Consortium Integrative analysis coordination, Kundaje Anshul et al. "Integrative analysis of 111 reference human epigenomes." Nature 518.7539 (2015): 317-330. (Year: 2015).*

Kelley, David R., Jasper Snoek, and John L. Rinn. "Basset: learning the regulatory code of the accessible genome with deep convolutional neural networks." Genome research 26.7 (2016): 990-999. (Year: 2016).*

Alzubaidi, Laith, et al. "Review of deep learning: concepts, CNN architectures, challenges, applications, future directions." Journal of big Data 8 (2021): 1-74. (Year: 2021).*

Angermueller, Christof, et al. "DeepCpG: accurate prediction of single-cell DNA methylation states using deep learning [Erratum: Dec. 2017, v. 18 (1); p. 90]." (2017). (Year: 2017).*

Vadapalli, Sreya, et al. "Artificial intelligence and machine learning approaches using gene expression and variant data for personalized medicine." Briefings in bioinformatics 23.5 (2022): bbac191. (Year: 2022).*

Osisanwo, F. Y., et al. "Supervised machine learning algorithms: classification and comparison." International Journal of Computer Trends and Technology (IJCTT) 48.3 (2017): 128-138. (Year: 2017).*

Pirooznia, Mehdi, et al. "A comparative study of different machine learning methods on microarray gene expression data." BMC genomics 9 (2008): 1-13. (Year: 2007).*

International Preliminary Report on Patentability for International Application No. PCT/US2019/015484, Report issued Jul. 28, 2020, Mailed Aug. 6, 2020, 10 Pgs.

International Preliminary Report on Patentability for International Application No. PCT/US2019/024108, Issued on Sep. 29, 2020, Mailed on Oct. 8, 2020, 9 Pgs.

International Search Report and Written Opinion for International Application No. PCT/US2019/015484, Search completed May 1, 2019, Mailed Jun. 19, 2019, 18 Pgs.

International Search Report and Written Opinion for International Application No. PCT/US2019/024108, Search completed Jul. 17, 2019, Mailed Aug. 12, 2019, 15 Pgs.

1000 Genomes Project Consortium, "A global reference for human genetic variation", Nature, vol. 526, Oct. 2015, pp. 68-74, doi:10.1038/nature15393.

Abrahams et al., "SFARI Gene 2.0: a community-driven knowledgebase for the autism spectrum disorders (ASDs)", Molecular Autism, vol. 4, No. 36, Oct. 3, 2013, 3 pgs.

Aguet et al., "Local genetic effects on gene expression across 44 human tissues", bioRxiv, Retrieved from: https://www.biorxiv.org/content/10.1101/074450v1, Sep. 9, 2016, 24 pgs.

Alipanahi et al., "Predicting the sequence specificities of DNA- and RNA-binding proteins by deep learning", Nature Biotechnology, Aug. 2015, vol. 33, No. 8, pp. 831-839, published online Jul. 27, 2015, doi:10.1038/nbt.3300.

Anney et al., "Individual common variants exert weak effects on the risk for autism spectrum disorders", Human Molecular Genetics, vol. 21, No. 21, Jul. 26, 2012, pp. 4781-4792, Advanced Access published Jul. 26, 2012, doi: 10.1093/hmg/dds301.

Autism Spectrum Disorders, Working Group, "Meta-analysis of GWAS of over 16,000 individuals with autism spectrum disorder highlights a novel locus at 10q24.32 and a significant overlap with schizophrenia", Molecular Autism, May 22, 2017, vol. 8, No. 21, 17 pgs., DOI: 10.1186/s13229-017-0137-9.

Bailey et al., "MEME Suite: tools for motif discovery and searching", Nucleic Acids Research, 2009, vol. 37, No. 2, pp. W202-W208, Web Server Issue, published online May 20, 2009, coi:10.1093/nar/gkp335.

Barash et al., "Deciphering the splicing code", Nature, vol. 465, May 6, 2010, pp. 53-59, doi:10.1038/nature09000.

Barger et al., "Prevalence and Onset of Regression within Autism Spectrum Disorders: A Meta-analytic Review", Journal of Autism and Developmental Disorders, 2013, vol. 43, pp. 817-828, published online Aug. 2, 2012, DOI: 10.1007/d10803-012-1621-x.

Beer et al., "Predicting Gene Expression from Sequence", Cell, Apr. 16, 2004, vol. 117, No. 2, pp. 185-198.

Bentham et al., "Genetic association analyses implicate aberrant regulation of innate and adaptive immunity genes in the pathogenesis of systemic lupus erythematosus", Nature Genetics, Dec. 2015, vol. 47, No. 12, pp. 1457-1464, available in PMC May 18, 2016, doi:10.1038/ng.3434.

Berkovits et al., "Alternative 3' UTRs act as scaffolds to regulate membrane protein localization", Nature, vol. 522, Apr. 20, 2015, pp. 363-367, doi:10.1038/nature14321.

Bernier et al., "Haploinsufficiency of SF3B4, a Component of the Pre-mRNA Spliceosomal Complex, Causes Nager Syndrome", The American Journal of Human Genetics, May 4, 2012, vol. 90, No. 5, pp. 925-933, DOI 10.1016/j.ajhg.2012.04.004.

Bernstein et al., "The NIH Roadmap Epigenomics Mapping Consortium", Nature Biotechnology, vol. 28, Oct. 13, 2010, pp. 1045-1048, doi:10.1038/nbt1010-1045.

Bertrand et al., "Proneural Genes and the Specification of Neural Cell Types", Nature Reviews Neuroscience, vol. 3, Jul. 2002, pp. 517-530.

Black, "Mechanisms of Alternative Pre-Messenger RNA Splicing", Annual Review of Biochemistry, 2003, vol. 72, pp. 291-336, first published online as a Review in Advance on Feb. 27, 2003, doi:10.1146/annurev.biochem.72.121801.161720.

Buhlmann, "Boosting for high-dimensional linear models", Annals of Statistics, vol. 34, No. 2, 2006, pp. 559-583, DOI: 10.1214/009053606000000092.

Bussemaker et al., "Regulatory element detection using correlation with expression", Nature Genetics, vol. 27, Feb. 2001, pp. 167-171.

Chen et al., "XGBoost: A Scalable Tree Boosting System", Proceedings of the 22nd ACM SIGKDD International Conference on Knowledge Discovery and Data Mining, Aug. 2016, pp. 785-794, DOI: http://dx.doi.org/10.1145/2939672.2939785.

Chu et al., "A genome-wide association study identifies two new risk loci for Graves' disease", Nature Genetics, Sep. 2011, vol. 43, No. 9, pp. 897-901, published online Aug. 14, 2011, doi:10.1038/ng.898.

Cooper et al., "A Copy Number Variation Morbidity Map of Developmental Delay", Nature Genetics, vol. 43, Aug. 14, 2011, pp. 838-846, doi:10.1038/ng.909.

Costa-Mattioli et al., "Translational Control of Long-Lasting Synaptic Plasticity and Memory", Neuron, vol. 61, Jan. 15, 2009, pp. 10-26, DOI 10.1016/j.neuron.2008.10.055.

Crosnier et al., "Organizing cell renewal in the intestine: stem cells, signals and combinatorial control", Nature Reviews Genetics, vol. 7, May 2006, pp. 349-359, doi:10.1038/nrg1840.

(56) References Cited

OTHER PUBLICATIONS

Cross-Disorder Group of the Psychiatric Genomics Consortium, "Identification of risk loci with shared effects on five major psychiatric disorders: a genome-wide analysis", Lancet, Apr. 20, 2013, vol. 381, No. 9875, pp. 1371-1379, published online Feb. 28, 2013, http://dx.doi.org/10.1016/S0140-6736(12)62129-1.
Darnell, "RNA Protein Interaction in Neurons", Annual Review of Neuroscience, Jul. 8, 2013, vol. 36, pp. 243-270, doi:10.1146/annurev-neuro-062912-114322.
Darnell et al., "FMRP Stalls Ribosomal Translocation on mRNAs Linked to Synaptic Function and Autism", Cell, Jul. 22, 2011, vol. 146, No. 2, pp. 247-261, DOI 10.1016/j.cell.2011.06.013.
De La Torre-Ubieta et al., "Advancing the understanding of autism disease mechanisms through genetics", Nature Medicine, Apr. 2016, vol. 22, pp. 345-361, published online Apr. 6, 2016; doi:10.1038/nm.4071.
De Rubeis et al., "Synaptic, transcriptional and chromatin genes disrupted in autism", Nature, Nov. 13, 2014, vol. 515. No. 7526, pp. 209-215, epublished Oct. 28, 2014, doi: 10.1038/nature13772.
De Souza, "The ENCODE project", Nature Methods, Nov. 6, 2012, vol. 9, No. 11, pp. 1046.
Dobin et al., "STAR: ultrafast universal RNA-seq aligner", Bioinformatics, Jan. 1, 2013, vol. 29, No. 1, pp. 15-21, Advance Access publication Oct. 25, 2012, doi:10.109./bioinformatics/bts635.
Dong et al., "De Novo Insertions and Deletions of Predominantly Paternal Origin Are Associated with Autism Spectrum Disorder", Cell Reports, Oct. 9, 2014, vol. 9, pp. 16-23, DOI: https://doi.org/10.1016/j.celrep.2014.08.068.
Eckler et al., "Fez family transcription factors: Control of neurogenesis and cell fate in the developing mammalian nervous system", BioEssays, Aug. 2014, vol. 36, No. 8, pp. 788-797, doi:10.1002/bies.201400039.
Edwards et al., "Beyond GWASs: Illuminating the Dark Road from Association to Function", The American Journal of Human Genetics, vol. 93, Nov. 7, 2013, pp. 779-797, http://dx.doi.org/10.1016/j.ajhg.2013.10.012.
Efron, "Size, Power and False Discovery Rates", The Annals of Statistics, vol. 35, No. 4, Aug. 2007, pp. 1351-1377, DOI: 10.1214/009053606000001460.
Fairfax et al., "Genetics of gene expression in primary immune cells identifies cell type-specific master regulators and roles of HLA alleles", Nature Genetics, vol. 44, Mar. 25, 2012, pp. 502-510, https://doi.org/10.1038/ng.2205.
Feigin et al., "Recurrent noncoding regulatory mutations in pancreatic ductal adenocarcinoma", Nature Genetics, vol. 49, Advanced online publication: May 8, 2017, 11 pgs., doi.org/10.1038/ng.3861.
Fromer et al., "De novo mutations in schizophrenia implicate synaptic networks", Nature, published online Jan. 22, 2014, 6 pgs., doi:10.1038/nature12929.
Gamazon et al., "A gene-based association method for mapping traits using reference transcriptome data", Nature Genetics, Sep. 2015, vol. 47, vol. 9, pp. 1091-1098, published online Aug. 10, 2015, doi:10.1038/ng.3367.
Gao et al., "An AUTS2-Polycomb complex activates gene expression in the CNS", Nature, Dec. 17, 2014, vol. 516, pp. 349-354, doi:10.1038/nature13921.
Geifman et al., "The Neural/Immune Gene Ontology: clipping the Gene Ontology for neurological and immunological systems", BMC Bioinformatics, vol. 11, No. 458, Sep. 12, 2010, 14 pgs.
Gene Ontology Consortium, "Gene Ontology Consortium: going forward", Nucleic Acids Research, 2015, vol. 43, Database Issue, pp. D1049-D1056, published online Nov. 26, 2014. doi: 10.1093/nar/gku1179.
Gonzalez-Porta et al., "Transcriptome analysis of human tissues and cell lines reveals one dominant transcript per gene", Genome Biology, vol. 14, No. R70, Jul. 1, 2013, 11 pgs., doi:10.1186/GB-2013-14-7-r70.
Graham et al., "Genetic variants near TNFAIP3 on 6q23 are associated with systemic lupus erythematosus", Nature Genetics, Sep. 2008, vol. 40, pp. 1059-1061, published online Aug. 1, 2008, https://doi.org/10.1038/ng.200.
Greene et al., "Understanding multicellular function and disease with human tissue-specific networks", Nature Genetics, Apr. 27, 2015, vol. 47, pp. 569-576, doi:10.1038/ng.3259.
GTEX Consortium, "Genetic effects on gene expression across human tissues", Nature, vol. 550, Oct. 12, 2017, pp. 204-213, doi:10.1038/nature24277.
Guhaniyogi et al., "Regulation of mRNA stability in mammalian cells", Gene, vol. 265, No. 1-2, Mar. 7, 2001, pp. 11-23.
Haerty et al., "No Gene in the Genome Makes Sense Except in the Light of Evolution", Annual Review of Genomics and Human Genetics, Aug. 2014, vol. 15, pp. 71-92, first published online as a Review in Advance on Apr. 24, 2014, doi:.10.1146/annurev-genom-090413-025621.
Halbritter, "Genome-scale transcriptomic and epigenomic analysis of stem cells", Doctoral Thesis, The University of Edinburgh, 2012, [online]. [Retrieved on Jul. 16, 2019], 255 pgs. (presented in three parts).
Harrow et al., "GENCODE: The reference human genome annotation for The ENCODE Project", Genome Research, vol. 22, No. 9, Sep. 2012, pp. 1760-1774, http://www.genome.org/cgi/doi/10.1101/gr.135350.111.
Hormozdiari et al., "The discovery of integrated gene networks for autism and related disorders", Genome Research, vol. 25, Nov. 5, 2014, pp. 142-154, http://www.genome.org/cgi/doi/10.1101/gr.178855.114.
Iossifov et al., "De Novo Gene Disruptions in Children on the Autistic Spectrum", Neuron, vol. 74, Apr. 26, 2012, pp. 285-299, DOI 10.1016/j.neuron.2012.04.009.
Iossifov et al., "Low load for disruptive mutations in autism genes and their biased transmission", Proceedings of the National Academy of Sciences, vol. 112, No. 41, Oct. 13, 2015, pp. E5600-E5607.
Iossifov et al., "The contribution of de novo coding mutations to autism spectrum disorder", Nature, vol. 515, Oct. 29, 2014, pp. 216-221, doi:10.1038/nature13908.
Jacquemont et al., "A Higher Mutational Burden in Females Supports a "Female Protective Model" in Neurodevelopmental Disorders", The American Journal of Human Genetics, vol. 94, Mar. 6, 2014, pp. 415-425, http://dx.doi.org/10.1016/j.ajhg.2014.02.001.
Jaffe et al., "Developmental and genetic regulation of the human cortex transcriptome in schizophrenia", bioRxiv, Nov. 22, 2017, Retrieved from: https://www.biorxiv.org/content/10.1101/124321v2, 34 pgs.
Jaffe et al., "Developmental regulation of human cortex transcription and its clinical relevance at single base resolution", Nature Neuroscience, Jan. 2015, vol. 18, pp. 154-161, published online Dec. 15, 2014, doi:10.1038/nn.3898.
Jeste et al., "Disentangling the heterogeneity of autism spectrum disorder through genetic findings", Nature Reviews Neurology, Feb. 2014, vol. 10, published online Jan. 28, 2014, pp. 74-81, doi:10.1038/nrneurol.2013.278.
Jiang et al., "Detection of Clinically Relevant Genetic Variants in Autism Spectrum Disorder by Whole-Genome Sequencing", The American Journal of Human Genetics, vol. 93, No. 2, Aug. 8, 2013, pp. 249-263, http://dx.doi.org/10.1016/j.ajhg.2013.06.012.
Khurana et al., "Role of non-coding sequence variants in cancer", Nature Reviews Genetics, Feb. 2016, vol. 17, No. 2, pp. 93-108, published online Jan. 19, 2016, doi:10.1038/nrg2015.17.
King et al., "Topoisomerases facilitate transcription of long genes linked to autism", Nature, vol. 501, pp. 58-62, Aug. 28, 2013, doi:10.1038/nature12504.
Kircher et al., "A general framework for estimating the relative pathogenicity of human genetic variants", Nature Genetics, Mar. 2014, vol. 46, No. 3, pp. 310-315, published online Feb. 2, 2014, doi:10.1038/ng.2892.
Kong et al., "Rate of de novo mutations and the importance of father's age to disease risk", Nature, Aug. 23, 2012, vol. 488, pp. 471-475, doi:10.1038/nature11396.

(56) References Cited

OTHER PUBLICATIONS

Kraemer et al., "Loss of murine TDP-43 disrupts motor function and plays an essential role in embryogenesis", Acta Neuropathologica, Mar. 3, 2010, vol. 119, No. 4, pp. 409-419. doi:10.1007/s00401-010-0659-0.

Kreimer et al., "Predicting gene expression in massively parallel reporter assays: A comparative study", Human Mutation, vol. 38, No. 9, Feb. 21, 2017, pp. 1240-1250, DOI: 10.1002/humu.23197.

Krichevsky et al., "Neuronal RNA Granules: A Link between RNA Localization and Stimulation-Dependent Translation", Neuron, vol. 32, Nov. 20, 2001, pp. 683-696.

Krishnan et al., "Genome-wide prediction and functional characterization of the genetic basis of autism spectrum disorder", Nature Neuroscience, vol. 19, Aug. 1, 2016, pp. 1454-1462, doi:10.1038/nn.4353.

Krizhevsky et al., "ImageNet Classification with Deep Convolutional Neural Networks", Advances in Neural Information Processing Systems (NIPS 2012), vol. 25, 2012, pp. 1097-1105.

Kumari et al., "Polycomb group complexes are recruited to reactivated FMR1 alleles in Fragile X syndrome in response to FMR1 transcription", Human Molecular Genetics, vol. 23, No. 24, Dec. 15, 2014, pp. 6575-6583, doi: 10.1093/hmg/ddu378.

Lee et al., "Two new susceptibility loci for Kawasaki disease identified through genome-wide association analysis", Nature Genetics, May 2012, vol. 44, pp. 522-525, Mar. 25, 2012, doi:10.1038/ng.2227.

Lek et al., "Analysis of protein-coding genetic variation in 60,706 humans", Nature, vol. 536, Aug. 17, 2016, pp. 285-291, doi:10.1038/nature19057.

Levy et al., "Rare De Novo and Transmitted Copy-Number Variation in Autistic Spectrum Disorders", Neuron, vol. 70, No. 5, Jun. 9, 2011, pp. 886-897, DOI 10.1016/j.neuron.2011.05.015.

Li et al., "Exploring the Function of Genetic Variants in the Non-Coding Genomic Regions: Approaches for Identifying Human Regulatory Variants Affecting Gene Expression", Briefings in Bioinformatics, May 2015, vol. 16, No. 3, pp. 393-412, Advanced Access publication Jun. 10, 2014, doi:10.1093fbib/bbu018.

Li et al., "RSEM: accurate transcript quantification from RNA-Seq data with or without a reference genome", BMC Bioinformatics, vol. 12, No. 323, Aug. 4, 2011, 16 pgs., http:/www.biomedcentral.com/1471-2105/12/323.

Li et al., "The impact of rare variation on gene expression across tissues", Nature, vol. 550, Oct. 12, 2017, pp. 239-243, doi:10.1038/nature24267.

Licatalosi et al., "RNA processing and its regulation: global insights into biological networks", Nature Reviews Genetics, vol. 11, Jan. 2010, pp. 75-87, doi:10.1038/nrg2673.

Lines et al., "Haploinsufficiency of a Spliceosomal GTPase Encoded by EFTUD2 Causes Mandibulofacial Dysostosis with Microcephaly", The American Journal of Human Genetics, vol. 90, Feb. 10, 2012, pp. 369-377, DOI 10.1016/j.ajhg.2011.12.023.

Liu et al., "A gradient-boosting approach for filtering de novo mutations in parent-offspring trios", Bioinformatics, 2014, vol. 30, No. 13, pp. 1830-1836, Advance Access publication Mar. 10, 2014, doi:10.1093/bioinformatics/btu141.

Lu et al., "Support for calcium channel gene defects in autism spectrum disorders", Molecular Autism, Dec. 15, 2012, vol. 3, No. 18, 9 pgs., https://doi.org/10.1186/2040-2392-3-18.

MacArthur et al., "The new NHGRI-EBI Catalog of published genome-wide association studies (GWAS Catalog)", Nucleic Acids Research, 2017, vol. 45, Database Issue, pp. D896-D901, published online Nov. 28, 2016, doi: 10.1093/nar/gkw1133.

Martin et al., "Cytogenetic and Molecular Characterization of A2BP1/FOX1 as a Candidate Gene for Autism", American Journal of Medical Genetics Part B (Neuropsychiatric Genetics), vol. 144B, Oct. 5, 2007, pp. 869-876, DOI 10.1002/ajmg.b.30530.

McCullough et al., "G Triplets Located throughout a Class of Small Vertebrate Introns Enforce Intron Borders and Regulate Splice Site Selection", Molecular and Cell Biology, vol. 17, No. 8, Aug. 1997, pp. 4562-4571.

McKenna et al., "The Genome Analysis Toolkit: A MapReduce framework for analyzing next-generation DNA sequencing data", Genome Research, vol. 20, Jul. 12, 2010, pp. 1297-1303, http://www.genome.org/cgi/doi/10.1101/gr.107524.110.

Mercer et al., "Genome-wide discovery of human splicing branchpoints", Genome Research, vol. 25, No. 2, Feb. 2015, pp. 290-303, http://www.genome.org/cgi/doi/10.1101/gr.182899.114.

Mi et al., "Large-scale gene function analysis with the PANTHER classification system", Nature Protocols, vol. 8, 2013, pp. 1551-1566, published online Jul. 18, 2013, doi:10.1038/nprot.2013.092.

Mi et al., "PANTHER version 11: expanded annotation data from Gene Ontology and Reactome pathways, and data analysis tool enhancements", Nucleic Acids Research, 2017, vol. 45, Database issue, pp. D183-D189, published online Nov. 28, 2016, doi: 10.1093/nar/ghk1138.

Michaelson et al., "Whole-Genome Sequencing in Autism Identifies Hot Spots for De Novo Germline Mutation", Cell, Dec. 21, 2012, vol. 151, No. 7, pp. 1431-1442, http://dx.doi.org/10.1016/j.cell.2012.11.019.

Moore et al., "Mapping Argonaute and conventional RNA-binding protein interactions with RNA at single-nucleotide resolution using HITS-CLIP and CIMS analysis", Nature Protocols, Jan. 9, 2014, vol. 9, No. 2, pp. 263-293, doi:10.1038/nprot.2014.012.

MS Genetics Consortium et al., "Genetic risk and a primary role for cell-mediated immune mechanisms in multiple sclerosis", Nature, Aug. 10, 2011, vol. 476, No. 7359, pp. 214-219, doi:10.1038/nature10251.

Najmabadi et al., "Deep sequencing reveals 50 novel genes for recessive cognitive disorders", Nature, Oct. 6, 2011, vol. 478, pp. 57-63, doi:10.1038/nature10423.

Neale et al., "Patterns and rates of exonic de novo mutations in autism spectrum disorders", Nature, Apr. 4, 2012, vol. 485, No. 7397, pp. 242-245, available in PMC Apr. 2, 2013, doi:10.1038/nature11011.

Neumann et al., "Ubiquitinated TDP-43 in Frontotemporal Lobar Degeneration and Amyotrophic Lateral Sclerosis", Science, vol. 314, No. 5796, Oct. 6, 2006, pp. 130-133, doi:10.1126/science.1134108.

Okser et al., "Regularized Machine Learning in the Genetic Prediction of Complex Traits", PLoS Genetics, Nov. 13, 2014, vol. 10, Issue. 11, e1004754, pp. 1-9.

O'Roak et al., "Sporadic autism exomes reveal a highly interconnected protein network of de novo mutations", Nature, May 10, 2012, vol. 485, pp. 246-250, published online Apr. 4, 2012, doi:10.1038/nature10989.

Packer, "Neocortical neurogenesis and the etiology of autism spectrum disorder", Neuroscience & Biobehavioral Reviews, May 2016, vol. 64, pp. 185-195, available online Mar. 3, 2016, http://dx.doi.org/10.1016/j.neubiorev.2016.03.002.

Pasaniuc et al., "Dissecting the genetics of complex traits using summary association statistics", bioRxiv, Retrieved from: https://www.biorxiv.org/content/10.1101/072934v1, Sep. 1, 2016, 28 pgs.

Pasaniuc et al., "Dissecting the genetics of complex traits using summary association statistics", Nature Reviews Genetics, Feb. 2017, vol. 18, pp. 117-127, published online Nov. 14, 2016, doi:10.1038/nrg.2016.142.

Pasini et al., "Suz12 is essential for mouse development and for EZH2 histone methyltransferase activity", The EMBO Journal, Oct. 13, 2004, vol. 23, No. 20, pp. 4061-4071, published online Sep. 23, 2004, doi:10.1038/sj.emboj.7600402.

Pinto et al., "Convergence of Genes and Cellular Pathways Dysregulated in Autism Spectrum Disorders", The American Journal of Human Genetics, May 1, 2014, vol. 94, pp. 677-694, http://dx.doi.org/10.1016/j.ajhg.2014.03.018.

Pinto et al., "Functional impact of global rare copy number variation in autism spectrum disorders", Nature, Jul. 15, 2010, vol. 466, pp. 368-372, published online Jun. 9, 2010, doi:10.1038/nature09146.

Plagnol et al., "Genome-Wide Association Analysis of Autoantibody Positivity in Type 1 Diabetes Cases", PLoS Genetics, vol. 7, No. 8, Aug. 2011, 9 pgs., doi:10.1371/journal.pgen.1002216.

Polymenidou et al., "Long pre-mRNA depletion and RNA missplicing contribute to neuronal vulnerability from loss of TDP-43",

(56) References Cited

OTHER PUBLICATIONS

Nature Neuroscience, vol. 14, published online as an Advance Online Publication, Feb. 27, 2011, pp. 459-468, doi:10.1038/nn.2779.

Power et al., "Fecundity of Patients With Schizophrenia, Autism, Bipolar Disorder, Depression, Anorexia Nervosa, or Substance Abuse vs Their Unaffected Siblings", Journal of the American Medical Association Psychiatry, 2013, vol. 70, No. 1, Jan. 2013, pp. 22-30, published Nov. 12, 2012, doi:10.1001/jamapsychiatry.2013.268.

Purcell et al., "A polygenic burden of rare disruptive mutations in schizophrenia", Nature, vol. 506, Feb. 13, 2014, pp. 185-190, doi:10.1038/nature12975.

Avsec et al., "Deep learning at base-resolution reveals motif syntax of the cis-regulatory codebioRxiv 737981 (2019) doi:10.1101/737981", bioRxiv, 737981, 2019, 63 pgs., doi:10.1101/737981.

Baron et al., "A Single-Cell Transcriptomic Map of the Human and Mouse Pancreas Reveals Inter- and Intra-cell Population Structure", Cell System, vol. 3, No. 4, Oct. 26, 2016, published online Sep. 22, 2016, pp. 346-360.e4, doi: 10.1016/j.cels.2016.08.011.

Bulik-Sullivan et al., "LD Score regression distinguishes confounding from polygenicity in genome-wide association studies", Nature Genetics, vol. 47, No. 3, Mar. 2015, published online Feb. 2, 2015, pp. 291-295. doi: 10.1038/ng.3211.

Butler et al., "Subset of individuals with autism spectrum disorders macrocephaly associated with germline PTEN tumour suppressor mutations", Journal Med. Genetics, vol. 4, No. 3, Apr. 2005, 10.1136/jmg.2004.024646.

Buxbaum et al., "Mutation screening of the PTEN gene in patients with autism spectrum disorders and macrocephaly", American Journal of Medical Genetics, Part B, Neuropsychiatry Genetics, vol. 144B, No. 4, Jun. 5, 2007, pp. 484-491, doi: 10.1002/ajmg.b.30493.

Cofer et al., "Modeling transcriptional regulation of model species with deep learning", Genome Research, vol. 31, No. 6, Jun. 2021, published online Apr. 22, 2021, pp. 1097-1105, doi: 10.1101/gr.266171.120.

Finucane et al., "Partitioning heritability by functional annotation using genome-wide association summary statistics", Nature Genetics, vol. 47, Nov. 2015, first published Sep. 28, 2015, pp. 1228-1235, https://doi.org/10.1038/ng.3404.

Habib et al., "Massively parallel single-nucleus RNA-seq with DroNc-seq", Nature Methods, vol. 14, No. 10, Oct. 2017, published online Aug. 28, 2017, pp. 955-958. doi: 10.1038/nmeth.4407.

Hawkins et al., "Distinct Epigenomic Landscapes of Pluripotent and Lineage-Committed Human Cells", Cell Stem Cell, vol. 6, Issue 5, May 7, 2010, pp. 479-491, DOI: https://doi.org/10.1016/j.stem.2010.03.018.

Ipe et al., "High-throughput assays to assess the functional impact of genetic variants: A road towards genomic-driven medicine", Clinical and Translational Science, (Year: 2017), 10(2), p. 67-77.

Kelley, "Cross-species regulatory sequence activity prediction", PLOS Computational Biology, vol. 16, No. 7, Jul. 20, 2020, 27 pgs., e1008050https://doi.org/10.1371/journal.pcbi.1008050.

Kelley et al., "Sequential regulatory activity prediction across chromosomes with convolutional neural networks", Genome Research, vol. 28, No. 5, May 2018, published online Mar. 7, 2018, pp. 739-750. doi: 10.1101/gr.227819.117.

Kerimov et al., "A compendium of uniformly processed human gene expression and splicing quantitative trait loci", Nature Genetics, vol. 53, Sep. 6, 2021, pp. 1290-1299, https://doi.org/10.1038/s41588-021-00924-w.

Kown et al., "Pten regulates neuronal arborization and social interaction in mice", Neuron, vol. 50, May 4, 2006, pp. 377-388, DOI 10.1016/j.neuron.2006.03.023.

Landrum et al., "ClinVar: improving access to variant interpretations and supporting evidence", Nucleic Acids Res, vol. 46, No. D, Jan. 4, 2018, published online Nov. 20, 2017, pp. D1062-D1067, doi: 10.1093/nar/gkx1153.

Luikart et al., "Pten knockdown in vivo increases excitatory drive onto dentate granule cells", Journal of Neuroscience, vol. 31, No. 11, Mar. 16, 2011, pp. 4345-4354. doi: 10.1523/JNEUROSCI.0061-11.2011.

Luwkoski et al., "A single-cell transcriptome atlas of the adult human retina", EMBO Journal, vol. 38, No. 18 e100811, Sep. 16, 2019, published online Aug. 22, 2019, 15 pgs., doi: 10.15252/embj.2018100811.

MacParland et al., "Single cell RNA sequencing of human liver reveals distinct intrahepatic macrophage populations", Nature Communications, vol. 9, No. 4383, 2018, 21 pgs., DOI: 10.1038/s41467-018-06318-7.

Madissoon et al., "scRNA-seq assessment of the human lung, spleen, and esophagus tissue stability after cold preservation", Genome Biology, vol. 21, No. 1, 2020, 16 pgs., https://doi.org/10.1186/s13059-019-1906-x.

Meuleman et al., "Index and biological spectrum of human DNase I hypersensitive sites", Nature, vol. 584, Aug. 13, 2020, first published Jul. 29, 2020, pp. 244-251, https://doi.org/10.1038/s41586-020-2559-3.

Stewart et al., "Spatiotemporal immune zonation of the human kidney", Science, vol. 365, No. 6460, Sep. 27, 2019, pp. 1461-1466, doi: 10.1126/science.aat5031.

Talium et al., "Sequencing of 53,831 diverse genomes from the NHLBI TOPMed Program", Nature, vol. 590, Feb. 11, 2021 first published Feb. 10, 2021, pp. 290-299, https://doi.org/10.1038/s41586-021-03205-y.

Welter et al., "The NHGRI GWAS Catalog, a curated resource of SNP-trait associations", Nucleic acids research, (Year: 2014) 42(D1), pp. D1001-D1006.

Yehia et al., "Copy Number Variation and Clinical Outcomes in Patients With Germline PTEN Mutations", Journal of the American Medical Association Network Open, vol. 3, No. 1, Jan. 31, 2020, e1920415. doi:10.1001/jamanetworkopen.2019.20415.

Ramasamy et al., "Genetic variability in the regulation of gene expression in ten regions of the human brain", Nature Neuroscience, vol. 17, Oct. 2014, pp. 1418-1428, published online Aug. 31, 2014, doi:10.1038/nn.3801.

Rice et al., "Dosage-sensitive genes in evolution and disease", BMC Biology, Sep. 1, 2017, vol. 15, No. 78, 10 pgs. DOI 10.1186/s12915-017-0418-y.

Ryoichiro et al., "The Notch-Hes pathway in mammalian neural development", Cell Research, vol. 9, Sep. 1, 1999, pp. 179-188.

Saied-Santiago et al., "Diverse Roles for Glycosaminoglycans in Neural Patterning", Developmental Dynamics, Jul. 24, 2017, vol. 247, No. 1, pp. 54-74, DOI: 10.1002/DVDY.24555.

Sanders et al., "De novo mutations revealed by whole exome sequencing are strongly associated with autism", Nature, Apr. 4, 2012, vol. 485, No. 7397, pp. 237-241, doi:10.1038/nature10945.

Sanders et al., "Insights into Autism Spectrum Disorder Genomic Architecture and Biology from 71 Risk Loci", Neuron, Sep. 23, 2015, vol. 87, No. 6, pp. 1215-1233, http://dx.doi.org/10.1016/j.neuron.2015.09.016.

Sanders et al., "Multiple Recurrent De Novo CNVs, Including Duplications of the 7q11.23 Williams Syndrome Region, Are Strongly Associated with Autism", Neuron, Jun. 9, 2011, vol. 70, No. 5, pp. 863-885, DOI: 10.1016/j.neuron.2011.05.002.

Scheckel et al., "Regulatory consequences of neuronal ELAV-like protein binding to coding and non-coding RNAs in human brain", eLife, vol. 5, e10421, Feb. 19, 2016, 35 pgs., https://doi.org/10.7554/eLife.10421.001.

Sebat et al., "Strong Association of De Novo Copy Number Mutations with Autism", Science, Apr. 20, 2007, vol. 316, No. 5823, pp. 445-449, published online Mar. 15, 2007, doi:10.1126/science.1138659.

Segal et al., "Predicting expression patterns from regulatory sequence in *Drosophila* segmentation", Nature, vol. 451, Jan. 2, 2008, pp. 535-540.

Singh et al., "Rare schizophrenia risk variants are enriched in genes shared with neurodevelopmental disorders", bioRxiv, Retrieved from: https://www.biorxiv.org/content/10.1101/069344v1, Aug. 16, 2016, 25 pgs.

(56) References Cited

OTHER PUBLICATIONS

Smit et al., "RepeatMasker 4.0", RepeatMasker, Retrieved from: http://www.repeatmasker.org/ on Jan. 17, 2013, Jan. 10, 2013, 1 pg.

Splawski et al., "CACNA1H Mutations in Autism Spectrum Disorders", The Journal of Biological Chemistry, vol. 281, No. 31, Aug. 4, 2006, pp. 22085-22091.

Sreedharan et al., "TDP-43 Mutations in Familial and Sporadic Amyotrophic Lateral Sclerosis", Science, Mar. 21, 2008, vol. 319, No. 5870, pp. 1668-1672, doi:10.1126/science.1154584.

Stenson et al., "The Human Gene Mutation Database: 2008 update", Genome Medicine, Jan. 22, 2009, vol. 1, No. 13, 6 pgs., doi:10.1186/gm13.

Stenson et al., "The Human Gene Mutation Database: building a comprehensive mutation repository for clinical and molecular genetics, diagnostic testing and personalized genomic medicine", Human Genetics, Sep. 28, 2013, vol. 133, pp. 1-9, DOI 10.1007/s00439-013-1358-4.

Storey et al., "Statistical significance for genomewide studies", PNAS, Aug. 5, 2003, vol. 100, No. 16, pp. 9440-9445, www.pnas.org/cgi/doi/10/1073/pnas.1530509100.

Sun et al., "Histone Acetylome-wide Association Study of Autism Spectrum Disorder", Cell, Nov. 17, 2016, vol. 167, No. 5, pp. 1385-1397.e11, http://dx.doi.org/10.1016/j.cell.2016.10.031.

Tang et al., "A Genome-Wide Association Study for Venous Thromboembolism: The Extended Cohorts for Heart and Aging Research in Genomic Epidemiology (CHARGE) Consortium", Genetic Epidemiology, Jul. 2013, vol. 37, pp. 512-521, DOI:10.1002/gepi.21731.

Tewhey et al., "Direct Identification of Hundreds of Expression-Modulating Variants using a Multiplexed Reporter Assay", Cell, Jun. 2, 2016, vol. 165, No. 6, pp. 1519-1529, http://dx.doi.org/10.1016/j.cell.2016.04.027.

The Encode Project Consortium, "An integrated encyclopedia of DNA elements in the human genome", Nature, vol. 489, Sep. 6, 2012, pp. 57-74, doi:10.1038/nature11247.

The Fantom Consortium et al., "A promoter-level mammalian expression atlas", Nature, Mar. 26, 2014, vol. 507, No. 7493, pp. 462-470, doi:10.1038/nature13182.

Thurman et al., "Language Skills of Males with Fragile X Syndrome or Nonsyndromic Autism Spectrum Disorder", Journal of Autism and Developmental Disorders, Jan. 10, 2017, vol. 47, pp. 728-743, doi:10.1007/s10803-016-3003-2.

Turner et al., "Genome Sequencing of Autism-Affected Families Reveals Disruption of Putative Noncoding Regulatory DNA", The American Journal of Human Genetics, Jan. 7, 2016, vol. 98, No. 1, pp. 58-74, http://dx.doi.org/10.1016/j.ajhg.2015.11.023.

Turner et al., "Genomic Patterns of De Novo Mutation in Simplex Autism", Cell, Oct. 19, 2017, vol. 171, No. 3, pp. 710-722.e12, http://dx.doi.org/10.1016/j.cell.2017.08.047.

Uhlen et al., "Tissue-based map of the human proteome", Science, Jan. 23, 2015, vol. 347, No. 6220, pp. 1260419-1-1260419-9, doi:10.1126/science.1260419.

Ule et al., "CLIP Identifies Nova-Regulated RNA Networks in the Brain", Science, Nov. 14, 2003, vol. 302, No. 5648, pp. 1212-1215, www.sciencemag.org/cgi/content/full/302/5648/1212/DC1.

Ule et al., "The Future of Cross-Linking and Immunoprecipitation (CLIP)", Cold Spring Harbor Perspectives in Biology, vol. 10, No. 8, Aug. 1, 2018, a032243, 12 pgs., doi: 10.1101/cshperspect.a032243.

Valente et al., "Hereditary Early-Onset Parkinson's Disease Caused by Mutations in PINK1", Science, vol. 304, No. 5674, May 21, 2004, pp. 1158-1160, doi:10.1126/science.1096284.

Van De Geijn et al., "WASP: allele-specific software for robust molecular quantitative trait locus discovery", Nature Methods, Nov. 2015, vol. 12, No. 2, pp. 1061-1063, published online Sep. 14, 2015, DOI:10.1038/NMETH.3582.

Van Der Maaten et al., "Visualizing Data using t-SNE", Journal of Machine Learning Research, vol. 9, Nov. 2008, pp. 2579-2605.

Van Nostrand et al., "Robust transcriptome-wide discovery of RNA-binding protein binding sites with enhanced CLIP (eCLIP)", Nature Methods, Mar. 28, 2016, vol. 13, No. 6, pp. 508-514, doi:10.1038/nmeth.3810.

Veltman et al., "De novo mutations in human genetic disease", Nature Reviews Genetics, vol. 13, Aug. 2012, pp. 565-575, doi:10.1038/nrg3241.

Verkerk et al., "Identification of a Gene (FMR-1) Containing a CGG Repeat Coincident with a Breakpoint Cluster Region Exhibiting Length Variation in Fragile X Syndrome", Cell, vol. 65, No. 5, May 31, 1991, pp. 905-914.

Vissers et al., "Genetic studies in intellectual disability and related disorders", Nature Reviews Genetics, vol. 17, Oct. 27, 2015, pp. 9-18.

Walsh et al., "Autism and Brain Development", Cell, Oct. 31, 2008, vol. 135, No. 3, pp. 396-400, DOI 10.1016/j.cell.2008.10.015.

Wang et al., "Alternative isoform regulation in human tissue transcriptomes", Nature, vol. 456, Nov. 27, 2008, pp. 470-476.

Weiner et al., "Polygenic transmission disequilibrium confirms that common and rare variation act additively to create risk for autism spectrum disorders", Nature Genetics, vol. 49, No. 7, May 15, 2017, vol. 49, No. 7, pp. 978-985, doi:10.1038/ng.3863.

Wellcome Trust Case Control, "Genome-wide association study of 14,000 cases of seven common diseases and 3,000 shared controls", Nature, Jun. 7, 2007, vol. 447, No. 7145, pp. 661-678, doi:10.1038/nature05911.

Werling et al., "An analytical framework for whole-genome sequence association studies and its implications for autism spectrum disorder", Nature Genetics, vol. 50, Apr. 26, 2018, pp. 727-736.

Werling et al., "Limited contribution of rare, noncoding variation to autism spectrum disorder from sequencing of 2,076 genomes in quartet families", bioRxiv, Retrieved from: https://doi.org/10.1101/127043, Apr. 13, 2017, 45 pgs.

Werling et al., "Sex differences in autism spectrum disorders", Current Opinion in Neurology, Apr. 2013, vol. 26, No. 2, pp. 146-153, doi:10.1097/WCO.0b013e32835ee548.

Westra et al., "Systematic identification of trans eQTLs as putative drivers of known disease associations", Nature Genetics, Oct. 2013, vol. 45, pp. 1238-1243, published online Sep. 8, 2013, doi:10.1038/ng.2756.

Williams et al., "Haploinsufficiency of HDAC4 Causes Brachydactyly Mental Retardation Syndrome, with Brachydactyly Type E, Developmental Delays, and Behavioral Problems", The American Journal of Human Genetics, Aug. 13, 2010, vol. 87, pp. 219-228, DOI 10.1016/j.ajhg.2010.07.011.

Willsey et al., "Coexpression Networks Implicate Human Midfetal Deep Cortical Projection Neurons in the Pathogenesis of Autism", Cell, Nov. 21, 2013, vol. 155, No. 5, pp. 997-1007, DOI:https://doi.org/10.1016/j.cell.2013.10.020.

Xiao et al., "Molecular mechanisms underlying noncoding risk variations in psychiatric genetic studies", Molecular Psychiatry, 2017, vol. 22, pp. 497-511, published online Jan. 3, 2017, doi:10.1038/mp.2016.241.

Yan et al., "Systematic discovery of regulated and conserved alternative exons in the mammalian brain reveals NMD modulating chromatin regulators", Proceedings of the National Academy of Sciences, Mar. 17, 2015, vol. 112, No. 11, pp. 3445-3450, www.pnas.org/cgi/doi/10.1073/pnas.1502849112.

Yuan et al., "Predicting Gene Expression from Sequence: A Reexamination", PLoS Computational Biology, Nov. 30, 2007, vol. 3, No. 11, e243, pp. 2391-2397, doi:10.1371/journal.pcbi.0030243.g001.

Yuen et al., "Whole genome sequencing resource identifies 18 new candidate genes for autism spectrum disorder", Nature Neuroscience, advanced online publication, Mar. 6, 2017, 13 pgs., doi:10.1038/nn.4524.

Yuen et al., "Whole-genome sequencing of quartet families with autism spectrum disorder", Nature Medicine, Feb. 2015, vol. 21, pp. 185-191, published online Jan. 26, 2015; doi:10.1038/nm.3792.

Zhang et al., "Integrative Modeling Defines the Nova Splicing-Regulatory Network and Its Combinatorial Controls", Science, Jul. 23, 2010, pp. 439-443, vol. 329, No. 5990, doi:10.1126/science.1191150.

(56) References Cited

OTHER PUBLICATIONS

Zhang et al., "Mapping in vivo protein-RNA interactions at single-nucleotide resolution from HITS-CLIP data", Nature Biotechnology, Jun. 1, 2011, vol. 29, pp. 607-614, doi:10.1038/nbt.1873.

Zhou et al., "Deep learning sequence-based ab initio prediction of variant effects on expression and disease risk", Nature Genetics, Jul. 16, 2018, vol. 50, No. 8, pp. 1171-1179, doi:10.1038/s41588-018-0160-6.

Zhou et al., "Predicting effects of noncoding variants with deep learning-based sequence model", Nature Methods, Oct. 2015, vol. 12, Issue 10, 931-934, published online Aug. 24, 2015, doi:10.1038/NMETH.3547.

Zhou et al., "Whole-genome deep learning analysis reveals causal role of noncoding mutations in autism", bioRxiv, Retrieved from: https://www.biorxiv.org/content/10.1101/319681v1, May 11, 2018, 29 pgs.

Risca et al., "Unraveling the 3D genome: genomics tools for multiscale exploration", Trends in Genetics, 2015, 31(7), pp. 357-372.

\* cited by examiner

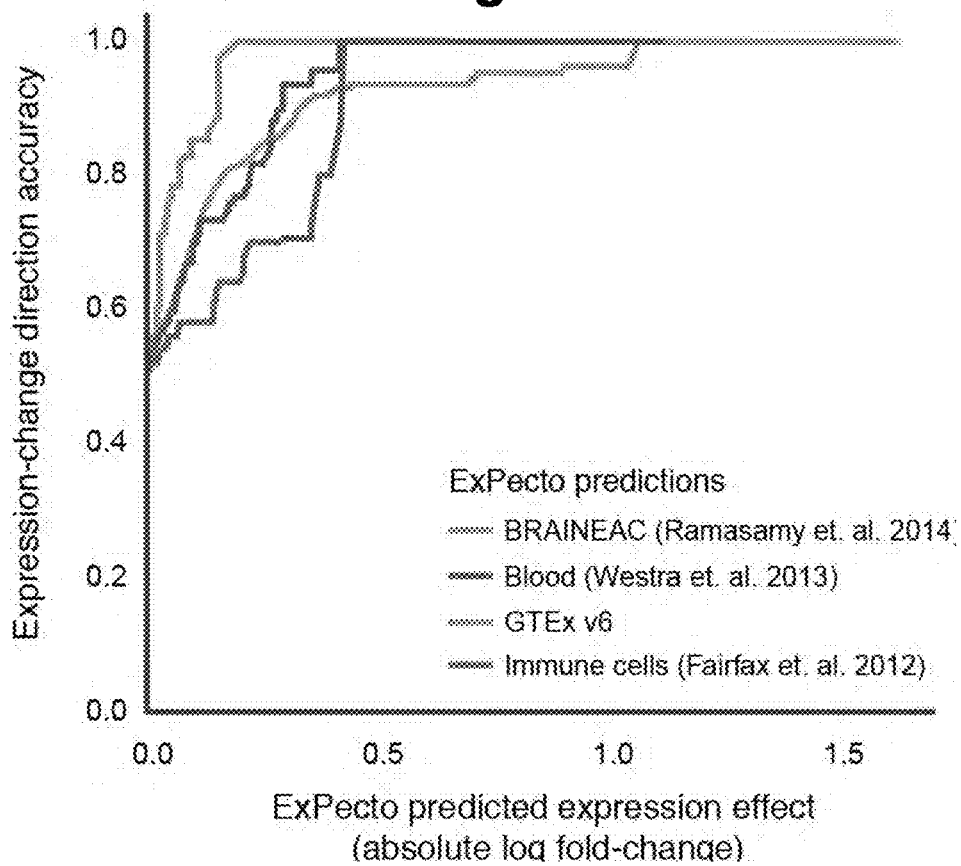
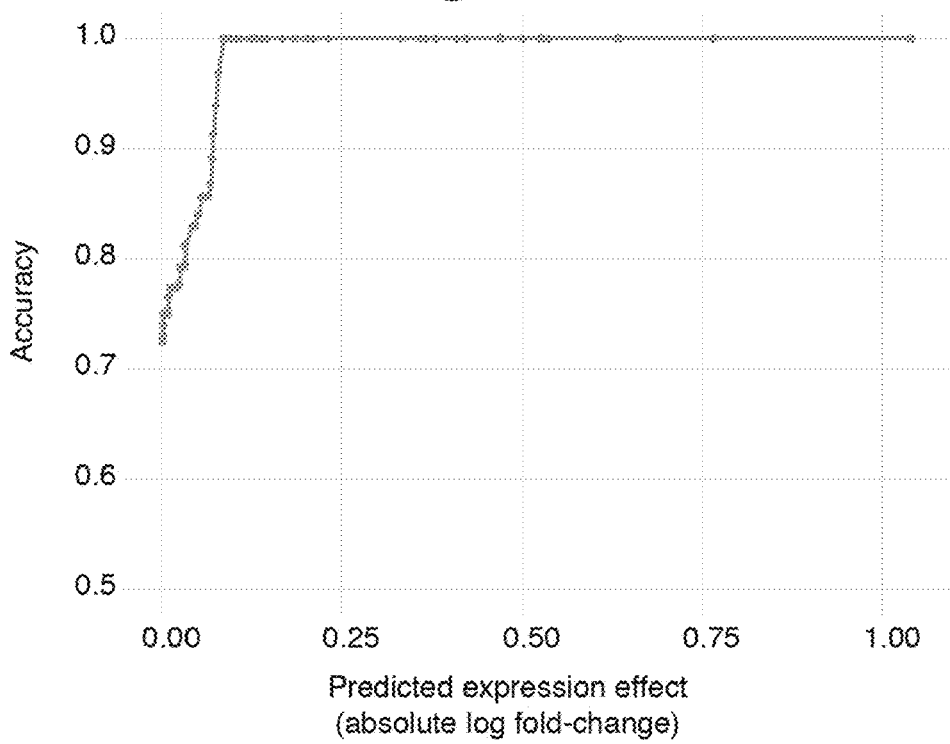

METHODS FOR PREDICTING GENOMIC VARIATION EFFECTS ON GENE TRANSCRIPTION

CROSS REFERENCE TO RELATED APPLICATIONS

This application is a national stage of PCT Patent Application No. PCT/US2019/024108, entitled "Methods for Predicting Genomic Variation Effects on Gene Transcription" to Zhou et al., filed Mar. 26, 2019, which claims priority to U.S. Provisional Application Ser. No. 62/648,355 entitled "Predicting the Effects of Genomic Variation on Human Gene Transcription and Correlating with Disease Risk," filed Mar. 26, 2018, which is incorporated herein by reference in its entirety.

STATEMENT REGARDING FEDERALLY SPONSORED RESEARCH OR DEVELOPMENT

This invention was made with Government support under Grants No. HHSN272201000054C, No. GM071966, No. HL117798, and No. HG005998 awarded by the National Institutes of Health. The Government has certain rights in the invention.

REFERENCE TO A SEQUENCE LISTING SUBMITTED ELECTRONICALLY VIA EFS-WEB

The instant application contains a Sequence Listing which has been filed electronically in ASCII format and is hereby incorporated by reference in its entirety. Said ASCII copy, created on Sep. 25, 2020, is named 06010 Seq List ST25 and is 9 kilobytes in size.

FIELD OF THE INVENTION

The invention is generally directed to methods and processes for genetic data evaluation, and more specifically to methods and systems utilizing genetic data to determine gene expression levels and applications thereof.

BACKGROUND

Eukaryotic cells utilize complexes of DNA, RNA and protein, referred to as chromatin, to regulate gene expression and thus control its cellular function. When a DNA strand is in a packed, condensed chromatin state, genes on the DNA strand are repressed from expressing. On the contrary, when a DNA strand is in an unpacked, open chromatin state, genes on the DNA are expressed to produce RNA and subsequent protein products. A cell will modulate its chromatin status along DNA strands to control gene expression.

Within the sequence of a cell's DNA are elements that recruit various factors to modulate chromatin and gene expression. Various gene expression elements include transcription factor binding sites, operators, enhancers, silencers, promoters, transcriptional start sites, and insulators. Single nucleotide variations, nucleotide insertions, and nucleotide deletions in genetic sequences that affect chromatin formation can produce various effects on gene expression, resulting in heterogeneity in gene expression between different DNA sequences.

SUMMARY OF THE INVENTION

Several embodiments are directed to methods and processes to evaluate variants that affect expression levels of transcripts.

In an embodiment to evaluate gene expression, genetic data is obtained from a biological sample. The genetic data includes at least one gene sequence. The expression level of the at least gene is determined utilizing a computational framework. The computational framework utilizes the genetic data to determine epigenetic regulatory features spatially along a genetic sequence that includes the at least one gene sequence. The computational framework determines the expression level of the at least one gene based on the epigenetic regulatory features along the genetic sequence that includes the at least one gene sequence. A biochemical assay to assess the biological sample is performed based on the determination of the expression level of the at least one gene.

In another embodiment, the biological sample is one of: a biopsy of an individual, an in vitro cell line, or a mouse research model.

In yet another embodiment, the genetic data has been obtained by extracting DNA from the biological sample.

In a further embodiment, the epigenetic regulatory features include at least one of: sites of chromatin accessibility, chromatin marks, and transcription factor binding sites.

In still yet another embodiment, the computational framework includes a deep convolutional neural network to determine the epigenetic regulatory features spatially along the genetic sequence.

In yet a further embodiment, the deep convolutional neural network is trained on epigenetic regulatory data acquired by at least one epigenetic assay.

In an even further embodiment, the epigenetic is assay is one of: chromatin immunoprecipitation sequencing (ChIP-seq), DNAse I hypersensitivity sequencing (DNase-seq), Assay for Transposase-Accessible Chromatin sequencing (ATAC-seq), Formaldehyde-Assisted Isolation of Regulatory Elements (FAIRE-seq), Hi-C capture sequencing, bisulfite sequencing (BS-seq), or methyl array.

In yet an even further embodiment, the deep convolutional neural network determines the epigenetic regulatory features spatially along the genetic sequence by considering single nucleotide variants, insertions, and deletions within the genetic sequence.

In still yet an even further embodiment, the computational framework is trained for a particular cell-type or tissue.

In still yet an even further embodiment, the computational framework determines the epigenetic regulatory features spatially along the genetic sequence for all Poll II transcribed genes of an organismal genome.

In still yet an even further embodiment, the computational framework determines the epigenetic regulatory features spatially along the genetic sequence in reference to a sequence structure of the at least one gene.

In still yet an even further embodiment, the sequence structure is a transcription start site or promoter sequence.

In still yet an even further embodiment, the computational framework determines the epigenetic regulatory features 1 kb, 2 kb, 3 kb, 4, kb, 5 kb, 7.5 kb, 10 kb, 15 kb, 20 kb, 25 kb, or 50 kb upstream of the gene sequence structure.

In still yet an even further embodiment, the computational framework determines the epigenetic regulatory features 1 kb, 2 kb, 3 kb, 4, kb, 5 kb, 7.5 kb, 10 kb, 15 kb, 20 kb, 25 kb, or 50 kb downstream of the gene sequence structure.

In still yet an even further embodiment, the computational framework determines the epigenetic regulatory features spatially along the genetic sequence in sequence bins, wherein the sequence bins are 50 bp, 100 bp, 150 bp, 200 bp, 250 bp, 300 bp, 400 bp, or 500 bp in length.

In still yet an even further embodiment, the computational framework considers the surrounding sequence context to determine the epigenetic regulatory features for each sequence bin.

In still yet an even further embodiment, the computational framework spatially transforms the epigenetic regulatory features that are determined.

In still yet an even further embodiment, the computational framework includes a linear regression model to determine the expression level of the at least one gene based on the epigenetic regulatory features along the genetic sequence.

In still yet an even further embodiment, the linear regression model is L2 regularized.

In still yet an even further embodiment, the biochemical assay is one of: chromatin immunoprecipitation sequencing (ChIP-seq), DNAse I hypersensitivity sequencing (DNase-seq), Assay for Transposase-Accessible Chromatin sequencing (ATAC-seq), Formaldehyde-Assisted Isolation of Regulatory Elements (FAIRE-seq), Hi-C capture sequencing, bisulfite sequencing (BS-seq), methyl array, transgene expression analysis (e.g., luciferase and eGFP), qPCR, RNA hybridization (e.g., ISH), cross-linking immunoprecipitation sequencing (CLIP-seq), RNA immunoprecipitation sequencing (RIP-seq), RNA-seq, western blot, immunodetection, flow cytometry, enzyme-linked immunosorbent assay (ELISA), or mass spectrometry.

In an embodiment to treat an individual for a medical disorder that arises due to gene expression levels, genetic data is obtained from a biological sample of an individual. The genetic data includes at least one gene sequence involved in a medical disorder that arises due to an expression level of the at least one gene. The expression level of the at least gene is determined utilizing a computational framework. The computational framework utilizes the genetic data to determine epigenetic regulatory features along a genetic sequence that includes the at least one gene sequence. The computational framework determines the expression level of the at least one gene based on the epigenetic regulatory features along the genetic sequence that includes the at least one gene sequence. The individual is treated for the medical disorder based on the determination of the expression level of the at least one gene. The expression level of the at least one gene indicates the individual has the medical disorder.

In another embodiment, the biological sample is a biopsy of the individual.

In yet another embodiment, the genetic data has been obtained by extracting DNA from the biological sample.

In a further embodiment, the epigenetic regulatory features include at least one of: sites of chromatin accessibility, chromatin marks, and transcription factor binding sites.

In still yet another embodiment, the computational framework includes a deep convolutional neural network to determine the epigenetic regulatory features spatially along the genetic sequence.

In yet a further embodiment, the deep convolutional neural network is trained on epigenetic regulatory data acquired by at least one epigenetic assay.

In an even further embodiment, the epigenetic is assay is one of: chromatin immunoprecipitation sequencing (ChIP-seq), DNAse I hypersensitivity sequencing (DNase-seq), Assay for Transposase-Accessible Chromatin sequencing (ATAC-seq), Formaldehyde-Assisted Isolation of Regulatory Elements (FAIRE-seq), Hi-C capture sequencing, bisulfite sequencing (BS-seq), or methyl array.

In yet an even further embodiment, the deep convolutional neural network determines the epigenetic regulatory features spatially along the genetic sequence by considering single nucleotide variants, insertions, and deletions within the genetic sequence.

In still yet an even further embodiment, the computational framework is trained for a particular cell-type or tissue.

In still yet an even further embodiment, the computational framework determines the epigenetic regulatory features spatially along the genetic sequence for all Poll II transcribed genes of an organismal genome.

In still yet an even further embodiment, the computational framework determines the epigenetic regulatory features spatially along the genetic sequence in reference to a sequence structure of the at least one gene.

In still yet an even further embodiment, the sequence structure is a transcription start site or promoter sequence.

In still yet an even further embodiment, the computational framework determines the epigenetic regulatory features 1 kb, 2 kb, 3 kb, 4, kb, 5 kb, 7.5 kb, 10 kb, 15 kb, 20 kb, 25 kb, or 50 kb upstream of the gene sequence structure.

In still yet an even further embodiment, the computational framework determines the epigenetic regulatory features 1 kb, 2 kb, 3 kb, 4, kb, 5 kb, 7.5 kb, 10 kb, 15 kb, 20 kb, 25 kb, or 50 kb downstream of the gene sequence structure.

In still yet an even further embodiment, the computational framework determines the epigenetic regulatory features spatially along the genetic sequence in sequence bins, wherein the sequence bins are 50 bp, 100 bp, 150 bp, 200 bp, 250 bp, 300 bp, 400 bp, or 500 bp in length.

In still yet an even further embodiment, the computational framework considers the surrounding sequence context to determine the epigenetic regulatory features for each sequence bin.

In still yet an even further embodiment, the computational framework spatially transforms the epigenetic regulatory features that are determined.

In still yet an even further embodiment, the computational framework includes a linear regression model to determine the expression level of the at least one gene based on the epigenetic regulatory features along the genetic sequence.

In still yet an even further embodiment, the linear regression model is L2 regularized.

In still yet an even further embodiment, treating the individual includes administering a therapeutic.

In an embodiment, genetic data is obtained from a biological sample of an individual. The genetic data includes at least one gene sequence involved in metabolism of a therapeutic that is used to treat a medical disorder being experienced by the individual. The expression level of the at least gene is determined utilizing a computational framework. The computational framework utilizes the genetic data to determine epigenetic regulatory features along a genetic sequence that includes the at least one gene sequence. The computational framework determines the expression level of the at least one gene based on the epigenetic regulatory features along the genetic sequence that includes the at least one gene sequence. A therapeutic is administered to the individual. The expression level of the at least one gene indicates an ability to metabolize the therapeutic.

In another embodiment, the biological sample is a biopsy of an individual.

In yet another embodiment, the genetic data has been obtained by extracting DNA from the biological sample.

In a further embodiment, the epigenetic regulatory features include at least one of: sites of chromatin accessibility, chromatin marks, and transcription factor binding sites.

In still yet another embodiment, the computational framework includes a deep convolutional neural network to determine the epigenetic regulatory features spatially along the genetic sequence.

In yet a further embodiment, the deep convolutional neural network is trained on epigenetic regulatory data acquired by at least one epigenetic assay.

In an even further embodiment, the epigenetic is assay is one of: chromatin immunoprecipitation sequencing (ChIP-seq), DNAse I hypersensitivity sequencing (DNase-seq), Assay for Transposase-Accessible Chromatin sequencing (ATAC-seq), Formaldehyde-Assisted Isolation of Regulatory Elements (FAIRE-seq), Hi-C capture sequencing, bisulfite sequencing (BS-seq), or methyl array.

In yet an even further embodiment, the deep convolutional neural network determines the epigenetic regulatory features spatially along the genetic sequence by considering single nucleotide variants, insertions, and deletions within the genetic sequence.

In still yet an even further embodiment, the computational framework is trained for a particular cell-type or tissue.

In still yet an even further embodiment, the computational framework determines the epigenetic regulatory features spatially along the genetic sequence for all Poll II transcribed genes of an organismal genome.

In still yet an even further embodiment, the computational framework determines the epigenetic regulatory features spatially along the genetic sequence in reference to a sequence structure of the at least one gene.

In still yet an even further embodiment, the sequence structure is a transcription start site or promoter sequence.

In still yet an even further embodiment, the computational framework determines the epigenetic regulatory features 1 kb, 2 kb, 3 kb, 4, kb, 5 kb, 7.5 kb, 10 kb, 15 kb, 20 kb, 25 kb, or 50 kb upstream of the gene sequence structure.

In still yet an even further embodiment, the computational framework determines the epigenetic regulatory features 1 kb, 2 kb, 3 kb, 4, kb, 5 kb, 7.5 kb, 10 kb, 15 kb, 20 kb, 25 kb, or 50 kb downstream of the gene sequence structure.

In still yet an even further embodiment, the computational framework determines the epigenetic regulatory features spatially along the genetic sequence in sequence bins, wherein the sequence bins are 50 bp, 100 bp, 150 bp, 200 bp, 250 bp, 300 bp, 400 bp, or 500 bp in length.

In still yet an even further embodiment, the computational framework considers the surrounding sequence context to determine the epigenetic regulatory features for each sequence bin.

In still yet an even further embodiment, the computational framework spatially transforms the epigenetic regulatory features that are determined.

In still yet an even further embodiment, the computational framework includes a linear regression model to determine the expression level of the at least one gene based on the epigenetic regulatory features along the genetic sequence.

In still yet an even further embodiment, the linear regression model is L2 regularized.

In still yet an even further embodiment, a lower dose of the therapeutic or an alternative therapeutic is administered when the individual is determined to have a reduced ability to metabolize the therapeutic.

In still yet an even further embodiment, a higher dose of the therapeutic or an alternative therapeutic is administered when the individual is determined to have an increased ability to metabolize the therapeutic.

In still yet an even further embodiment, the therapeutic is one of: abacavir, acenocoumarol, allopurinol, amitriptyline, aripiprazole, atazanavir, atomoxetine, azathioprine, capecitabine, carbamazepine, carvedilol, cisplatin, citalopram, clomipramine, clopidogrel, clozapine, codeine, daunorubicin, desflurane, desipramine, doxepin, doxorubicin, duloxetine, enflurane, escitalopram, esomeprazole, flecainide, fluorouracil, flupenthixol, fluvoxamine, glibenclamide, gliclazide, glimepiride, haloperidol, halothane, imipramine, irinotecan, isoflurane, ivacaftor, lansoprazole, mercaptopurine, methoxyflurane, metoprolol, mirtazapine, moclobemide, nortriptyline, olanzapine, omeprazole, ondansetron, oxcarbazepine, oxycodone, pantoprazole, paroxetine, peginterferon alpha-2a, peginterferon alpha-2b, phenprocoumon, phenytoin, propafenone, rabeprazole, rasburicase, ribavirin, risperidone, sertraline, sevoflurane, simvastatin, succinylcholine, tacrolimus, tamoxifen, tegafur, thioguanine, tolbutamide, tramadol, trimipramine, tropisetron, venlafaxine, voriconazole, warfarin, or zuclopenthixol.

In an embodiment to perform site-directed mutagenesis on a biological sample, genetic data is obtained from a biological sample. The genetic data includes at least one gene sequence. The expression level of the at least gene is determined utilizing a computational framework. The computational framework utilizes the genetic data to determine epigenetic regulatory features along a genetic sequence that includes the at least one gene sequence. The computational framework determines the expression level of the at least one gene based on the epigenetic regulatory features along the genetic sequence that includes the at least one gene sequence. A set of one or more genetic variants that alter the expression level of the at least one gene is determined utilizing the computational framework. The set of variants that alter the expression level of the at least one gene are not present in the genetic sequence of the biological sample. Site-directed mutagenesis is performed on the DNA of the biological sample to introduce the set of variants based on the determination of the set of variants that alter the expression level of the at least one gene.

In another embodiment, the biological sample is one of: a biopsy of an individual, ex vivo tissue of an individual, an in vitro cell line, embryonic tissue, or a mouse research model.

In yet another embodiment, the genetic data has been obtained by extracting DNA from the biological sample.

In a further embodiment, the epigenetic regulatory features include at least one of: sites of chromatin accessibility, chromatin marks, and transcription factor binding sites.

In still yet another embodiment, the computational framework includes a deep convolutional neural network to determine the epigenetic regulatory features spatially along the genetic sequence.

In yet a further embodiment, the deep convolutional neural network is trained on epigenetic regulatory data acquired by at least one epigenetic assay.

In an even further embodiment, the epigenetic is assay is one of: chromatin immunoprecipitation sequencing (ChIP-seq), DNAse I hypersensitivity sequencing (DNase-seq), Assay for Transposase-Accessible Chromatin sequencing (ATAC-seq), Formaldehyde-Assisted Isolation of Regulatory Elements (FAIRE-seq), Hi-C capture sequencing, bisulfite sequencing (BS-seq), or methyl array.

In yet an even further embodiment, the deep convolutional neural network determines the epigenetic regulatory features spatially along the genetic sequence by considering single nucleotide variants, insertions, and deletions within the genetic sequence.

In still yet an even further embodiment, the computational framework is trained for a particular cell-type or tissue.

In still yet an even further embodiment, the computational framework determines the epigenetic regulatory features spatially along the genetic sequence for all Poll II transcribed genes of an organismal genome.

In still yet an even further embodiment, the computational framework determines the epigenetic regulatory features spatially along the genetic sequence in reference to a sequence structure of the at least one gene.

In still yet an even further embodiment, the sequence structure is a transcription start site or promoter sequence.

In still yet an even further embodiment, the computational framework determines the epigenetic regulatory features 1 kb, 2 kb, 3 kb, 4, kb, 5 kb, 7.5 kb, 10 kb, 15 kb, 20 kb, 25 kb, or 50 kb upstream of the gene sequence structure.

In still yet an even further embodiment, the computational framework determines the epigenetic regulatory features 1 kb, 2 kb, 3 kb, 4, kb, 5 kb, 7.5 kb, 10 kb, 15 kb, 20 kb, 25 kb, or 50 kb downstream of the gene sequence structure.

In still yet an even further embodiment, the computational framework determines the epigenetic regulatory features spatially along the genetic sequence in sequence bins, wherein the sequence bins are 50 bp, 100 bp, 150 bp, 200 bp, 250 bp, 300 bp, 400 bp, or 500 bp in length.

In still yet an even further embodiment, the computational framework considers the surrounding sequence context to determine the epigenetic regulatory features for each sequence bin.

In still yet an even further embodiment, the computational framework spatially transforms the epigenetic regulatory features that are determined.

In still yet an even further embodiment, the computational framework includes a linear regression model to determine the expression level of the at least one gene based on the epigenetic regulatory features along the genetic sequence.

In still yet an even further embodiment, the linear regression model is L2 regularized.

In still yet an even further embodiment, the site-directed mutagenesis is performed by one of: CRISPR mutagenesis, Zinc-finger mutagenesis, or TALEN mutagenesis.

In still yet an even further embodiment, the biological sample is ex vivo tissue of the individual, and wherein the tissue is transplanted back into the individual after site-directed mutagenesis is performed.

In an embodiment is a kit to detect the presence of variants within genetic loci. The kit includes a set of nucleic acid oligomers to detect the presence of variants within a set of genomic loci. The set of genomic loci have been identified to have harbored a variant that alters transcription of at least one gene. The ability to alter transcription of at least one gene has been determined by a computational framework that utilizes genetic data to determine epigenetic regulatory features along a genetic sequence that includes the at least one gene sequence. The computational framework determines the ability to alter gene transcription based on the epigenetic regulatory features along the genetic sequence. Each locus the set of genomic loci is selected based upon harboring variants that altering gene transcription.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 14 provides a data graph that shows eQTL direction prediction accuracy increases with predicted magnitude of variant effect, generated in accordance with various embodiments of the invention.

FIG. 15 provide a data graph that shows ExPecto predicts in vitro reporter assay effects of validated casual eQTLs, generated in accordance with various embodiments of the invention.

DETAILED DESCRIPTION

Figure 1:
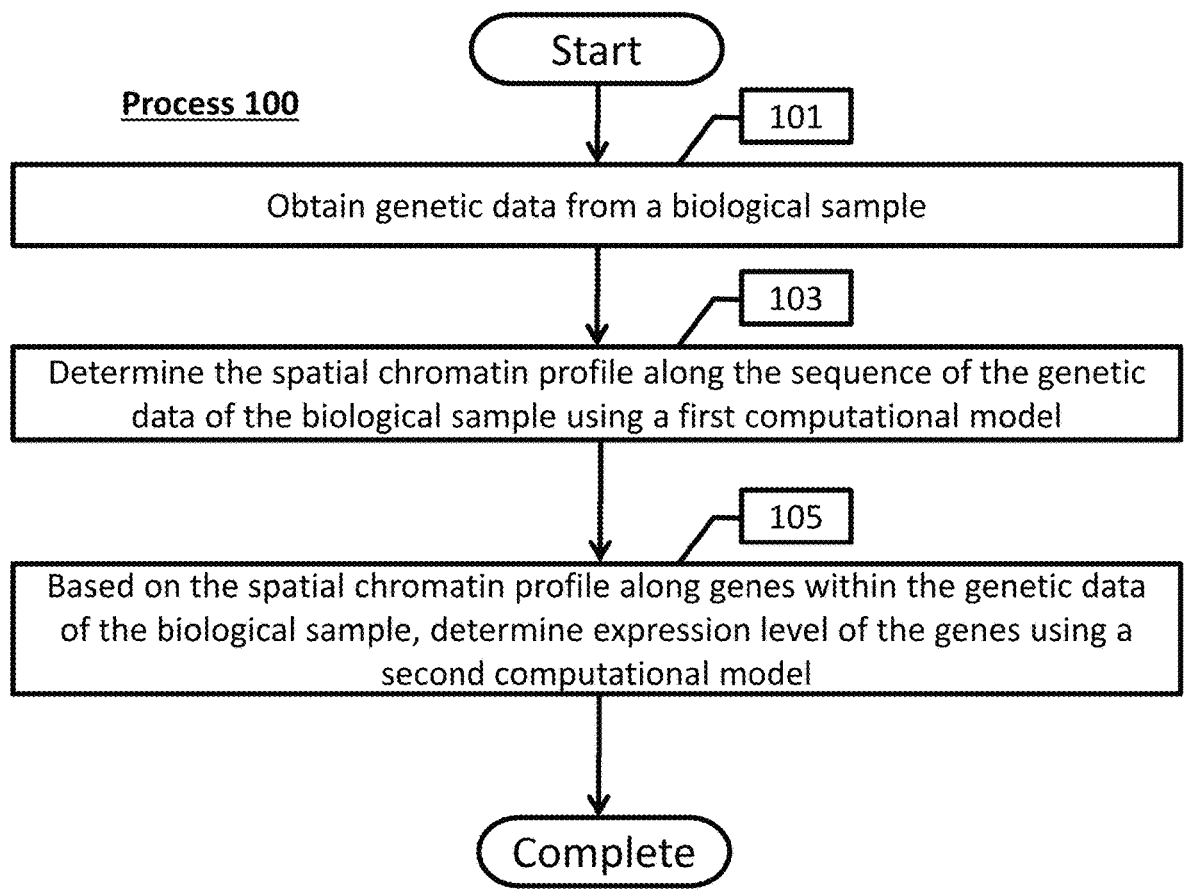
FIG. 1 provides a process to determine expression level of genes based genetic sequence in accordance with an embodiment of the invention.

Turning now to the drawings and data, a number of processes for genetic data extrapolation that can be utilized in gene expression analysis, diagnostics, medicament development, and/or treatments in accordance with various embodiments of the invention are illustrated. Numerous embodiments are directed towards a general framework and methods for determining expression of genes based on its sequence and surrounding sequence context. In several embodiments, methods are utilized to determine a spatial chromatin profile (i.e., local chromatin architecture) of a genetic sequence. In various embodiments, methods further use a spatial chromatin profile to infer expression of genes. In some embodiments, chromatin profiles and gene expression are based on tissue and/or cell-type. In some embodiments, methods extract the genetic sequence from a biological sample (e.g., biopsy of an individual) to determine gene expression in that biological sample, which may be used to diagnose an individual. And in some embodiments, an individual can be treated based on her diagnosis.

Sequence-dependent control of gene transcription is at the foundation of the complexity of multicellular organisms. Expression-altering genomic variation can thus have wide impact on human diseases and traits. Empirical observations of expression-genotype association from population genetics studies and predictive models based on matched expression and genotype data have provided valuable information for the expression effect of common genome variation and their relevance to disease, however, such approaches are generally limited to mutations that are observed frequently and with matched expression observations in ideally the relevant tissue/cell type. Moreover, core to the understanding of the regulatory potential for both common and rare variants is disentangling causality from association and extracting the dependency between sequence and expression effect, which remains as a major challenge.

A quantitative model that accurately predicts expression level ab initio from only sequence information will provide a causality link between genetic sequence variations and their effects on gene expression. As utilized herein, ab initio sequence-based prediction is capable of extracting causality because of the unidirectional flow of information from sequence change to consequent gene expression change. Moreover, it is envisioned that the potential of estimating effects for all possible variants, including previously unobserved ones, will enable a new framework for the study of variant-directed mutagenesis, variant effect on gene expression, sequence evolution and evolutionary constraints on gene expression. This will allow direct prediction of fitness impact due to genomic changes and the resulting expression alteration using only sequence. Resulting changes in expression can affect diagnostics and treatments.

Human gene expression profiles reveal a wide diversity of expression patterns across genes, cell types, cellular states, and response to medications. Yet the understanding of sequences that activate or repress expression and the ability to quantify the transcriptional modulation strength of a sequence element is incomplete. Progress in quantitative expression modeling has focused on model organisms with relatively small noncoding regions such as yeast and fly, and in the context of reporter expression prediction in human cell lines. As a result, current sequence-based expression prediction models are limited in accuracy or restricted to small subsets of genes, and utilize narrow regulatory regions smaller than 2 kb. As such, sequence-based prediction of expression in humans is still a critical open challenge, and many, if not all, of the current in vivo expression prediction models cannot predict the effect of sequence alterations on expression levels.

Herein, a modeling framework that predicts gene expression levels ab initio from sequence is described. In some embodiments, the framework integrates a deep-learning method with an optional spatial feature transformation to predict chromatin profile of a biological sample. In some embodiments, the framework includes an L2-regularized linear model to determine gene expression from a wide regulatory region surrounding the gene transcription start site (TSS). In some embodiments, the framework does not use any variant information for training, and instead utilizes sequence context to obtain a local chromatin profile to determine an expression effect for any variant, even variants that are rare or never previously observed.

In several embodiments, models described herein make highly accurate predictions of expression from DNA sequence and prioritize putative causal variants associated with human traits and diseases. Because the models identify causal variants, they outperform traditional genome wide associations studies (GWAS), which merely identify variants associated with a trait.

In addition, models described herein are highly scalable, allowing profiling of over 140 million promoter proximal mutations, in accordance with various embodiments. This enables systematic probing of the impact of gene human transcription dysregulation 'in silico' at a scale not readily achievable experimentally, defining the effects of variants on gene expression. Various embodiments take advantage of the effects of potential mutations on each gene, referred to herein as 'variation potential', which is indicative of the phenotypic impact of expression-altering mutations. Accordingly, in several embodiments, site-directed mutagenesis can be performed to modulate gene expression of one or more genes to achieve a desired expression level.

In several embodiments, various applications can be performed based on a determination of gene expression levels in a biological sample. In many embodiments, biochemical analysis is performed to analyze and or to confirm the determined results of gene expression levels. Accordingly, a biochemical experiment can be performed to determine gene expression and/or chromatin architecture of a biological sample. In some embodiments, genetic material is manipulated to incorporate variants that affect gene expression levels to directly analyze their effects. In some embodiments, genetic sequences having variants that affect expression levels are incorporated into transgene plasmids (e.g., luciferase) to determine their effect on expression level. In some embodiments, CRISPR mutagenesis, Zinc-finger mutagenesis, and/or TALEN mutagenesis is performed on a biological sample to analyze the effects of having a particular sequence on endogenous gene expression. Accordingly, in some embodiments, cell-lines and/or tissues are mutagenized to create biological models to better understand various variants on gene expression. In some embodiments, in vivo tissues are mutagenized to alter sequence variants in order to modulate expression in that tissue.

In some embodiments, preliminary in silico analysis of genetic sequences and various variants within the sequence that can alter gene expression levels are determined utilizing a computational framework capable of determining gene expression levels ab initio from sequence. Based on desired expression levels, designer sequences can be prepared either by polymeric nucleotide synthesis and/or site-directed mutagenesis. In some embodiments, CRISPR mutagenesis, Zinc-finger mutagenesis, and/or TALEN mutagenesis is performed to specifically engineer a sequence that has desired effects on gene expression. Accordingly, in some embodiments, cell-lines and/or tissues, including in vivo and/or ex vivo cells and/or tissues and/or embryonic tissues, are mutagenized to alter sequence variants in order to modulate gene expression levels. In some embodiments, ex vivo or embryonic tissue is transplanted into an individual.

Overview of Gene Expression as Determined by Sequence

A conceptual illustration of a process to determine expression of genes based on its spatial chromatin profile as determined from its sequence in accordance with an embodiment of the invention is illustrated in FIG. 1. In some embodiments, a process is utilized to identify sets of variants that alter gene expression, as determined by their effect on local chromatin profile. Variants and their effects on gene expression can be used in various applications downstream in accordance with a number of embodiments of the invention, including (but not limited to) performing various biochemical assays and diagnosing individuals.

Process 100, in accordance with a number of embodiments, begins with obtaining (101) genetic data from a biological sample. In some embodiments, a biological sample is any collection of eukaryotic cells. In many embodiments, a biological sample is a particular cell-type and/or tissue. In some embodiments, a biological sample has a particular phenotype, such as (for example) a medical disorder (e.g., cancer).

In accordance with various embodiments, genetic data can be derived from a number of sources. In some instances, these genetic data are obtained de novo by extracting the DNA from a biological source and sequencing it. Alternatively, genetic sequence data can be obtained from publicly or privately available databases. Many databases exist that store datasets of sequences from which a user can extract the data to perform experiments upon. In many embodiments, the genetic sequence data include whole or partial genomes; accordingly, any genetic data set as appropriate to the requirements of a given application could be used.

Once genetic data are obtained, process 100 can then determine (103) the spatial chromatin profile along the sequence of the genetic data of the biological sample using a first computational model. In many embodiments, a chromatin profile is a spatial pattern of chromatin regulatory elements along the sequence of a gene, as determined from its sequence ab initio. In some embodiments, the sequence of the biological sample is entered into a trained computational model that is capable of determining a spatial pattern of regulatory elements based on sequence, taking into account single nucleotide variants, insertions, and deletions and the context of the proximal sequence. In some embodiments, a trained computational model determines spatial chromatin profile near the promoter and/or TSS of each gene analyzed.

In several embodiments, the first computational model is trained utilizing chromatin regulatory element profiles, which can be derived experimentally utilizing various epigenetic assays including (but not limited to) chromatin immunoprecipitation sequencing (ChIP-seq), DNAse I hypersensitivity sequencing (DNase-seq), Assay for Transposase-Accessible Chromatin sequencing (ATAC-seq), Formaldehyde-Assisted Isolation of Regulatory Elements (FAIRE-seq), Hi-C capture sequencing, bisulfite sequencing (BS-seq), and methyl array. In some embodiments, chromatin profiles are retrieved from database such as (for example)

Encyclopedia of DNA Elements (ENCODE), NIH Roadmap Epigenomics Mapping Consortium, and the International Human Epigenome Consortium (IHEC). These data sets can yield genomic loci that are important in regulating transcription and/or posttranscriptional processing.

In several embodiments, the computational model is a deep neural network. In some embodiments, the computational model is a convolutional neural network. In some embodiments, a computational model is trained for a particular cell-type and/or tissue and thus utilizes chromatin data derived from that particular cell-type and/or tissue. In some embodiments, a determined chromatin profile is spatially transformed to reduce the complexity of chromatin features along a gene's sequence.

Process 100 determines (105) expression level of genes using a second computational model based on the spatial chromatin profile along the genes within the genetic data of the biological sample. In some embodiments, the expression level of each gene within the genetic data is determined. In some embodiments, the second computational model is trained using expression data sets with determined chromatin profiles. In a number of embodiments, the second computational model is an L2 linearized regression model.

In several embodiments, processes to determine expression levels of genes in a biological sample is utilized in various downstream applications, including (but not limited to) biochemical assays, diagnosis of an individual, and/or treatment of an individual. These embodiments are described in greater detail in subsequent sections.

Processes to Yield Chromatin Profiles and Gene Expression Based on Genetic Code

Figure 2:
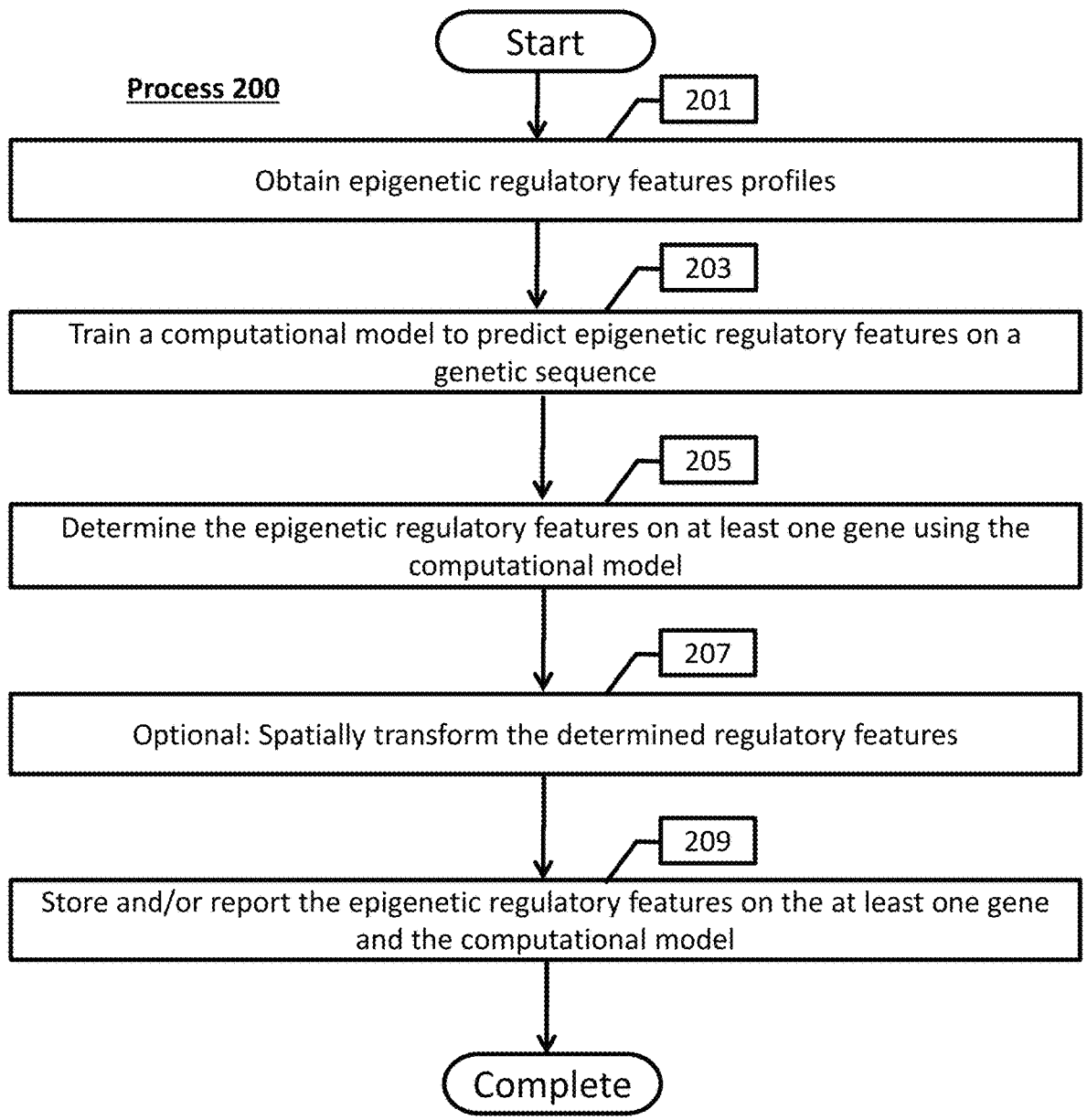
FIG. 2 provides a process to train a computational model to determine epigenetic regulatory features in accordance with an embodiment of the invention.

A conceptual illustration of a process to determine epigenetic regulatory features on at least one gene utilizing computing systems is provided in FIG. 2. As shown, in a number of embodiments, the process can begin with by obtaining (201) epigenetic regulatory features profiles (i.e., chromatin profiles). An epigenetic regulatory features profile is a collection of data indicating where various factors and elements that affect transcription interact with DNA along a genomic sequence. In many embodiments, epigenetic regulatory features are cell-type and/or tissue specific and include (but are not limited to) sites of chromatin accessibility (e.g., DNase I hypersensitivity), chromatin marks (e.g., histone code), transcription factor binding sites, and other epigenetic factors. An example of 2,002 epigenetic regulatory features is described in the Exemplary Embodiments section.

Generally, epigenetic regulatory features profiles can be determined utilizing various epigenetic assays including (but not limited to) chromatin immunoprecipitation sequencing (ChIP-seq), DNAse I hypersensitivity sequencing (DNase-seq), Assay for Transposase-Accessible Chromatin sequencing (ATAC-seq), Formaldehyde-Assisted Isolation of Regulatory Elements (FAIRE-seq), Hi-C capture sequencing, bisulfite sequencing (BS-seq), and methyl array. Several databases store chromatin and RBP/RNA-element profiles which can be used, including (but not limited to) Encyclopedia of DNA Elements (ENCODE), NIH Roadmap Epigenomics Mapping Consortium, and the International Human Epigenome Consortium (IHEC).

Utilizing epigenetic regulatory features profiles as input training data, a computational model is trained (203) to predict epigenetic regulatory features on a genetic sequence. In several embodiments, the computational model is a deep neural network. In some embodiments, the computational model is a convolutional neural network. In some embodiments, a computational model is trained for a particular cell-type and/or tissue and thus utilizes chromatin data derived from that particular cell-type and/or tissue.

Process 200 determines (205) the epigenetic regulatory features on at least one gene using the computational model. In several embodiments, epigenetic regulatory features are determined on large sets of genes, including all Pol II transcribed genes of a whole organismal genome. In some embodiments, for each gene that is analyzed, epigenetic regulatory features are determined in relation to a sequence structure of the gene, such as (for example) the TSS, known promoter region, or similar. In some embodiments, epigenetic features are determined for some distance upstream and/or downstream from a gene sequence structure, such as (for example) 20 kilobases (kb) upstream and downstream of the genes TSS. It should be understood that the length of sequence for which epigenetic features are determined in relation to a gene sequence structure can vary and does not have to be equal upstream and downstream. In some embodiments, epigenetic features are determined 1 kb, 2 kb, 3 kb, 4, kb, 5 kb, 7.5 kb, 10 kb, 15 kb, 20 kb, 25 kb, or 50 kb upstream of a gene sequence structure. Similarly, in some embodiments, epigenetic features are determined 1 kb, 2 kb, 3 kb, 4, kb, 5 kb, 7.5 kb, 10 kb, 15 kb, 20 kb, 25 kb, or 50 kb downstream of a gene sequence structure. It should be further noted that epigenetic features can be determined on any sequence that would affect gene expression and doesn't have to be in relation to the TSS.

In some embodiments, determination of epigenetic features along a sequence is binned to shorter sequence lengths. For example, if epigenetic features are to be determined for 20 kb upstream and downstream the TSS of a gene, the determination of epigenetic features can be performed in increments such as (for example) 200 bp bins and thus totaling 200 non-overlapping bins for the entire 40 kb sequence considered. In some embodiments, 50 bp, 100 bp, 150 bp, 200 bp, 250 bp, 300 bp, 400 bp, or 500 bp are utilized to determine epigenetic features along a sequence. In some embodiments, bins are overlapped, which may help gain better resolution.

In some embodiments, determination of epigenetic features within a bin also considers surrounding sequence context, which may better provide context of the local epigenetic architecture of the binned sequence. For example, when determining epigenetic features of a 200 bp bin, the surrounding 1800 bp (900 upstream and 900 downstream) can be considered, resulting in 2000 bp considered for each 200 bp bin (i.e., 10× more sequence considered per bin). In some embodiments, 1×, 2×, 3×, 5×, 7.5×, 10×, 15×, 20×, or 30× of surrounding sequence is considered to determine epigenetic factors for each bin.

Process 200 optionally spatially transforms (207) the determined regulatory features, which may reduce the dimensionality of the spatial chromatin regulatory features due to sequential binning along the sequence. In some embodiments, a spatial transformation module is utilized. In some embodiments, a spatial transformation model is an exponential decay function. In some embodiments, spatial transformation put weights on bins utilized to determine epigenetic features, and the weights can be determined as appropriate. In some embodiments, bins closer to a selected gene structure (e.g., TSS) are weighted greater than bins further away to the selected gene structure. It should be understood that bins upstream from a selected gene structure may be weighted differently than bins downstream, as appropriate to the task at hand. For example, 2,000 epigenetic features can be determined for a 40 kb sequence (e.g., 20 kb upstream and 20 kb downstream a TSS) of a nearby gene in 200 bp bins (i.e., 200 total bins), resulting in 400,000 epigenetic features for the nearby single gene. Reducing the epigenetic features 20-fold to 20,000 features may be beneficial, as determined by application.

In accordance with several embodiments, epigenetic regulatory features on the at least one gene and the computational models are stored and/or reported (211). In some embodiments, these profiles and regulatory effects may be used in many further downstream applications, including (but not limited to) determining gene expression of the genes analyzed.

While a specific example of a process for determining genetic regulatory features on at least one gene is described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

Figure 3:
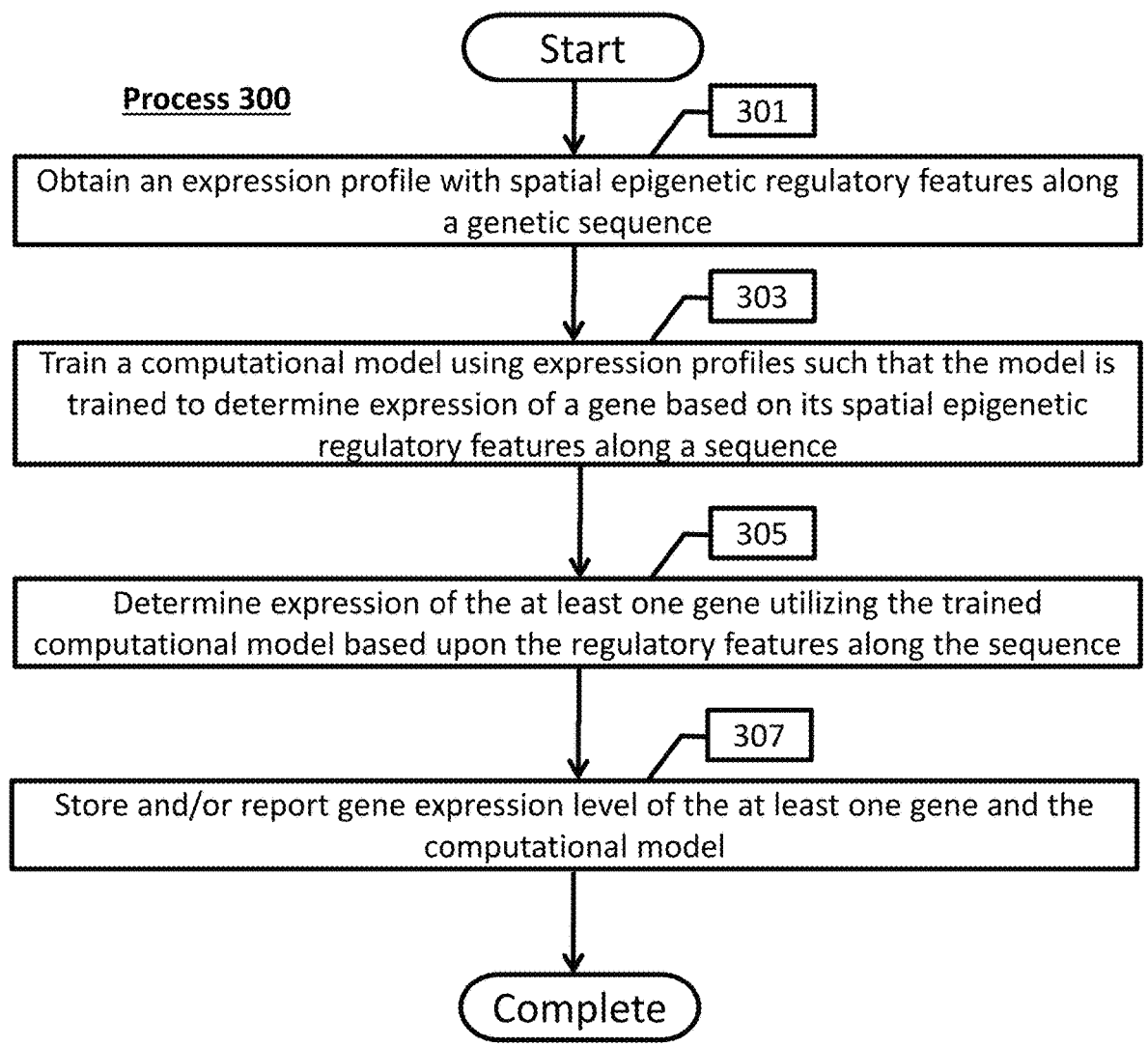
FIG. 3 provides a process to train a computational model to determine expression of at least one gene in accordance with an embodiment of the invention.

Depicted in FIG. 3 is a conceptual illustration of a process to determine expression level of at least one gene using a computational model, which can performed on various computing systems. The process utilizes the regulatory features along the sequence of the gene to determine its expression. It should be understood that this process can determine the expression of a number of genes when using computing systems, including every Pol II transcribed gene in an organismal genome.

Process 300 can begin with obtaining (301) an expression profile with spatial epigenetic regulatory features along genetic sequence. In several embodiments, an expression profile is a profile of expression levels of a set of genes. In many embodiments, the set of genes utilized in an expression profile is a comprehensive set, such as all Pol transcribed genes in an organismal genome (i.e., transcriptome). In some embodiments, an expression profile has an associated biological attribute, such as cell-type, tissue origin, and/or phenotype (e.g., pathway activation or a particular disorder pathology).

The expression profile with spatial epigenetic features is used to train (303) a computational model to be able to determine expression of a gene based on its spatial epigenetic regulatory features along a sequence. In several embodiments, a computational model is trained utilizing expression profiles that have an associated biological attribute such that the model is capable of predicting expression of biological samples sharing the biological attribute. For example, if liver tissue expression data sets are used to train a computational model, then expression of a gene in liver tissue can be determined from the gene's epigenetic features utilizing the trained computational model.

In many embodiments, a linear regression model is used. In some instances, a linear regression model is L2 regularized and trained using an appropriate package, such as (for example) the xgboost package. In some embodiments, predicted probabilities are z-transformed to have a particular mean and standard deviation.

In a number of embodiments, epigenetic regulatory features are spaced along a genetic sequence. Epigenetic regulatory features are various factors and elements that affect transcription interact with DNA along a genomic sequence. In many embodiments, epigenetic regulatory features are cell-type and/or tissue specific and include (but are not limited to) sites of chromatin accessibility (e.g., DNase I hypersensitivity), chromatin marks (e.g., histone code), transcription factor binding sites, and other epigenetic factors. An example of 2,002 epigenetic regulatory features is described in the Exemplary Embodiments section. In some instances, epigenetic regulatory variants and their spacing along a gene are determined in accordance with Process 200 described herein.

In some embodiments, for each gene that is used for training and/or analyzed, epigenetic regulatory features are spaced in relation to a sequence structure of the gene, such as (for example) the TSS, known promoter region, or similar. In some embodiments, epigenetic features are spaced some distance upstream and/or downstream from a gene sequence structure, such as (for example) 20 kilobases (kb) upstream and downstream of the genes TSS. It should be understood that the length of sequence for which epigenetic features are spaced in relation to a gene sequence structure can vary and does not have to be equal upstream and downstream. In some embodiments, epigenetic features are spaced along 1 kb, 2 kb, 3 kb, 4, kb, 5 kb, 7.5 kb, 10 kb, 15 kb, 20 kb, 25 kb, or 50 kb upstream of a gene sequence structure. Similarly, in some embodiments, epigenetic features are spaced along 1 kb, 2 kb, 3 kb, 4, kb, 5 kb, 7.5 kb, 10 kb, 15 kb, 20 kb, 25 kb, or 50 kb downstream of a gene sequence structure. It should be further noted that epigenetic features are spaced along any sequence that would affect gene expression and doesn't have to be in relation to the TSS.

In some embodiments, epigenetic features along a sequence are binned within shorter sequence lengths. For example, if epigenetic features are spaced along 20 kb upstream and downstream the TSS of a gene, the determination of epigenetic features can be performed in increments such as (for example) 200 bp bins and thus totaling 200 non-overlapping bins for the entire 40 kb sequence considered. In some embodiments, 50 bp, 100 bp, 150 bp, 200 bp, 250 bp, 300 bp, 400 bp, or 500 bp are utilized to bin epigenetic features along a sequence. In some embodiments, bins are overlapped, which may help gain better resolution.

In some embodiments, epigenetic features within a bin were determined considering surrounding sequence context, which may better provide context of the local epigenetic architecture of the binned sequence. For example, when determining epigenetic features of a 200 bp bin, the surrounding 1800 bp (900 upstream and 900 downstream) can be considered, resulting in 2000 bp considered for each 200 bp bin (i.e., 10× more sequence considered per bin). In some embodiments, 1×, 2×, 3×, 5×, 7.5×, 10×, 15×, 20×, or 30× of surrounding sequence were considered to determine epigenetic factors for each bin.

In some embodiments, regulatory features are spatially transformed, which may reduce the number of features to be used in the trained computational model. In some embodiments, bins closer to a selected gene structure (e.g., TSS) are weighted greater than bins further away to the selected gene structure. It should be understood that bins upstream from a selected gene structure may be weighted differently than bins downstream, as appropriate to the task at hand.

Utilizing the trained computational model of Step 303, the expression of at least one gene is determined (305) based upon the regulatory features along a sequence examined. Any appropriate sequence in which epigenetic features have been determined along the genetic sequence of a gene can be entered into the training model to determine the gene's expression level. In some embodiments, a genetic sequence to be examined is leave out data from the training set. In some embodiments, a genetic sequence to be examined is derived from a biological sample unaffiliated with the training data. In some embodiments, the genetic sequence to be examined shares a biological attribute with the expression sets used to train the model. In some embodiments, a biological attribute is a cell-type, tissue origin, and/or phenotype (e.g., pathway activation or a particular disorder pathology).

The determined expression level of the at least one gene and the computational model are stored and/or reported (307). In a number of embodiments, gene expression levels and/or computational models are used in a number of downstream applications, including (but not limited to) clinical classification of biological tissue (e.g., clinical diagnostics), further molecular research into gene expression level including evolutionary, and site-directed.

While a specific example of a process for determining expression levels of at least one gene is described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

Processes to Determine Gene Expression of a Biological Sample

Figure 4:
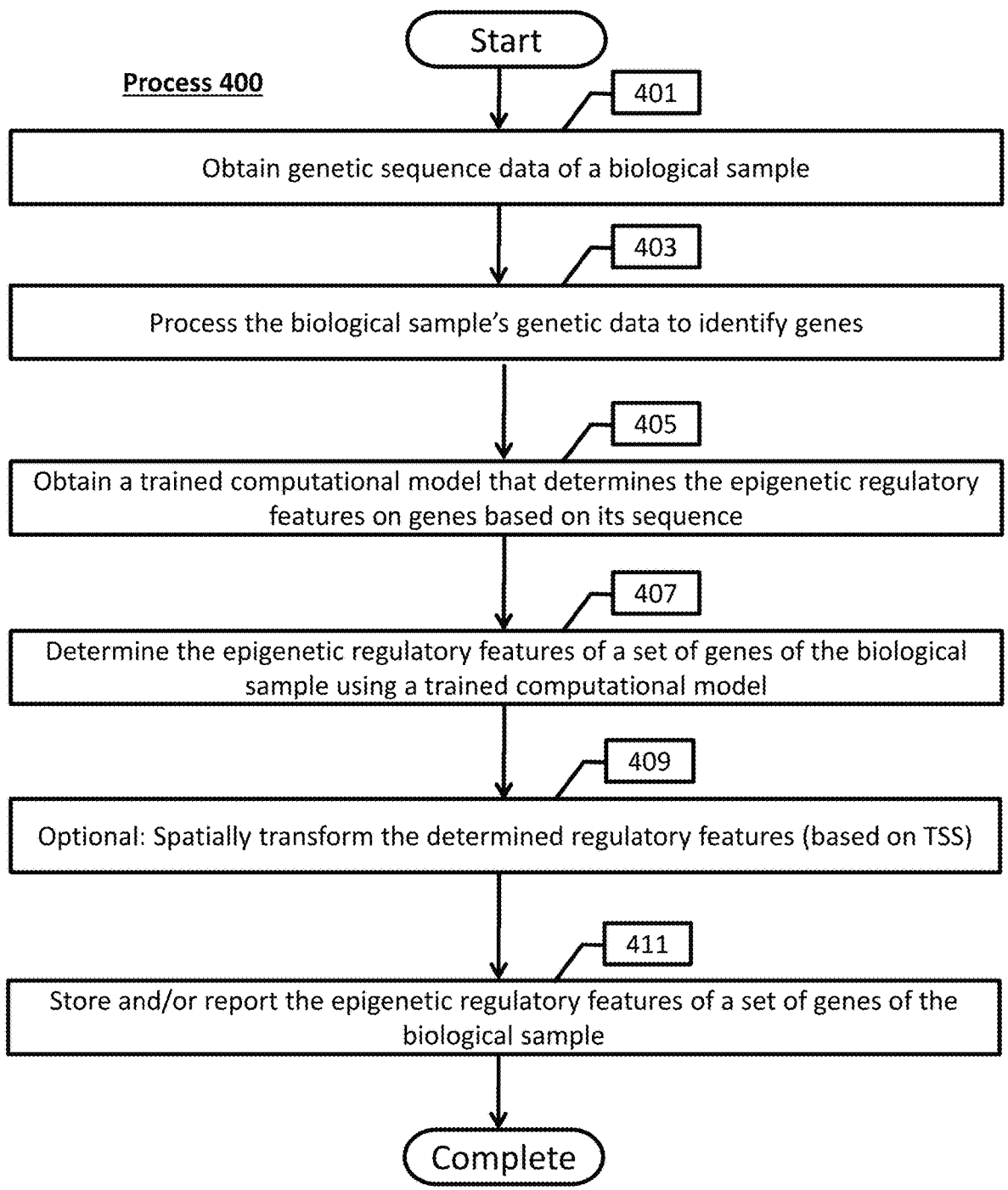
FIG. 4 provides a process to determine epigenetic regulatory features of a biological sample in accordance with an embodiment of the invention.

FIG. 4 provides a conceptual illustration of a process to determine the epigenetic regulatory features of a set of genes of a biological sample a via computer systems using the biological sample's genetic sequence data and a trained computational model. As shown in FIG. 4, Process 400 obtains (401) genetic sequence data of a biological sample. The data, in accordance with many embodiments, is any DNA sequence data of a biological that is inclusive of gene sequence regions to be analyzed. In some embodiments, genetic data is a whole genome, a partial genome, or other data that is directed towards the genes to be analyzed. In some embodiments, genetic data is only sequencing data on a set of regions having effects on expression of genes to be analyzed (e.g., capture sequencing). In some embodiments, genetic material is extracted from the biological sample and sequenced in accordance with various protocols known in the art.

In many embodiments, biological samples are derived from a biopsy of an individual. In particular embodiments, the DNA to be acquired can be derived from biopsies of human patients associated with a phenotype or a disease state and derived from unaffected individuals as well. In some embodiments, DNA can be derived from common research sources, such as in vitro tissue culture cell lines or research mouse models. In some embodiments, a biological sample is any collection of eukaryotic cells in which epigenetic regulatory features of a set of genes is to be determined.

In accordance with various embodiments, a biological sample's genetic sequence data are processed (403) to identify genes to be analyzed. In many embodiments, particular sequence structures such as a gene's TSS and/or promoter are identified for epigenetic regulatory feature analysis.

A trained computational model capable of determining the epigenetic regulatory features on genes based on its sequence is also obtained (405). In some embodiments, a trained classification model is trained as shown and described in FIG. 2, however, in accordance with more embodiments, any classification model capable of determining the epigenetic regulatory features on genes based on its sequence may be used. In a number of embodiments, genetic sequence data of a biological sample are entered into a computational model, wherein subsequently the epigenetic regulatory features of the biological sample's genes are determined (407). In addition, process 400 optionally spatially transforms the determined epigenetic regulatory features, which may reduce the dimensionality of the spatial epigenetic regulatory features.

The epigenetic regulatory features of a set of genes of the biological sample are reported and/or stored (409). In numerous embodiments, the epigenetic regulatory features can be used in a number of downstream applications, which may include (but is not limited to) determining expression levels of the set of genes.

While a specific example of a process for determining the epigenetic regulatory features of a set of genes of a biological sample is described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

Figure 5:
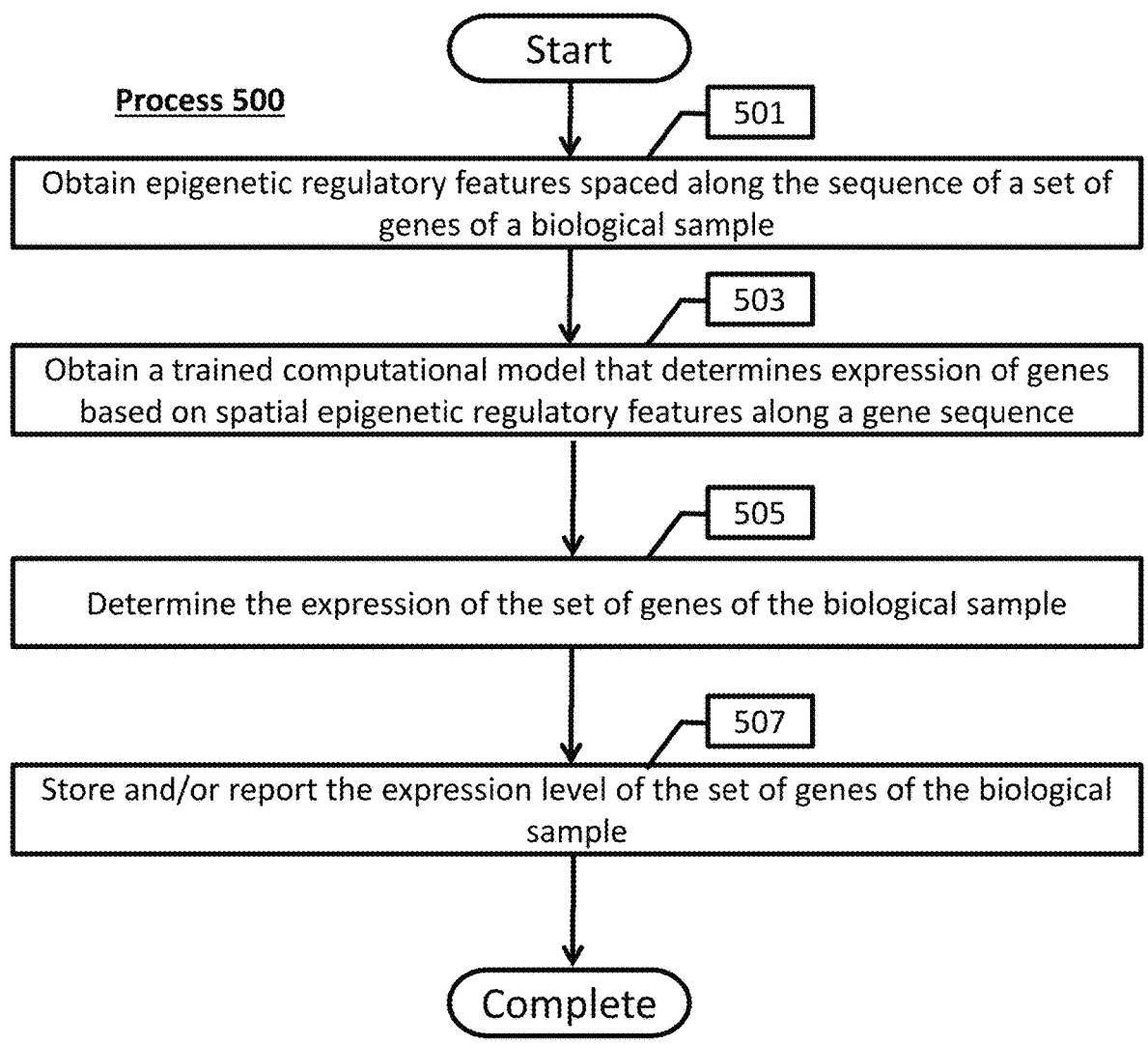
FIG. 5 provides a process to determine expression of a set of genes of a biological sample in accordance with an embodiment of the invention.

FIG. 5 provides a conceptual illustration of a process to determine the expression of a set of genes of a biological sample via computer systems using a trained computational model. Various embodiments utilize this process to determine expression levels of genes within a particular tissue within an individual. As shown in FIG. 5, epigenetic regulatory features spaced along the sequence of a set of genes of a biological sample are obtained (501). Epigenetic regulatory features are various factors and elements that affect transcription interact with DNA along a genomic sequence. In many embodiments, epigenetic regulatory features are cell-type and/or tissue specific and include (but are not limited to) sites of chromatin accessibility (e.g., DNase I hypersensitivity), chromatin marks (e.g., histone code), transcription factor binding sites, and other epigenetic factors. An example of 2,002 epigenetic regulatory features is described in the Exemplary Embodiments section. In some instances, epigenetic regulatory variants and their spacing along a gene are determined in accordance with Process 400 described herein. It should be noted however, that any appropriate epigenetic regulatory features and any appropriate method to determine epigenetic regulatory features may be used within various embodiments.

A trained computational model capable of determining expression of genes based on spatial epigenetic regulatory features along a gene sequence is also obtained (503). In some embodiments, a trained computational model is trained as shown and described in FIG. 3, however, in accordance with more embodiments, any computational model capable of determining gene expression levels based on a biological sample's spatial epigenetic regulatory features may be used. In some embodiments, the obtained computational model has been trained using expression sets having a particular biological attribute that is shared with the biological sample. In some embodiments, the biological attribute is a cell-type, tissue origin, and/or phenotype. In a number of embodiments, epigenetic regulatory features are entered into a computational model, wherein subsequently the expression of the set of genes of the biological sample are determined (505). In some embodiments, gene expression levels are determined for every Pol II transcribed gene within the genome of the biological sample.

Expression level of the set of gene of the biological sample are stored and/or reported (507). In a number of embodiments, gene expression are used in a number of downstream applications, including (but not limited to) biochemical assays, diagnoses and treatments of patients.

While a specific example of a process for determining expression levels of a set of genes is described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications.

Systems of Genetic Sequence Analysis

Figure 6:
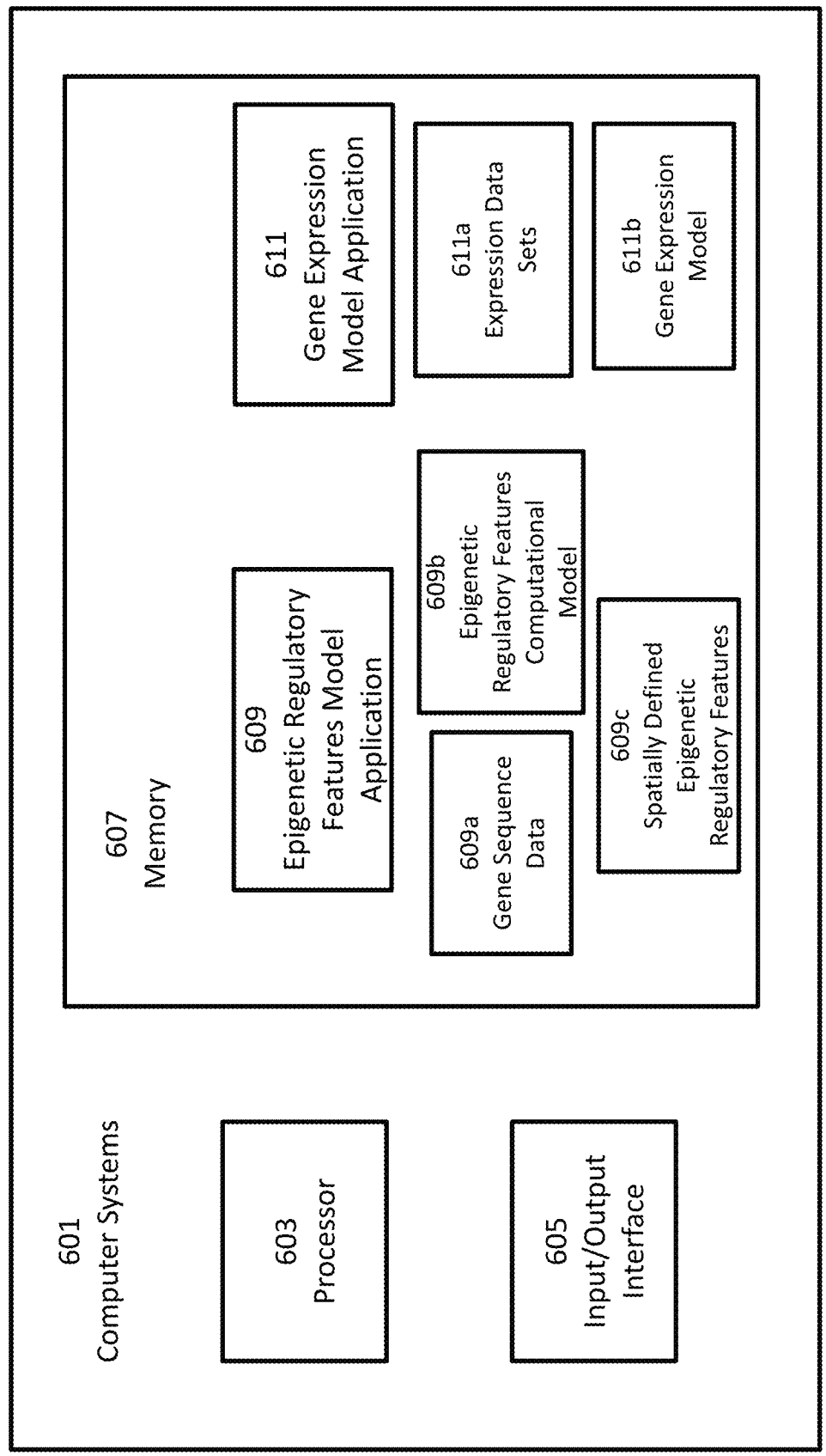
FIG. 6 provides an illustration of computer systems for various applications in accordance with various embodiments of the invention.

Turning now to FIG. 6, computer systems (601) may be implemented on computing devices in accordance with some embodiments of the invention. The computer systems (601) may include personal computers, a laptop computers, other computing devices, or any combination of devices and computers with sufficient processing power for the processes described herein. The computer systems (601) include a processor (603), which may refer to one or more devices within the computing devices that can be configured to perform computations via machine readable instructions stored within a memory (607) of the computer systems (601). The processor may include one or more microprocessors (CPUs), one or more graphics processing units (GPUs), and/or one or more digital signal processors (DSPs). According to other embodiments of the invention, the computer system may be implemented on multiple computers.

In a number of embodiments of the invention, the memory (607) may contain an epigenetic regulatory model application (609) and a gene expression model application (611) that performs all or a portion of various methods according to different embodiments of the invention described throughout the present application. As an example, processor (603) may perform ab initio gene expression determination methods similar to any of the processes described above with reference to FIGS. 2 through 5, which involve the use of various applications such as an epigenetic regulatory model application (609) and a gene expression model application (611), during which memory (607) may be used to store various intermediate processing data such as gene sequence data (609a), epigenetic regulatory features computational model (609b), spatially defined epigenetic regulatory features (609c), expression data sets (611a), and gene expression model (611b).

In some embodiments of the invention, computer systems (601) may include an input/output interface (605) that can be utilized to communicate with a variety of devices, including but not limited to other computing systems, a projector, and/or other display devices. As can be readily appreciated, a variety of software architectures can be utilized to implement a computer system as appropriate to the requirements of specific applications in accordance with various embodiments of the invention.

Although computer systems and processes for variant analyses and performing actions based thereon are described above with respect to FIG. 6, any of a variety of devices and processes for data associated with variant analyses as appropriate to the requirements of a specific application can be utilized in accordance with many embodiments of the invention.

Biochemical Analysis and Site-Directed Mutagenesis

A number of embodiments are directed towards biochemical assays to be performed based on the results of variants identified to affect gene expression levels. Accordingly, in several embodiments, computational methods are performed to determine epigenetic regulatory features based on sequence and the effect on gene expression, and based on those determinations a biochemical assay is performed to assess gene expression. In some embodiments, determination of epigenetic regulatory features based on sequence and the effect on gene expression by performing methods described in FIGS. 2 to 5. It should be noted, however, that any method capable of determining epigenetic regulatory features based on sequence and the effect on gene expression can be utilized within various embodiments.

In many embodiments, biochemical methods are performed as follows:
a) obtain a sequence data of a biological sample
b) determine epigenetic regulatory features based on sequence and the effect on gene expression
c) based epigenetic regulatory features and the effect on gene expression, perform a biochemical assay to assess gene expression or cell function.

In some embodiments, determination of epigenetic regulatory features based on sequence and the effect on gene expression can be performed in accordance as described herein, such as the methods described in FIGS. 2 to 5.

A number of biochemical assays can be performed on the basis of the determination of epigenetic regulatory features and the effect on gene expression. Generally, biochemical assays will provide a more in depth assessment of variant and how it affects various biological functions, which include effects on chromatin formation, chromatin binding, nearby gene transcription, RNA stability, RNA processing, translation, cellular function, and disorder pathology. A number of biochemical assays are known in the art to assess local gene sequence (especially variants and indels within sequence) effect, including (but not limited to) chromatin immunoprecipitation sequencing (ChIP-seq), DNAse I hypersensitivity sequencing (DNase-seq), Assay for Transposase-Accessible Chromatin sequencing (ATAC-seq), Formaldehyde-Assisted Isolation of Regulatory Elements (FAIRE-seq), Hi-C capture sequencing, bisulfite sequencing (BS-seq), methyl array, transgene expression analysis (e.g., luciferase and eGFP), qPCR, RNA hybridization (e.g., ISH), cross-linking immunoprecipitation sequencing (CLIP-seq), RNA immunoprecipitation sequencing (RIP-seq), RNA-seq, western blot, immunodetection, flow cytometry, enzyme-linked immunosorbent assay (ELISA), and mass spectrometry.

Several embodiments are also directed towards manipulating genetic material in order to analyze variants, especially site-directed mutagenesis. In some embodiments, variants, including single nucleotide variants, insertions, and/or deletions, are incorporated into a DNA sequence construct for analysis (e.g., luciferase plasmid construct). In some embodiments, variants are introduced into at least one allele of the DNA of a biological cell. Several methods are well known to introduce variant mutations within an allele, including (but not limited to) CRISPR mutagenesis, Zinc-finger mutagenesis, and TALEN mutagenesis. In some embodiments, a common variant is changed into rare variant. In some embodiments, a rare variant is changed into a common variant, especially when determining the effect of "correcting" a potential gene expression altering variant.

Various embodiments are directed towards development of cell lines having a particular DNA sequences that have variants affecting gene expression levels. In some embodiments, a cell line can be manipulated by genetic engineering to harbor a set of variants. In some embodiments, a cell line can be derived from an individual (e.g., from a biopsy) which would harbor the variants identified in that individual. In some embodiments, a cell line from an individual can be genetically manipulated to "correct" a set of expression altering variants. In some embodiments, a cell line having a set expression altering variants and a cell line having a set of control or "corrected" variants may be assessed to determine the cumulative effect of the set of variants, especially when modeling a medical disorder that is associated with the set of expression altering variants.

A number of embodiments are directed to a preliminary in silico analysis of variants that can affect gene expression in order to perform site-directed mutagenesis that modulates gene expression levels. Accordingly, utilizing computational models that can predict gene expression levels ab initio from sequence, a number of hypothetical variants can be designed that increase and/or decrease gene expression as desired. Cis-manipulation of gene expression by local mutagenesis can be a useful tool to understand a number of phenotypes that are based on stoichiometric levels of gene expression. In addition, a number of medical disorders are known to arise from improper gene expression stoichiometry (e.g., see A. M. Rice and A McLysaght *BMC Biol.* 15, 78 (2017), the disclosure of which is incorporated herein by reference).

In several embodiments, gene expression stoichiometry methods are performed as follows:
   (a) perform in silico analysis utilizing computational models to determine variant effects on gene expression
   (b) based on in silico analysis, perform site-directed mutagenesis on at least one gene such that its altered sequence is predicted to alter gene expression levels (c) perform biochemical analysis to determine effect of variant on gene expression.

In some embodiments, in silico analysis to determine effect of variants on gene expression can be performed in accordance as described herein, such as the methods described in FIGS. 2 to 5. In some embodiments, site-directed mutagenesis is performed utilizing CRISPR mutagenesis, Zinc-finger mutagenesis, and/or TALEN mutagenesis. In some embodiments, biochemical analysis to be performed is at least one of:) chromatin immunoprecipitation sequencing (ChIP-seq), DNAse I hypersensitivity sequencing (DNase-seq), Assay for Transposase-Accessible Chromatin sequencing (ATAC-seq), Formaldehyde-Assisted Isolation of Regulatory Elements (FAIRE-seq), Hi-C capture sequencing, bisulfite sequencing (BS-seq), methyl array, transgene expression analysis (e.g., luciferase and eGFP), qPCR, RNA hybridization (e.g., ISH), cross-linking immunoprecipitation sequencing (CLIP-seq), RNA immunoprecipitation sequencing (RIP-seq), RNA-seq, western blot, immunodetection, flow cytometry, enzyme-linked immunosorbent assay (ELISA), and mass spectrometry.

In some embodiments, isolated cells and/or tissues, including in vivo and/or ex vivo cells and/or tissues, are mutagenized to alter sequence variants in order to modulate gene expression levels. Accordingly, cells and/or tissues are designed to have altered gene expression levels that may be useful for either understanding the consequence of expression levels and/or correcting expression levels. In some embodiments, a biopsy is extracted from an individual and alterations to the genetic sequence are introduced to modulate gene expression. In some embodiments, an extracted biopsy with modulated gene expression is transplanted back into an individual such that the modified ex vivo tissue can provide a therapeutic benefit to the individual by the altered gene expression.

Diagnostics and Treatments of Diseases Based on Gene Expression

Various embodiments are directed to development of treatments related to diagnoses of individuals based on their gene expression data. As described herein, an individual may be diagnosed as having a particular gene expression status in relation to a disease. In some embodiments, an individual is diagnosed as having a disorder or having a high propensity for a disorder. Based on the gene expression data, an individual can be treated with various medications and therapeutic regimens.

Diagnostic Methods

A number of embodiments are directed towards diagnosing individuals by determining the effect of variants on gene expression. In a number of embodiments, diagnostics can be performed as follows:
   a) obtain genetic data of the individual to be diagnosed
   b) determine effect of variants on gene expression related to a medical disorder
   c) diagnose the individual based on the gene expression levels.

Diagnoses, in accordance with various embodiments, can be performed as portrayed and described in any one of FIG. 4 or 5.

Many embodiments of diagnostics improve on traditional diagnostic methods. Because the genetic contribution to gene expression is difficult to determine from genetic sequence, traditional genetic tests of examining a single gene, variant, and/or locus have been unavailable. As described herein, however, in some embodiments, a diagnosis is performed ab initio utilizing genetic sequence to determine gene expression levels, such as described in FIGS. 2 to 5. In some embodiments, diagnoses are performed for disorders in which GWAS does not identify causal variants. In some embodiments, diagnoses are performed for disorders that arise at least in part by variants that affect gene expression levels.

Diagnostic Kits

Embodiments are directed towards expression analysis (e.g., RT-PCR, microarray) genomic loci sequencing and/or single nucleotide polymorphism (SNP) array kits to be utilized within various methods as described herein. As described, various methods can diagnose an individual for a medical disorder by examining variants that affect gene expression or the expression levels directly. Accordingly, a number of embodiments are directed towards genomic loci sequencing and SNP array kits that cover a set of genomic loci to diagnose a particular trait. In some instances, the set of genomic loci are identified by a computational model, such as one described in FIG. 2 and FIG. 3. In addition, various embodiments are directed towards expression analysis kits that cover a set of genes to diagnose a particular trait.

A number of targeted gene sequencing protocols can be utilized, including (but not limited to) partial genome sequencing, primer-directed sequencing, and capture sequencing. Generally, targeted sequencing involves selection step either by hybridization and/or amplification of the target sequences prior to sequencing. Therefore, embodiments are directed to sequencing kits that target genomic loci that are known to harbor variants that affect expression levels to diagnose a particular medical disorder.

Likewise, a number of SNP array protocols can be utilized. In general, chip arrays are set with oligo sequences having a particular SNP. Sample DNA derived from an individual can be processed and then applied to SNP array to determine sites of hybridization, indicating existence of a particular SNP. Thus, embodiments are directed to SNP array kits that target particular SNPs that known to be expression altering in order to diagnose a particular medical disorder.

The number of genomic loci and/or SNPs to include in a sequencing kit can vary, depending on the genomic loci and/or SNPs to examine for a particular trait and the computational model to be used. In some embodiments, the genomic loci and/or SNPs to be examined are identified by a computational model, such as the computational model described in FIG. 2 and FIG. 3. In various embodiments, the number of genomic loci in a sequencing kit are approximately, 100, 1000, 5000, 10000, 20000, 30000, 40000, 50000, 60000, 70000, 80000, 90000, 100000, 150000, or 200000 loci. In various embodiments, the number of SNPs in an array kit are approximately, 1000, 10000, 50000, 100000, 200000, 300000, 400000, 500000, 600000, 700000, 800000, 900000, 1000000, 1500000, or 2000000 SNPs. In some embodiments, all identified loci are included in a kit. In some embodiments, only a subset of the loci are included. It should be understood that precise number and positions of loci can vary as the gene expression model can be updated with new data or recreated with a different data set (especially for biological attributes).

The number of probes or primer pairs to include in an expression analysis kit can vary, depending on the genes to examine for a particular trait and the computational model to be used. In some embodiments, the genes to be examined are identified by a computational model, such as the computational model described in FIG. 2 and FIG. 3. In various embodiments, the number of genes to analyze in an expression kit are approximately, 10, 20, 30, 40, 50, 100, 200, 300, 400, 500, 1000, 5000, or 10000 genes. Generally the probes and/or primer pairs to be included in a kit are directed to cDNA and thus span exon-exon junctions. In some embodiments, all identified genes are included in a kit. In some embodiments, only a subset of the genes are included. It should be understood that precise number genes can vary as the gene expression model can be updated with new data or recreated with a different data set (especially for biological attributes).

Medications and Supplements

Several embodiments are directed to the use of medications and/or dietary supplements to treat an individual based on their medical disorder diagnosis. In some embodiments, medications and/or dietary supplements are administered in a therapeutically effective amount as part of a course of treatment. As used in this context, to "treat" means to ameliorate at least one symptom of the disorder to be treated or to provide a beneficial physiological effect.

A therapeutically effective amount can be an amount sufficient to prevent reduce, ameliorate or eliminate symptoms of disorders or pathological conditions susceptible to such treatment. In some embodiments, a therapeutically effective amount is an amount sufficient to reduce the symptoms of a medical disorder.

Dosage, toxicity and therapeutic efficacy of the compounds can be determined, e.g., by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to other tissue and organs and, thereby, reduce side effects.

Data obtained from cell culture assays or animal studies can be used in formulating a range of dosage for use in humans. If the pharmaceutical is provided systemically, the dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration or within the local environment to be treated in a range that includes the $IC_{50}$ (i.e., the concentration of the test compound that achieves a half-maximal inhibition) as determined in cell culture. Such information can be used to more accurately determine useful doses in humans. Levels in plasma may be measured, for example, by liquid chromatography coupled to mass spectrometry.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments. For example, several divided doses may be administered daily, one dose, or cyclic administration of the compounds to achieve the desired therapeutic result.

Alterations in Dosing Based on Metabolism

A number of embodiments are directed towards altering treatments of individuals based on their variants that affect expression of genes involved with drug metabolism. In some embodiments, a model is trained to identify loci harboring variants that affect expression of drug metabolizing genes. In some embodiments, genomic loci known to harbor variants that alter gene expression are associated with a drug metabolism. In some embodiments, the effect of variants within a sequence on gene expression is determined using a computational model. Based on results, in some embodiments, dosing can be altered (i.e., high metabolizers are dosed higher and low metabolizers are dosed lower).

Several medications are known to be metabolized differently by individuals based on the expression of a few key genes. Table 1 is a list of medication and genes that are involved with metabolism of that medication. Medications and genes involved in their metabolism can also be found using the PharmGKB database. Accordingly, based on methods described herein that determine alterations biochemical regulation, especially in transcriptional and/or posttranscriptional regulation, an individual can be treated accordingly. For example, the gene CYP2D6 is involved in the metabolism of oxycodone. If an individual is found to have variants that decrease the expression of CYP2D6, then lower doses of oxycodone (or an alternative medication) can be administered. If an individual is found to have regulatory variants that increase the expression of CYP2D6, then higher doses of oxycodone (or an alternative medication) can be administered. In some embodiments, the effects of variants on gene expression is determined by performing methods described in FIGS. 2 to 5. It should be noted, however, that any method capable of determining the effect of variants on gene expression levels can be utilized within various embodiments.

In many embodiments, dosing alteration methods are performed as follows:
a) obtain a set of variants of an individual
b) determine the effect of variants on gene expression levels
c) based on the effect of variants on gene expression levels, determine the ability of an individual to metabolize a medication
d) based on metabolism results, administer an appropriate dose of the medication or administer an alternative medication.

In some embodiments, determination of the effect of variants on gene expression levels can be performed in accordance with the description accompanying FIGS. 2 to 5.

EXEMPLARY EMBODIMENTS

Bioinformatic and biological data support the methods and systems of determining the contribution of variants on transcriptional expression levels and applications thereof. In the ensuing sections, exemplary computational methods and exemplary applications related to gene expression determinations are provided, especially in the context of immune-related diseases. Exemplary methods and applications can also be found in the publication "Deep learning sequence-based ab initio prediction of variant effects on expression and disease risk" of J. Zhou, et al., Nat. Genet. 50(8), 1171-1179 (2018), the disclosure of which, including all supplemental text, tables and data, is incorporated herein by reference.

Deep Learning Sequence-Based ab initio Prediction of Variant Effects on Expression and Disease Risk A computational framework for quantitatively assessing the impact of sequence variants on gene expression in the context of human disease is described in the following sections. In particular, a tissue-specific modeling framework ExPecto is described, which predicts gene expression levels ab initio from sequence for over 200 tissues and cell types. The ExPecto framework integrates a deep-learning method with spatial feature transformation and L2-regularized linear models to predict tissue-specific expression from a wide regulatory region of 40 kb promoter-proximal sequences. A prominent feature of this framework is that it does not use any variant information for training, enabling prediction of expression effect for any variant, even variants that are rare or never previously observed. This approach is general and can be applied to comprehend contributions of mutations to many medical disorders and phenotypes, which in turn can contribute to development of diagnostic tests, performing diagnoses, and treating individuals.

The resulting ExPecto models make highly accurate cell-type-specific predictions of expression from DNA sequence, as evaluated with known expression quantitative trait loci (eQTLs) and validated causal variants from a massively parallel reporter assay. With this capability, putative causal variants associated with human traits and diseases was prioritized from hundreds of publicly available genome-wide association studies (GWAS). Newly predicted putative causal variants for Crohn's disease, ulcerative colitis, Behcet's disease, and HBV infection was experimentally validated, demonstrating that these ExPecto-predicted functional single nucleotide polymorphisms (SNPs) show allele-specific regulatory potential while the GWAS lead SNPs do not.

The scalability of ExPecto allows systematic characterization of the predicted expression effect space of potential mutations for each gene, by profiling over 140 million promoter proximal mutations. This enables systematic probing of the tissue-specific impact of gene human transcription dysregulation 'in silico' at a scale not yet possible experimentally, defining the evolutionary constraints on human gene expression. It was shown that the effects of potential mutations on each gene, which is referred to herein as the gene's 'variation potential', is indicative of the phenotypic impact of expression-altering mutations.

Integrating expression effect predictions and inferred evolutionary constraints, an end-to-end computational framework for full in silico prediction of disease-associated regulatory variation is proposed, from sequence to expression effects and subsequent fitness impacts. This framework is complementary to quantitative genetics and experimental approaches at a substantially larger scale and lower cost, including for inferring disease-causal mutations. The far-reaching potential of this approach was demonstrate by interpreting clinically-relevant mutations (even ones not captured by quantitative genetics) through successful prediction of disease risk.

Sequence-Based Cell-Type Specific Expression Prediction

Figure 7:
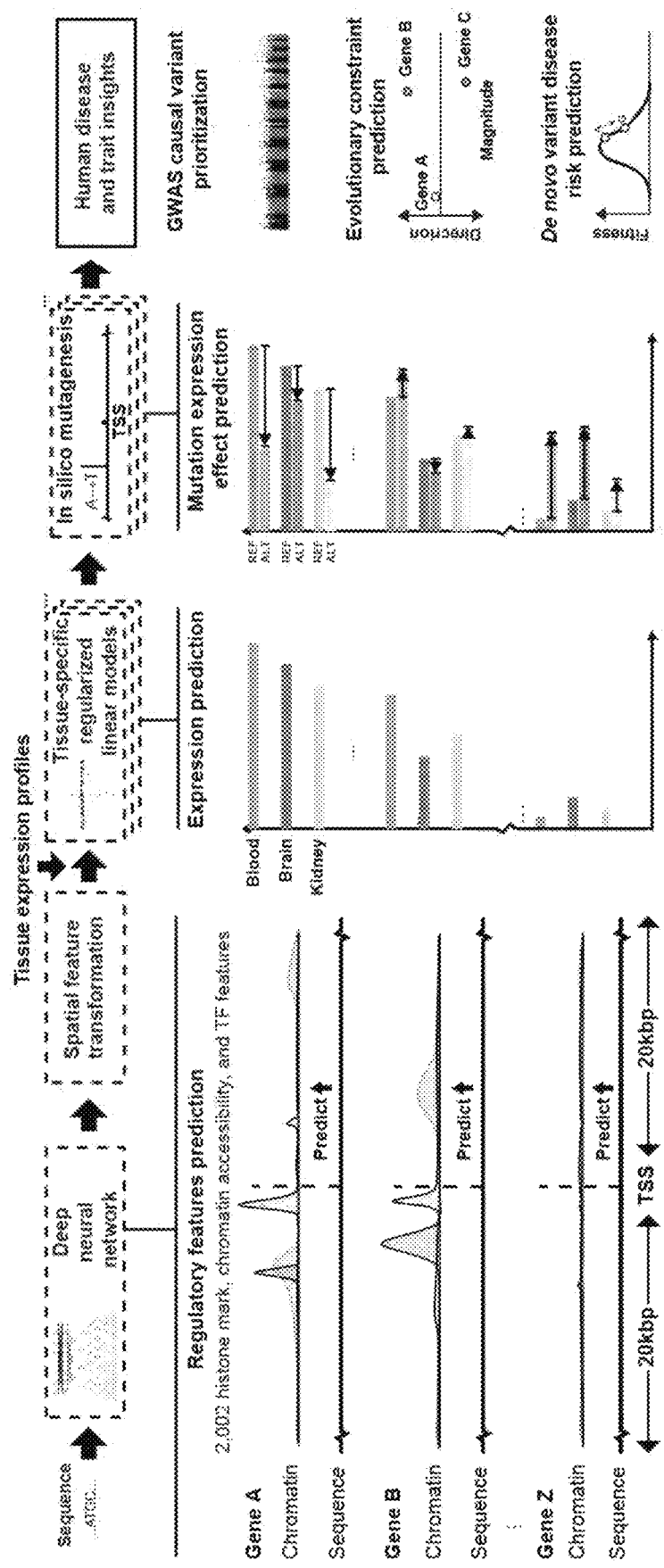
FIG. 7 provides an illustration of the ExPecto process to determine gene expression effects based on sequence and variants within the sequence in accordance with various embodiments of the invention.
Figure 8:
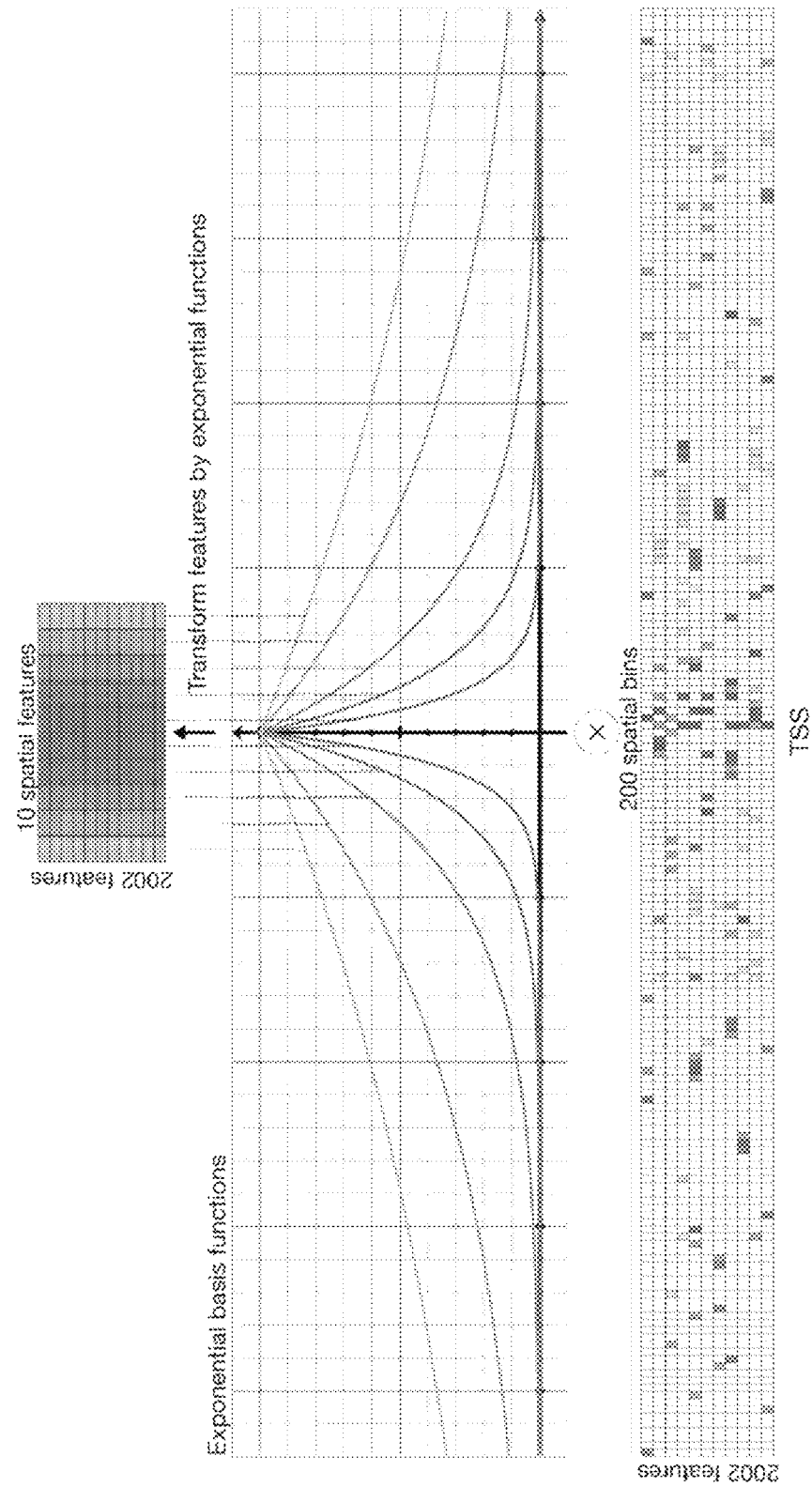
FIG. 8 provides a schematic representation of spatial transformation of the spatial features based on their location in relation to a gene's transcription start site in accordance with various embodiments of the invention.

To predict the tissue-specific expression from human promoter-proximal sequences, a modular framework was built (FIG. 7). First, deep learning was used to generate a repertoire of potential regulatory sequence representations capable of predicting epigenomic effects of any genomic variant from sequence only. This was accomplished with a deep convolutional neural network trained to predict 2,002 different features including histone marks, transcription factors and DNA accessibility profiles for over 200 tissues and cell types. Second, through a spatial feature transformation approach, the framework integrated predicted sequence-based epigenomic information across 40 kb region (FIG. 8). Third, tissue-specific regularized linear models used the transformed epigenomic information, which is centered on the transcription start site (TSS), to predict expression of Pol transcribed genes in each of the 218 tissues and cell types (one model per tissue for all genes). The resulting ExPecto framework is capable of predicting cell-type specific gene expression and the effects of genomic variants ab initio, having never trained on any variant information (neither matched expression or epigenetic data nor any genomic variant data).

Figure 9:
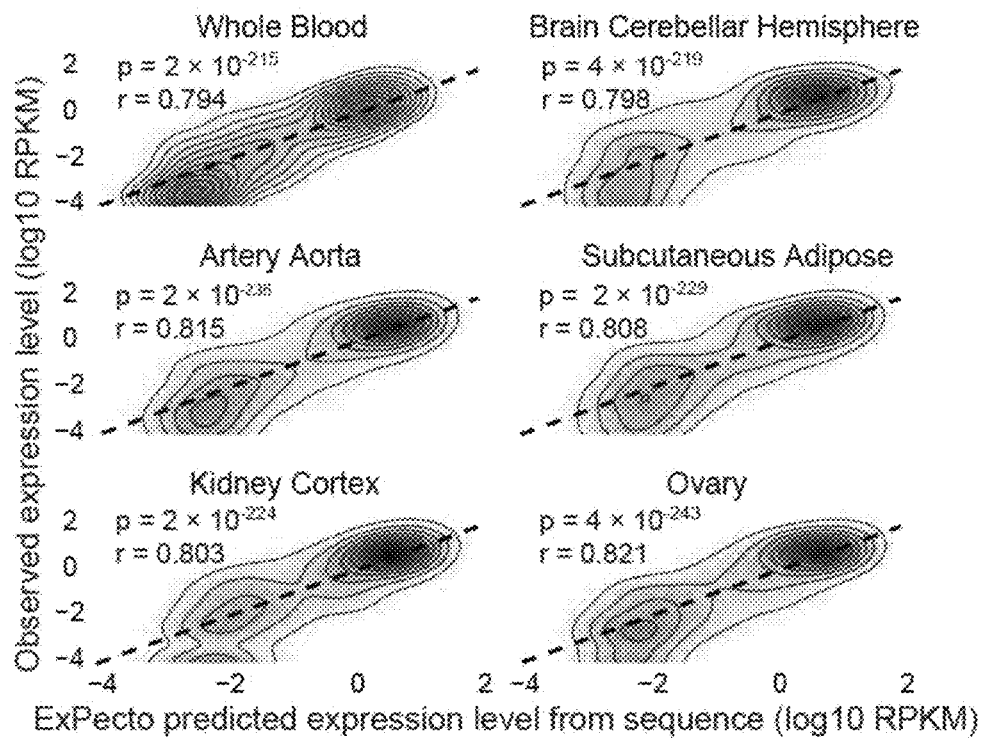
FIG. 9 provides results of the ExPecto predictions on holdout genes and their correlation with RNA-seq observations, generated in accordance with various embodiments of the invention.

ExPecto makes accurate predictions of gene expression levels from sequence, with 0.819 median Spearman correlation with observed expression log RPKM across 218 tissues and cell types (FIG. 9). This was evaluated on proximal sequences held out during all training of both the regulatory representations and the expression models. It was found that the expression models preferentially exploited sequence representations of transcription factors and histone marks (See Supplementary Table 1 of J. Zhou, et al., Nat. Genet. 50(8), 1171-1179 (2018)). DNase I sequence features, in contrast, had consistently lower weights ($p=6.9 \times 10^{-25}$ two-sided Wilcoxon rank sum test) likely due to the lack of causal dependency information, probably because DNase I hypersensitive sites can be caused by binding proteins of various functions.

Figure 10:
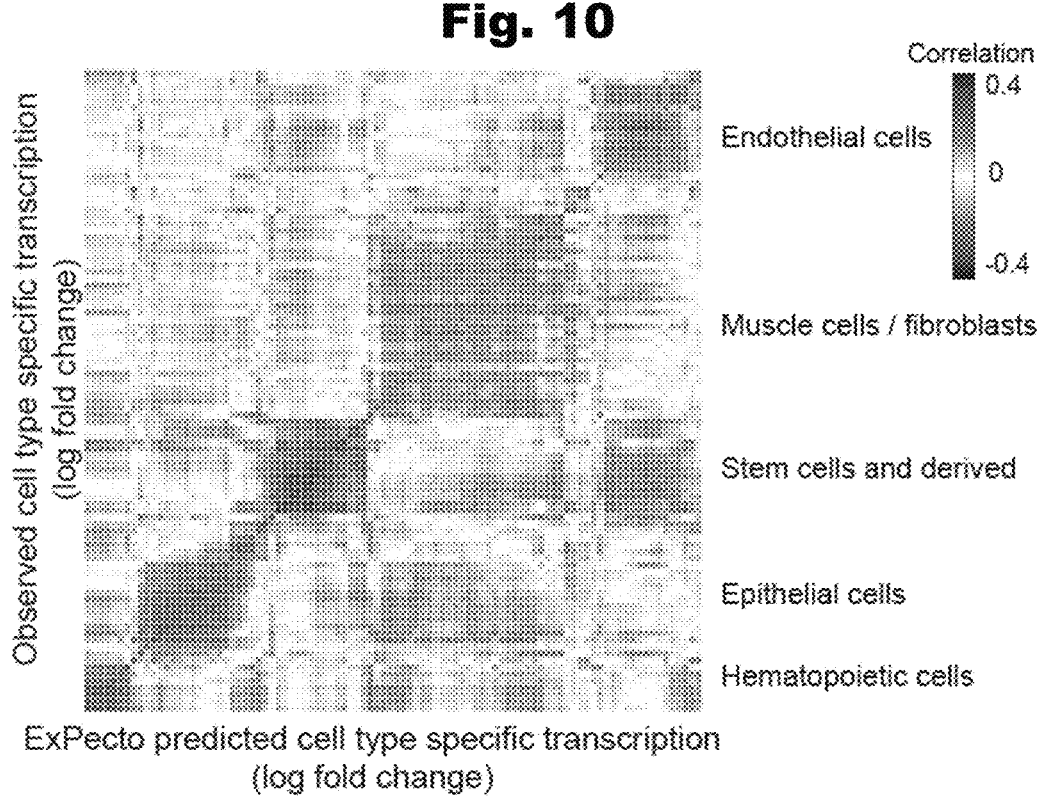
FIG. 10 provides an expression heat map of results of cell-type expression models, generated in accordance with various embodiments of the invention.

Furthermore, in addition to accurately capturing global expression, ExPecto predictions recapitulated the tissue specificity of expression, with expression predictions being significantly more similar to the experimental measurements from the correct cell type than other cell types on holdout sequences (FIG. 10). As cell type specificity of gene expression in the human body is determined by differential utilization of regulatory DNA sequences, it was examined whether the framework learned such cell type regulatory specificity. Indeed, the expression models could automatically learn to preferentially utilize sequence features from the most relevant cell type, even though no explicit tissue labels for these features were used. For example, the top weighted sequence features specific for the liver model corresponded to binding of seven transcription factors (TFs) in HepG2 cells of liver origin. For the breast-mammary gland model—all top five positive features are TFs (ERα and GR) in the breast cancer cell lines T-47D and ECC-1, and for the whole blood model—all top five features are from the blood-derived cell lines and erythroblast cells (See Supplementary Table 1 of J. Zhou, et al., *Nat. Genet.* 50(8), 1171-1179 (2018)).

Figure 11:
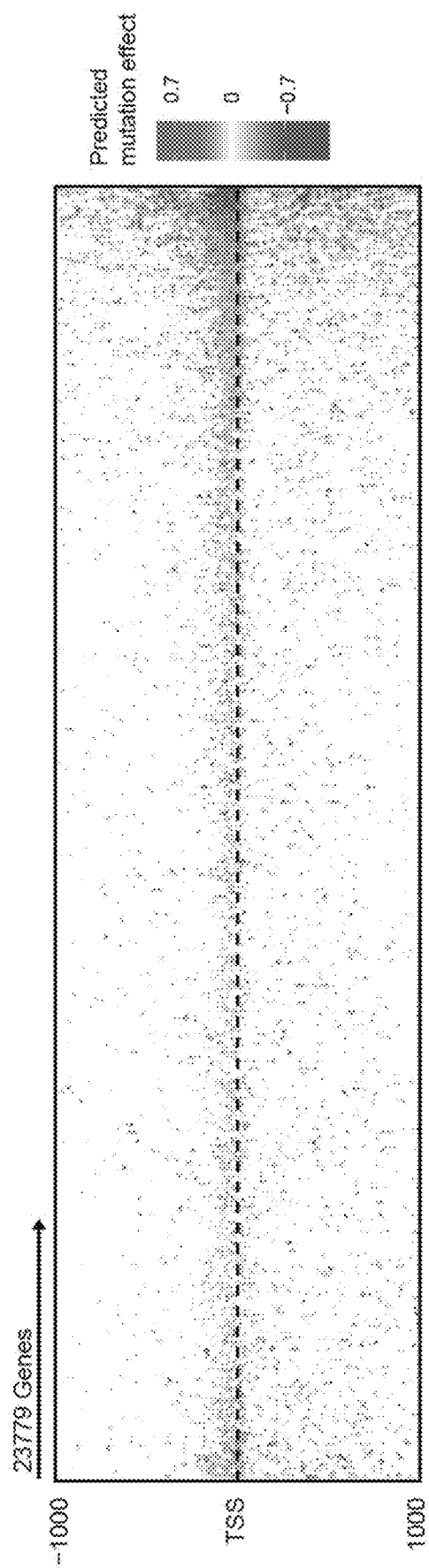
FIG. 11 provides mutation effects form in silico mutagenesis of promoter-proximal regions of 23,779 genes, generated in accordance with various embodiments of the invention.
Figure 12:
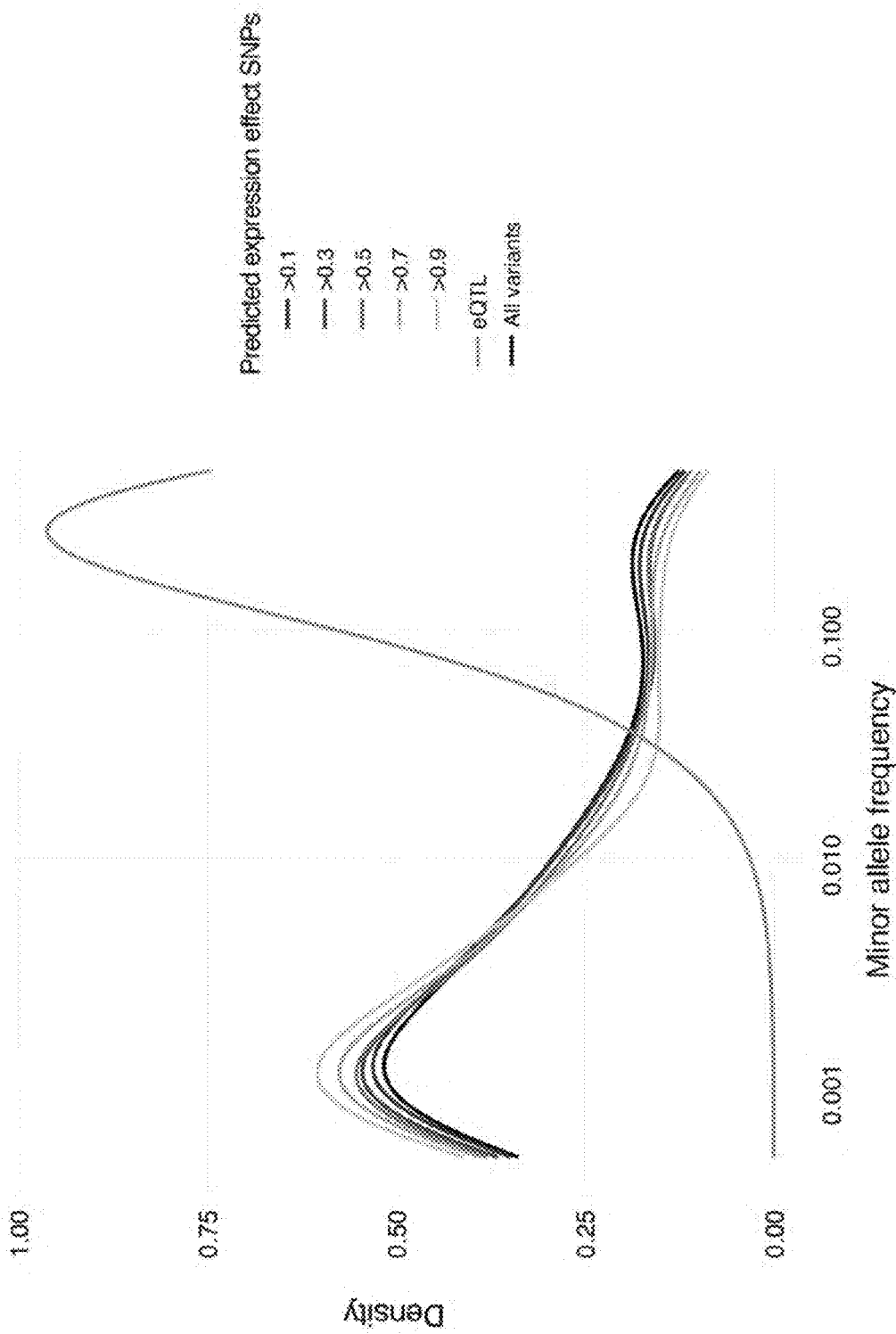
FIG. 12 provides data graph that shows ExPecto predicted variants do not show high allele frequency bias, generated in accordance with various embodiments of the invention.

The ability of ExPecto to predict tissue-specific gene expression from sequence provides the basis for estimating transcriptional effects of genomic variation (FIGS. 7 & 11). These computational predictions of variant effect do not use any variant-specific information for training and thus can scale to all human population variants and even billions of potential small alterations in the human genome. Thus, in contrast to quantitative genetics approaches, which detect mostly high frequency variants, the ExPecto approach is not biased by allele frequencies and works for both common and rare variants (FIG. 12). Therefore, an exhaustive in silico mutagenesis was applied to over 140 million variants, including all variants around 23,779 TSSs, all GWAS loci, and eQTL variants, in order to probe the effects of these variants (FIG. 11).

Effect of Genomic Variants on Tissue-Specific Expression

Figure 13:
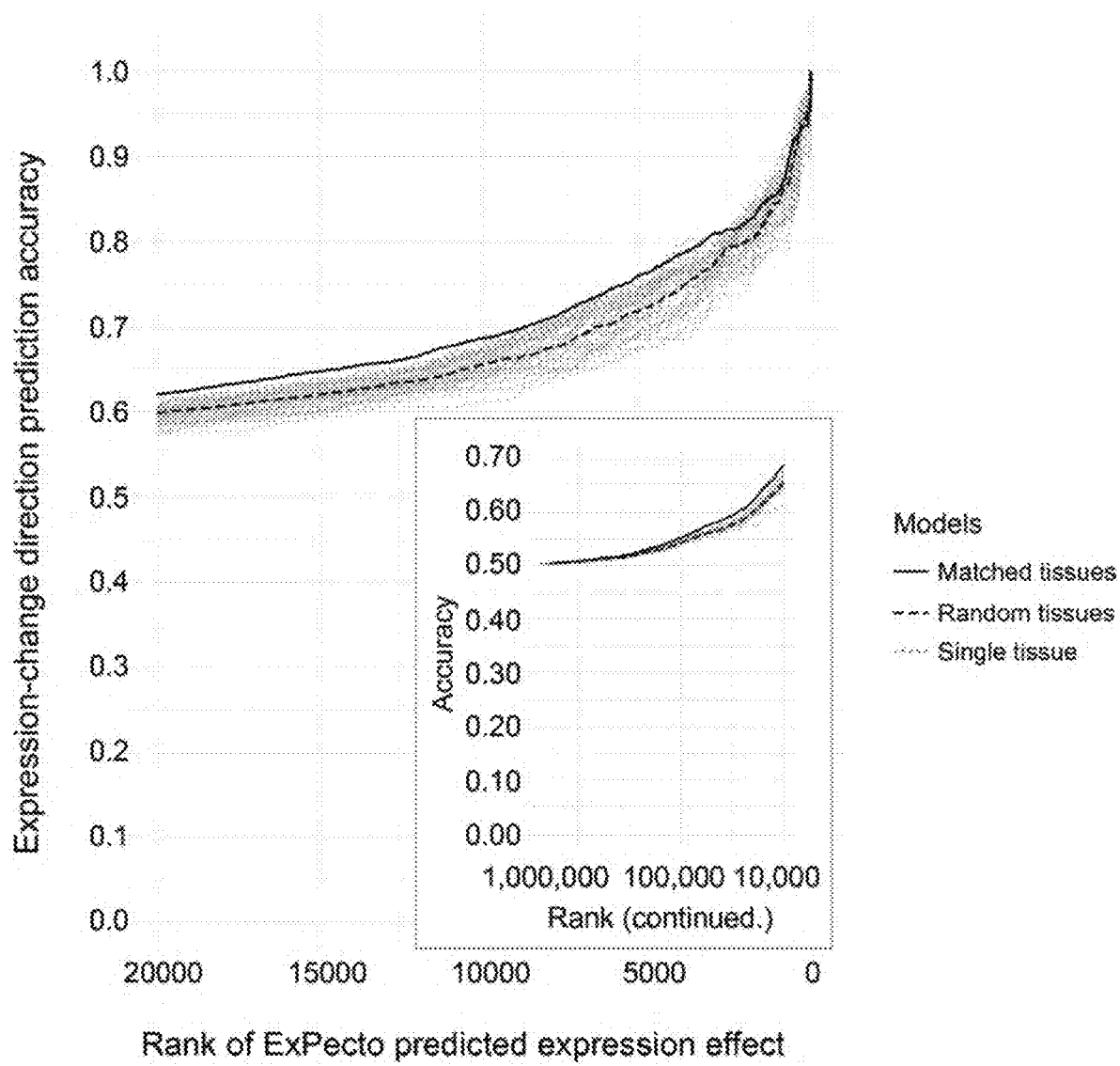
FIG. 13 provides data graph that shows tissue-specific expression models achieve higher accuracy in eQTL variant expression change directionality prediction, generated in accordance with various embodiments of the invention.

To evaluate ExPecto's predictions of tissue-specific effects of genomic variants on gene expression, the predictions were compared with eQTL data from multiple studies. ExPecto's ab initio sequence-based prediction is especially useful for prioritizing causal eQTL variants because the prediction is not confounded by linkage disequilibrium. Thus, even though a majority of eQTL variants are expected to cause no expression effect (of Genotype-Tissue Expression (GTEx) lead variants, only 3.5%-11.7% are estimated to be causal variants, which is <1% of all GTEx eQTL variants), ExPecto was designed to Predict causal variants (for more on GTEX eQTL variants, see F. Aguet, et al., *Nature* 550, 204-213 (2017), the disclosure of which is incorporated herein by reference). Among the GTEx-identified eQTLs, ExPecto correctly predicted the direction of expression change for 92% of the top 500 strongest effect variants (FIG. 13) and provides accurate predictions for tens of thousands of variants (FIG. 13). This suggests that a high proportion of eQTLs with strong predicted effects are causal in contrast to the background, as the eQTL effect direction of non-causal SNPs should be independent from the predicted directions. Moreover, ExPecto models for the correct tissue provided more accurate predictions than any other tissue (FIG. 13). The accuracy of ExPecto was also demonstrated on three other large-scale eQTL studies on brain, primary immune cells and blood respectively (FIG. 14) (for more on the large-scale eQTL studies, see H. J. Westra, et al., *Nat. Genet.* 45, 1238-1243 (2013); A. Ramasamy, et al., *Nat. Neurosci.* 17, 1418-1428 (2014); and B. P. Fairfax, et al. *Nat. Genet.* 44, 502-510 (2012); the disclosures of which are each incorporated herein by reference).

In addition, ExPecto can accurately predict causal eQTLs when evaluated with data from in vitro massively parallel reporter assays (MPRA) in lymphoblastoid cells (for more on lymphoblastoid study, see R. Tewhey, et al., *Cell* 165, 1519-1529 (2016), the disclosure of which is incorporated herein by reference). The strongest predicted effect variants from the lymphoblastoid expression model differentially activated transcription, and the model was able to predict expression change directionality with nearly perfect accuracy for top prioritized variants (FIG. 15). Notably, the lymphoblastoid model outperformed all other tissue models (AUROC=0.815), again demonstrating the importance of tissue-specific expression modeling in causal-effect predictions.

Figure 16:
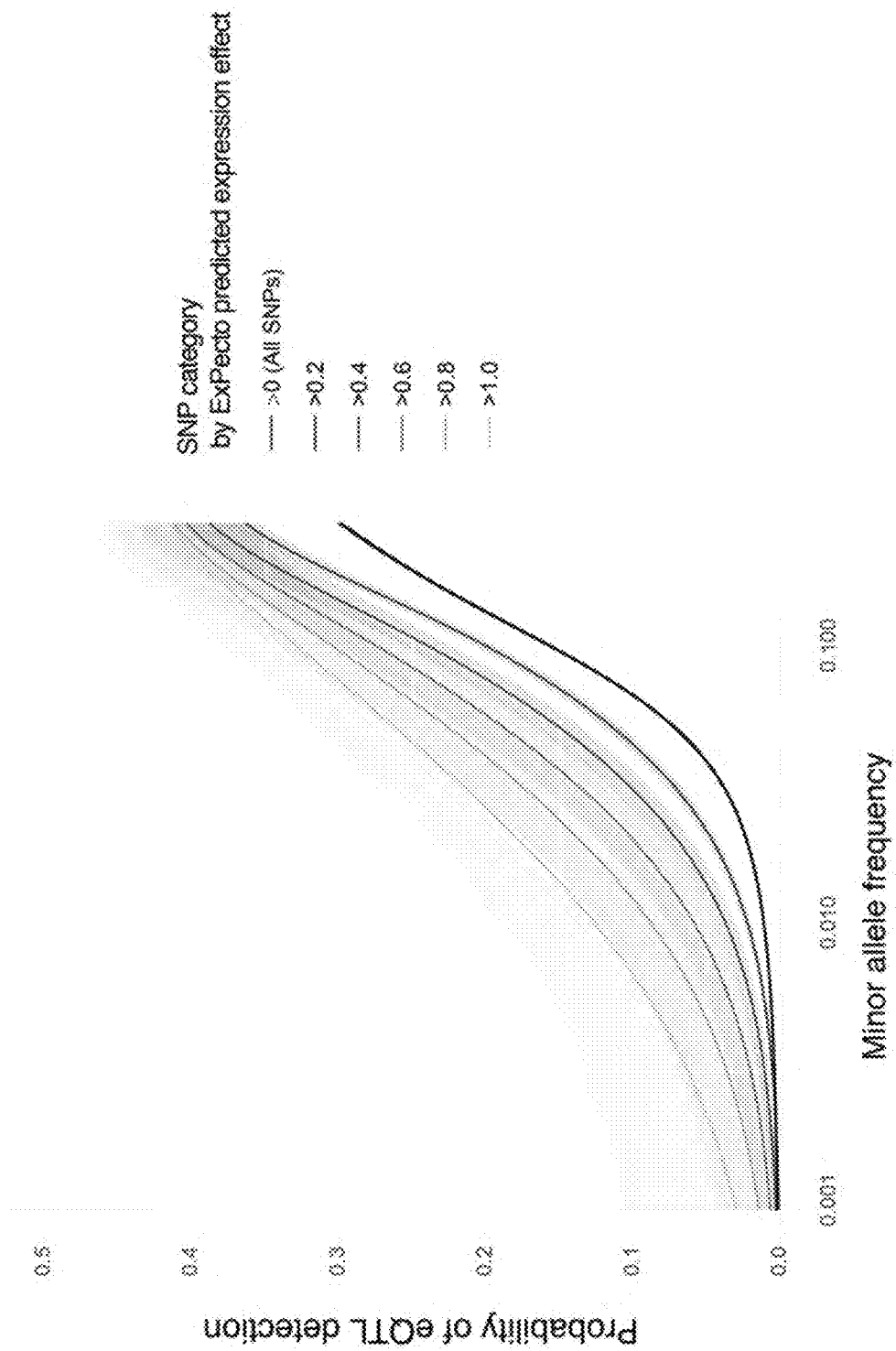
FIG. 16 provides a data graph that shows systematic expression effects prediction across a wide-range of minor allele frequencies, generated in accordance with various embodiments of the invention.

As expression models can accurately predict causal gene expression effects of SNVs and small INDELs among eQTLs, the expression effect of human population variants across the full range of allele frequencies was examined (16.5 million variants from the 1000 Genomes project) (See Supplementary Data 1 of J. Zhou, et al., *Nat. Genet.* 50(8), 1171-1179 (2018)). In contrast to quantitative genetics approaches, which detect mostly high frequency variants (FIG. 12), the ExPecto approach is not biased by allele frequencies and can detect both common and rare variants. Indeed, the ExPecto high expression effect variants have similar MAF distribution to all 1000 Genomes variants (FIG. 12). It was revealed that variants with stronger predicted expression effect are enriched for GTEx eQTLs at all allele frequencies (FIG. 16). Thus, sequence-based expression models can be powerful tools in the interpretation of rare functional variants.

Prioritizing and Experimental Study of Causal GWAS Variants

Figure 17:
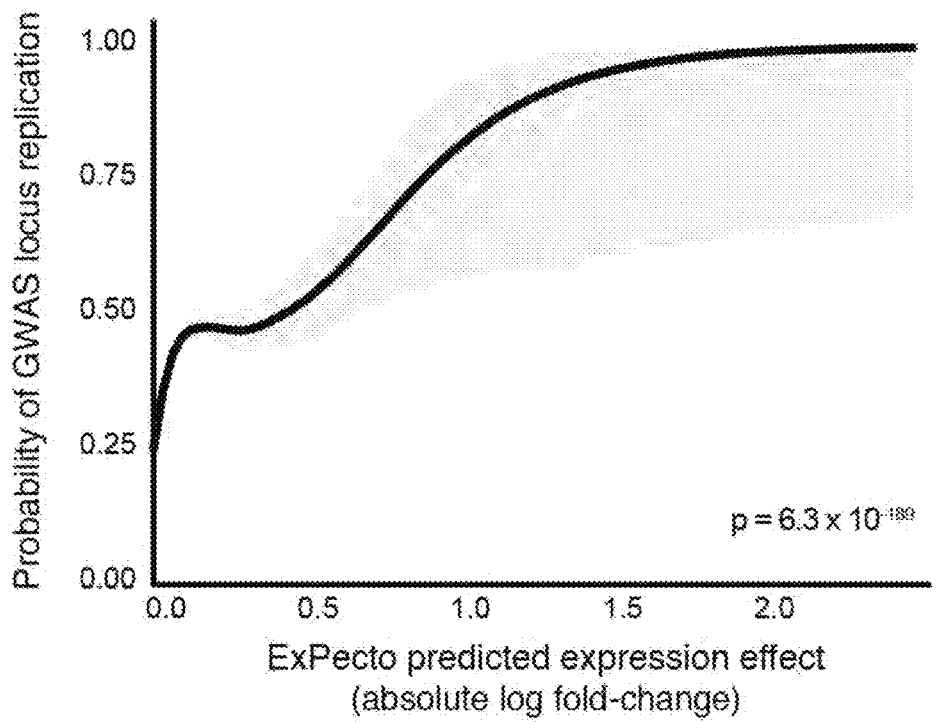
FIGS. 17 and 18 provide data graphs that show GWAS loci stronger predicted effect variants are more likely to be replicated by separate studies, generated in accordance with various embodiments of the invention.
Figure 18:
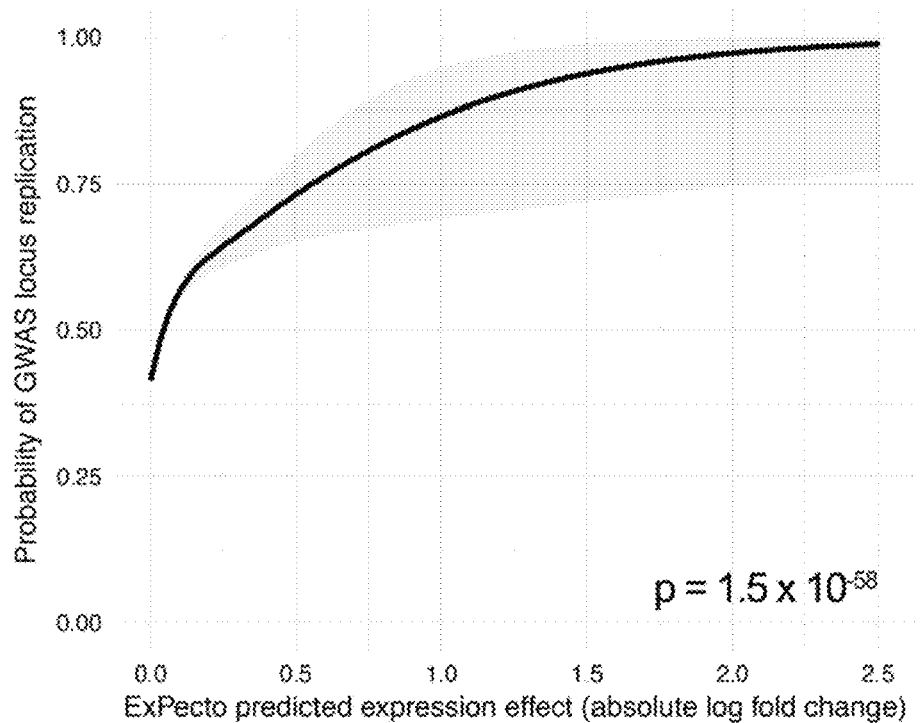
Figure 19:
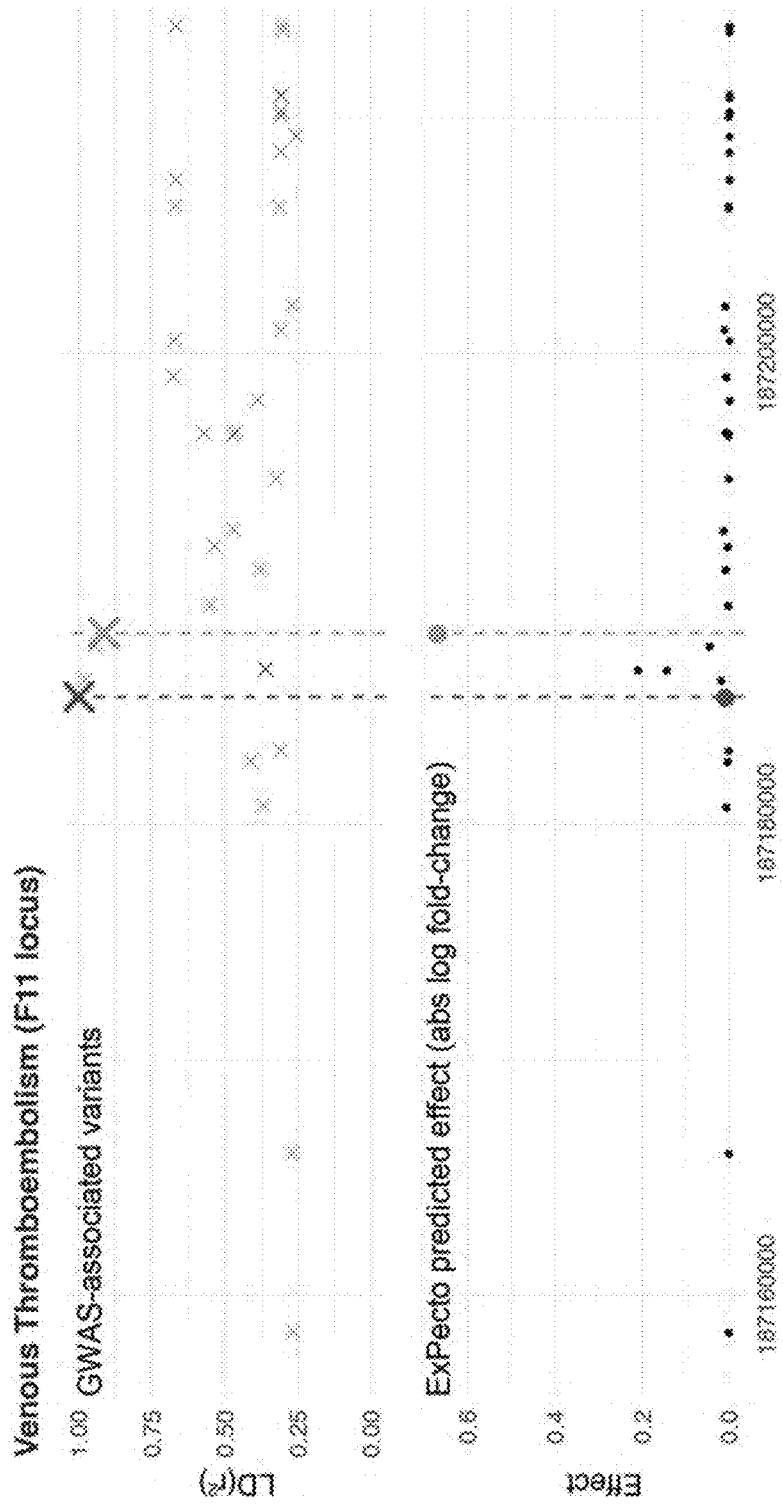
FIGS. 19 to 21 provide data graphs that show expression effect of prediction-prioritized linkage disequilibrium variants that were discovered in various GWASs, generated in accordance with various embodiments of the invention.
Figure 20:
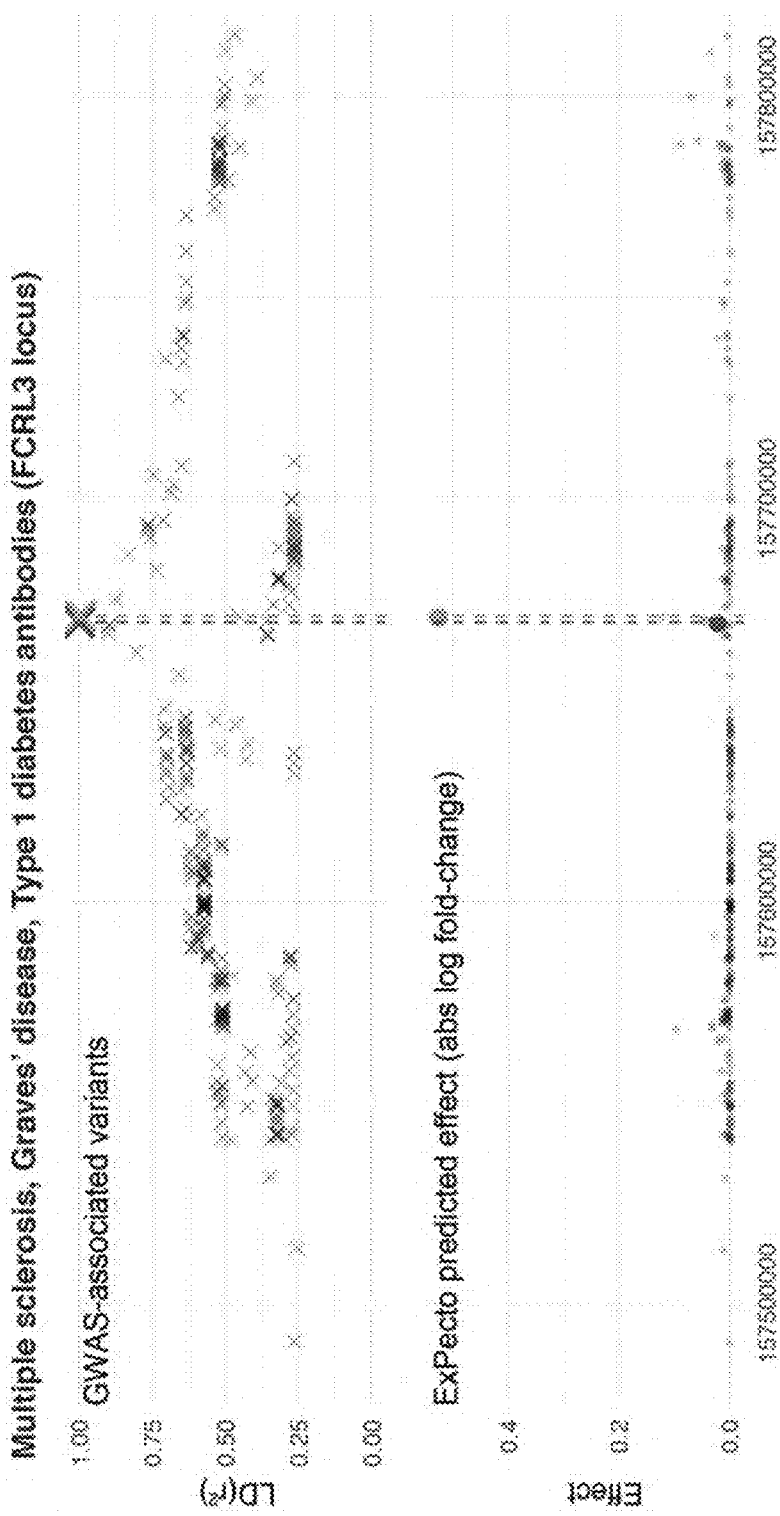
Figure 21:
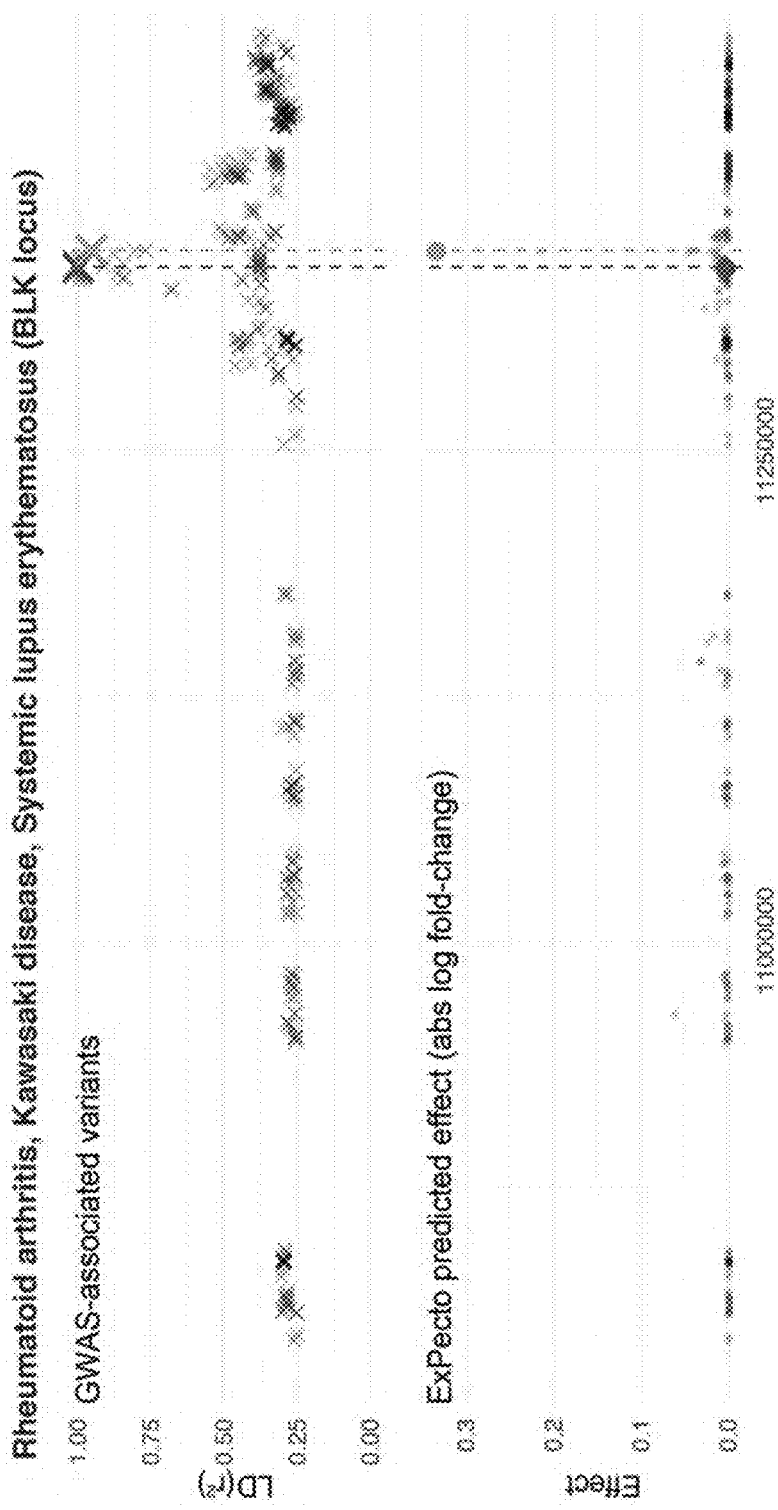

ExPecto's variant expression effect predictions were utilized to prioritize causal variants from disease/trait loci of 3,000 GWAS studies (See Supplementary Table 2 of J. Zhou, et al., *Nat. Genet.* 50(8), 1171-1179 (2018)) (for more on GWAS studies, see J. Macarthur, et al., *Nucleic Acids Res.* 45, D896-D901 (2017), the disclosure of which is incorporated herein by reference). While GWASs reveal the genetic basis of human diseases and traits by identifying a multitude of associated loci, this approach generally lacks the resolution to pinpoint causal genomic variants due mainly to linkage disequilibrium. Assessing overall performance of ExPecto prioritized variants, it was found that loci with the stronger predicted effect variants were significantly more likely to be replicated in a different GWAS study ($p=6.3\times10^{-189}$, two-sided Wald test with logistic regression, FIG. 17, see also FIG. 18 for analysis using only $p<5\times10^{-8}$ variants). Moreover, the stronger predicted effect GWAS linkage disequilibrium (LD) variants were more likely to be the exact replicated variant ($p=5.6\times10^{-14}$, two-sided Wald test with logistic regression). For instance, an earlier Venous Thromboembolism GWAS[19] identified rs3756008 as the lead causal variant, however, ExPecto-prioritized LD variant rs4253399 near the F11 locus was discovered with a later study using a larger cohort (FIG. 19) (for more on cohort, see W. Tang, et al., *Genet. Epidemiol.* 37, 512-521 (2013), the disclosure of which is incorporated herein by reference). Similar examples include variants in autoimmune diseases-associated loci (rs7528684, rs2618476) (FIGS. 20 & 21) (for more on these studies, see V. Planol, et al., *PLoS Genet.* 7, e1002216 (2011); X. Chu, et al., *Nat. Genet.* 43, 897-901 (2011); S. Sawcer, et al. *Nature* 476, 214-219 (2012); R. R. Graham, et al., *Nat. Genet.* 40, 1059-61 (2008); J. Bentham, et al., *Nat. Genet.* 47, 1457-1464 (2015); and Y. C. Lee, et al., *Nat. Genet.* 44, 522-5 (2012); the disclosures of which are each incorporated herein by reference). These results support the potential of using predicted expression effect information to improve identification of causal associated loci from GWAS studies.

Figure 22:
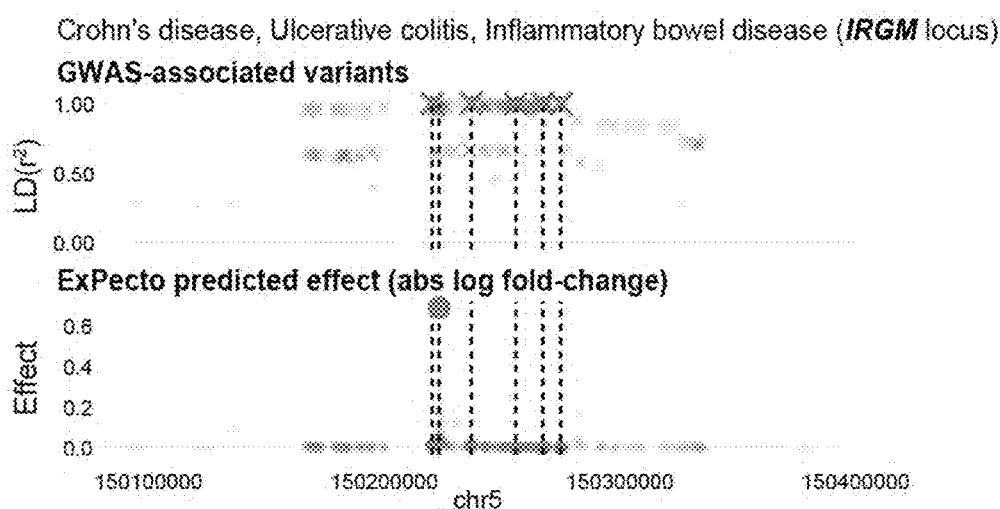
FIGS. 22 to 27 provide data graphs that show the ability of ExPecto to predict casual variants in comparison with various GWASs, generated in accordance with various embodiments of the invention.
Figure 23:
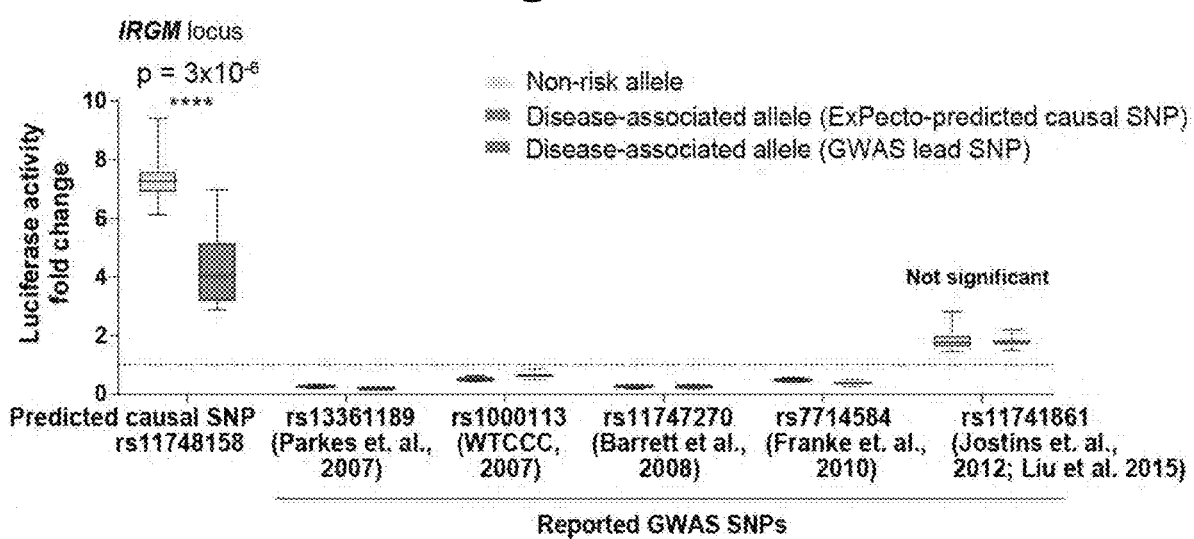
Figure 24:
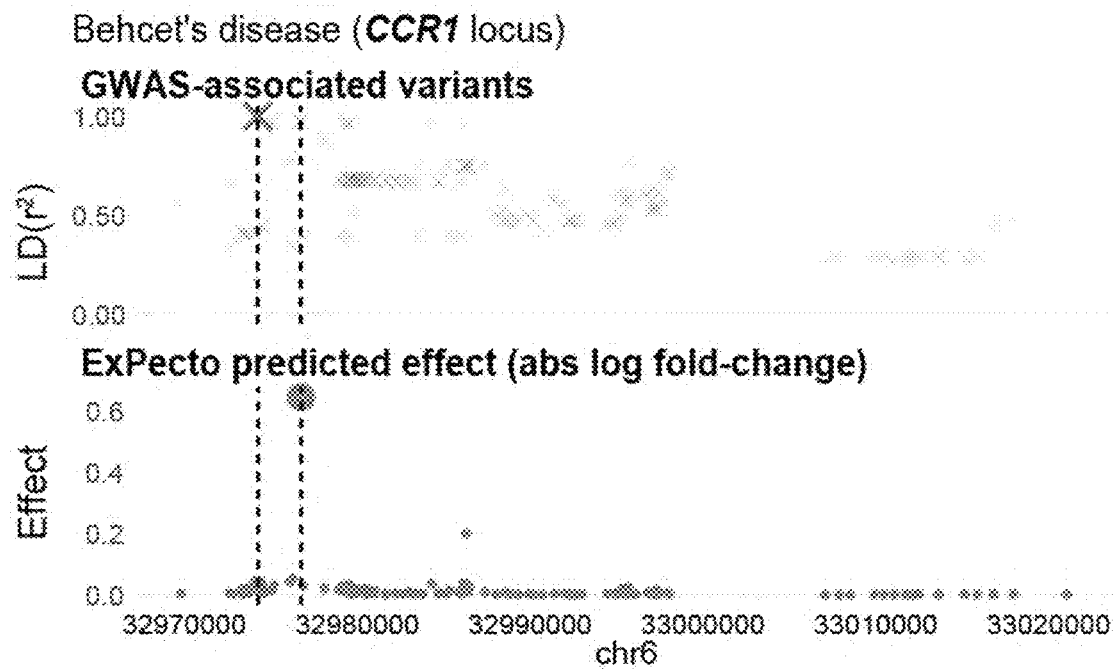
Figure 25:
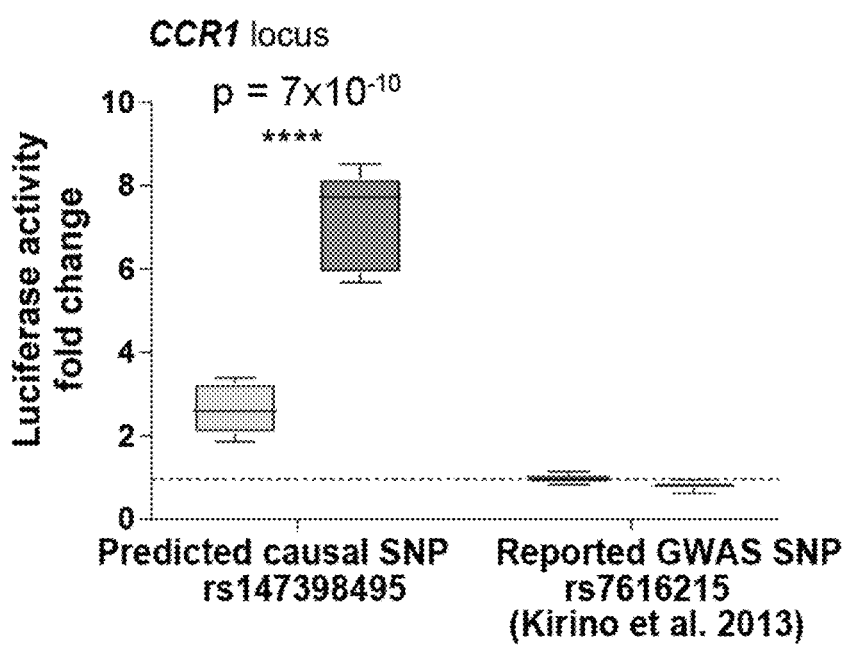
Figure 26:
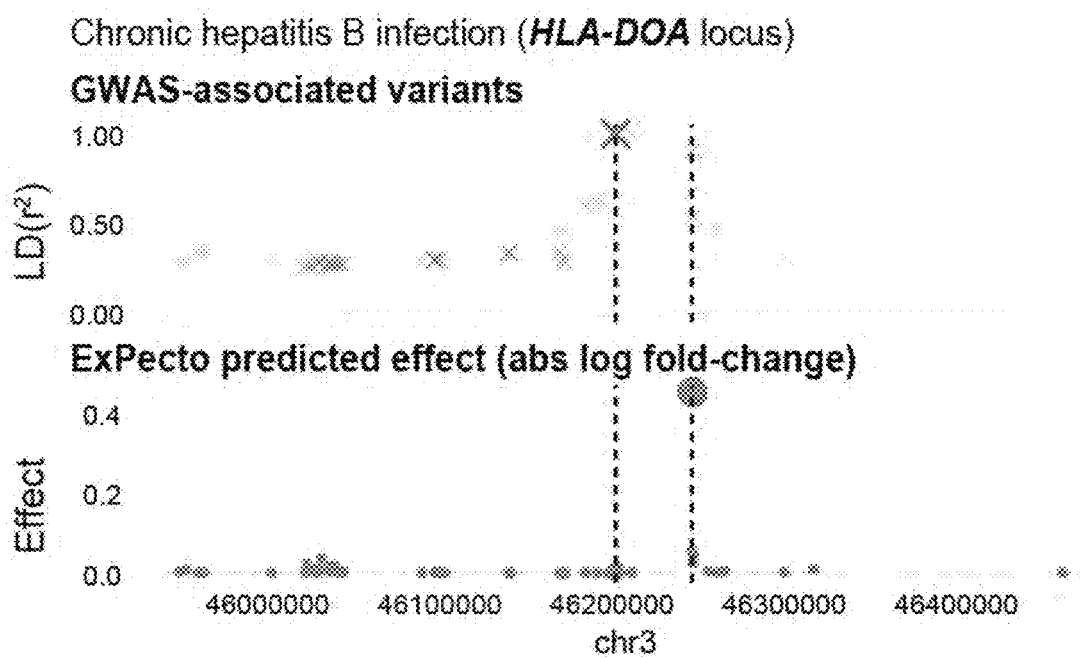
Figure 27:
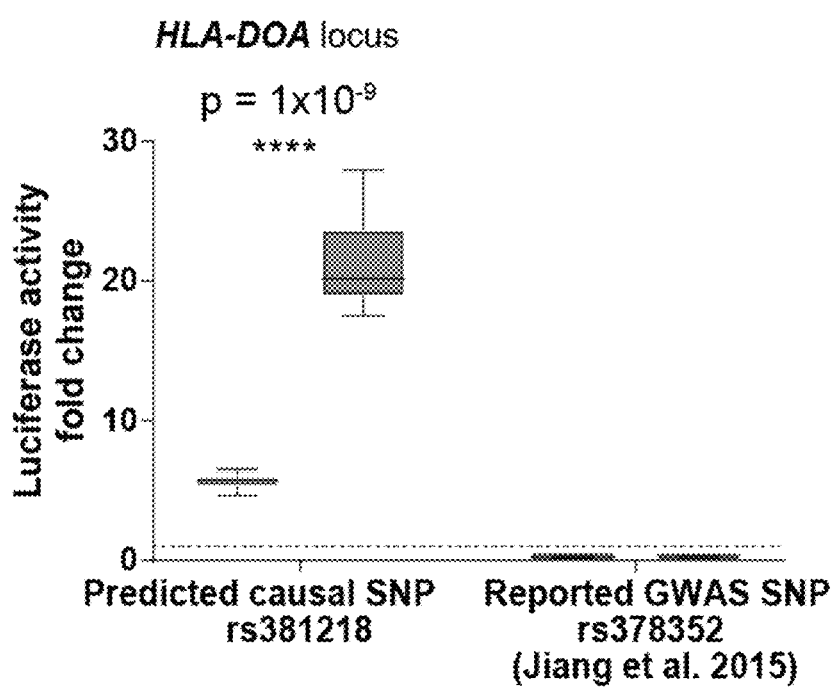

The expression alteration effects of the top three ExPecto-prioritized SNPs was experimentally measured on immunity-related diseases and their allele-specific regulatory potential was compared against the lead SNPs from the corresponding GWASs (FIGS. 22, 24 & 26). It was found that these expression effect-prioritized LD SNPs, while having no prior evidence of functionality, showed transcriptional regulatory activity whereas lead GWAS SNPs did not (as measured by reporter expression assays). (FIGS. 23, 25 & 27). The top ExPecto-prioritized SNP, rs1174815, is predicted to decrease the expression of IRGM, an innate immune response gene significantly associated with Crohn's disease, ulcerative colitis and general inflammatory bowel disease, and indeed a significant decrease in reporter expression was observed (FIGS. 22 & 23, $p=3\times10^{-8}$). The second top SNP rs147398495, associated with Behcet's disease and near CCR1, a chemokine receptor gene, also significantly changed transcriptional regulatory activity (FIGS. 24 & 25, $p=7\times10^{-10}$). For a Chronic HBV infection-associated GWAS locus, the third top SNP, rs381218, was predicted by ExPecto to affect the expression of HLA-DOA, a MHC II gene functional in B-cell lysosomes, and indeed, results in 4-fold change in reporter activity (FIGS. 26 & 27, $p=1\times10^{-9}$). In all seven examined cases, none of the lead SNPs in the GWASs showed significant differences in transcriptional regulatory activity. Importantly, the directionalities of the expression changes for all three top LD variants were also correctly predicted by ExPecto (See Supplementary Table 2 of J. Zhou, et al., *Nat. Genet.* 50(8), 1171-1179 (2018)). These results demonstrate the potential of expression-prediction based causal variant prioritization for identifying disease and trait-associated alleles of true functional impact.

Variation Potentials and Evolutionary Constraints of Genes

Figure 28:
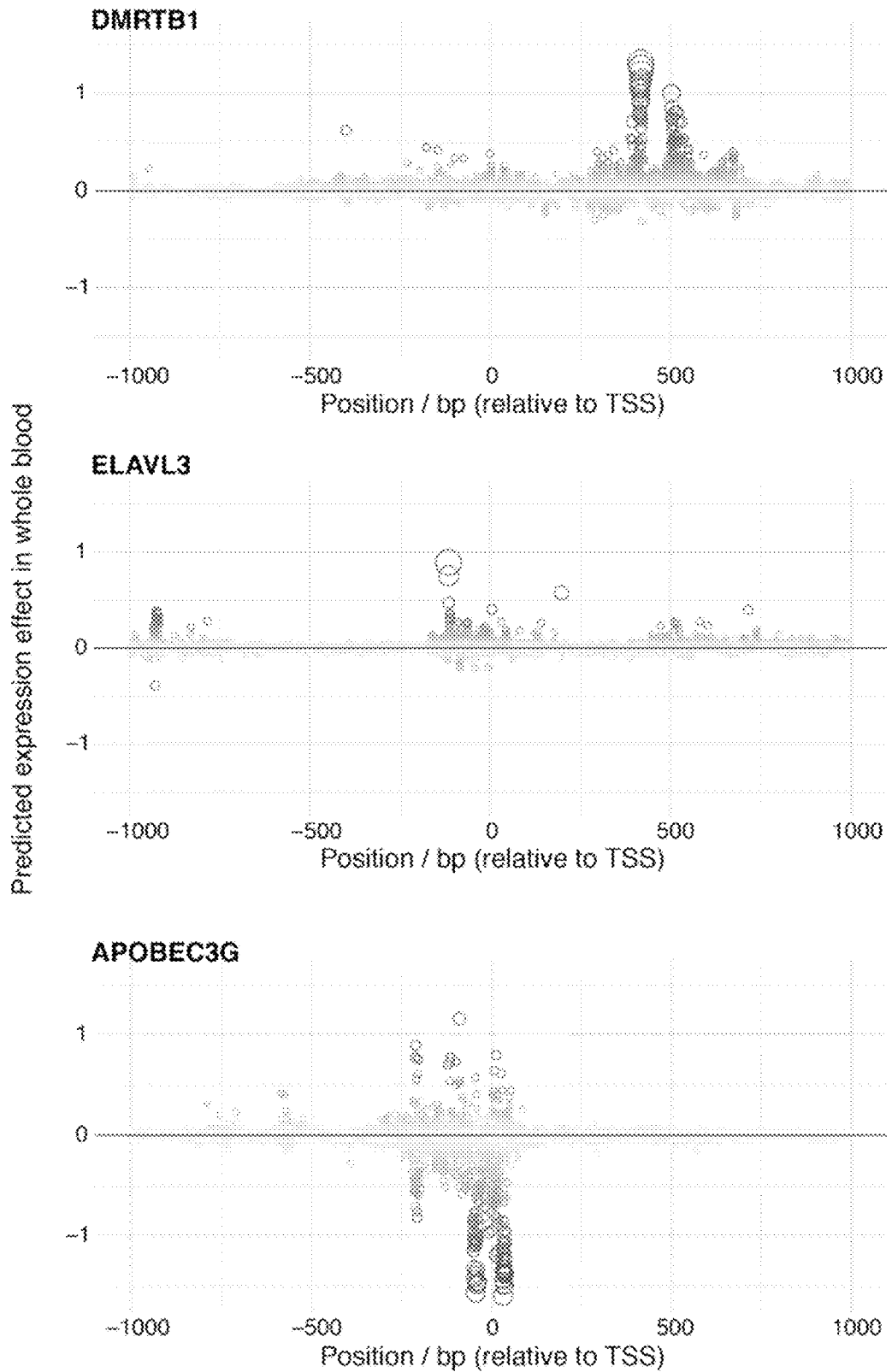
FIG. 28 provides data graphs that show results of exemplary in silico mutagenesis prediction effect profiles for various genes, generated in accordance with various embodiments of the invention.

A substantial gap still exists between predicting expression effect and estimating subsequent phenotypic consequences. The complexity of human as an organism poses significant difficulties in predicting phenotypic or disease consequences of expression alteration where perturbations of different genes elicit distinct consequences. As the Expecto model enables exploration of tissue-specific expression effects of genomic sequence variation at an unprecedented scale, essentially providing an 'in silico' assay of every possible transcriptional effect of a variant, it enables one to analyze the trace of selection on the regulatory sequences from the space of all potential mutations. It is proposed that the collective effects of potential mutations on each gene, which is referred to as a gene's 'variation potential' (VP) (FIG. 28.), are indicative of the phenotypic impact of expression-altering mutations. Furthermore, it was found that variation potential is indicative of innate expression properties of genes (e.g. tissue specificity of expression and activation/repression status).

Figure 29:
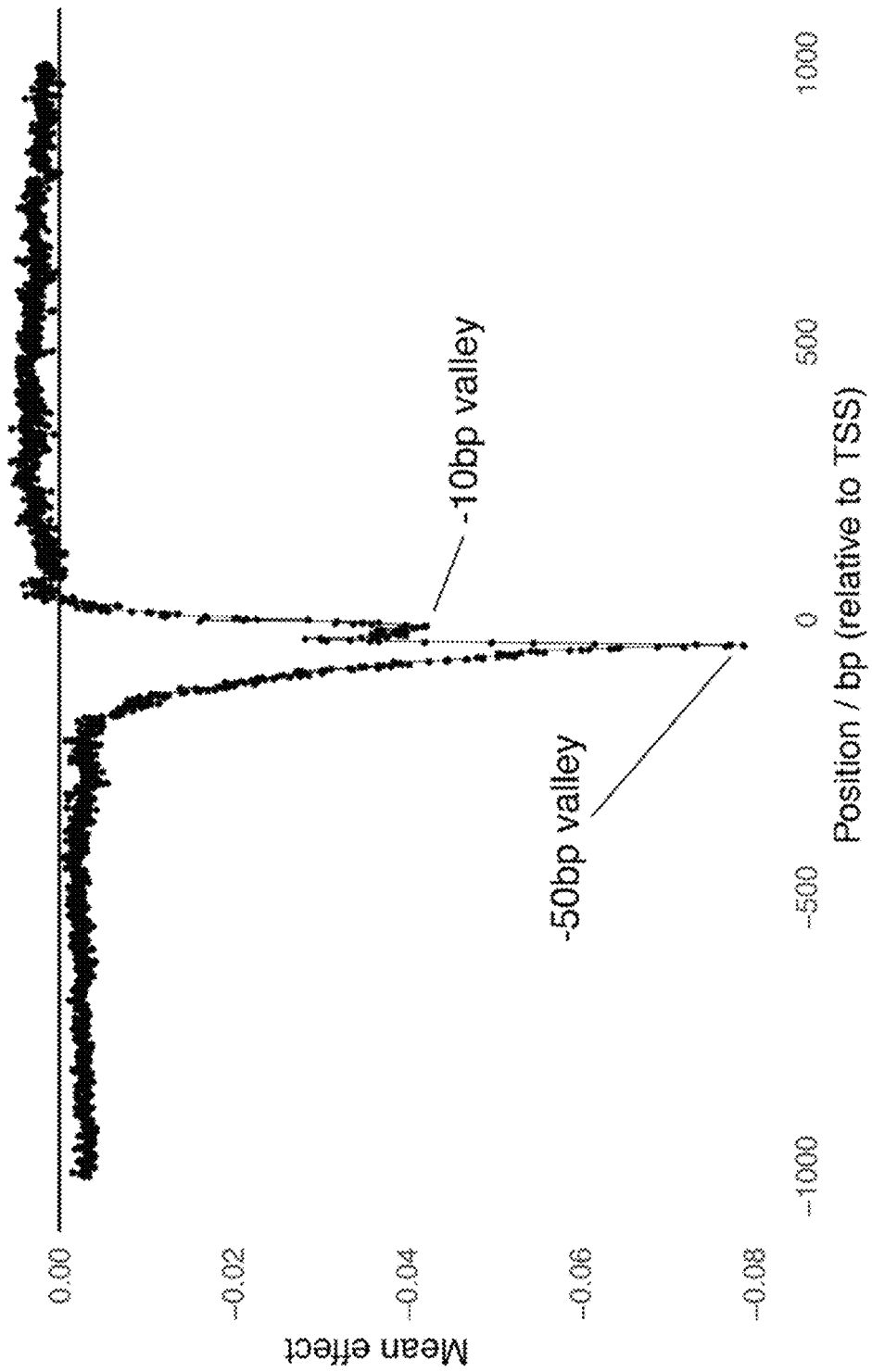
FIG. 29 provides a data graph that shows average spatial profile of potential mutation effects, generated in accordance with various embodiments of the invention.
Figure 30:
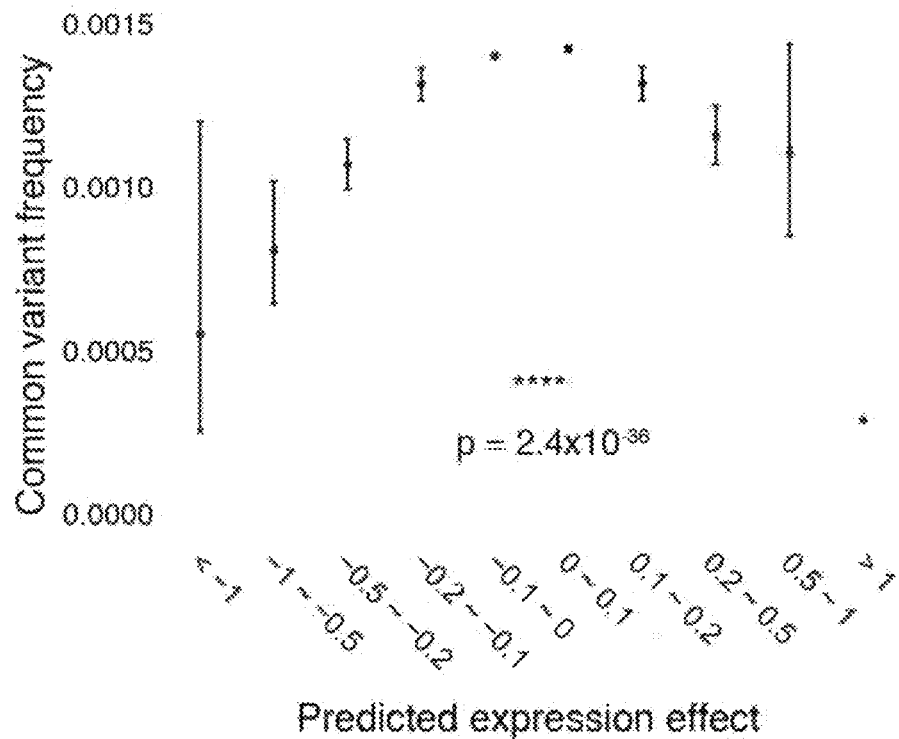
FIGS. 30 and 31 provide data graphs that show strong prediction expression effect at mutation sites are under evolutionary constraint across wide span of evolutionary history, generated in accordance with various embodiments of the invention.
Figure 31:
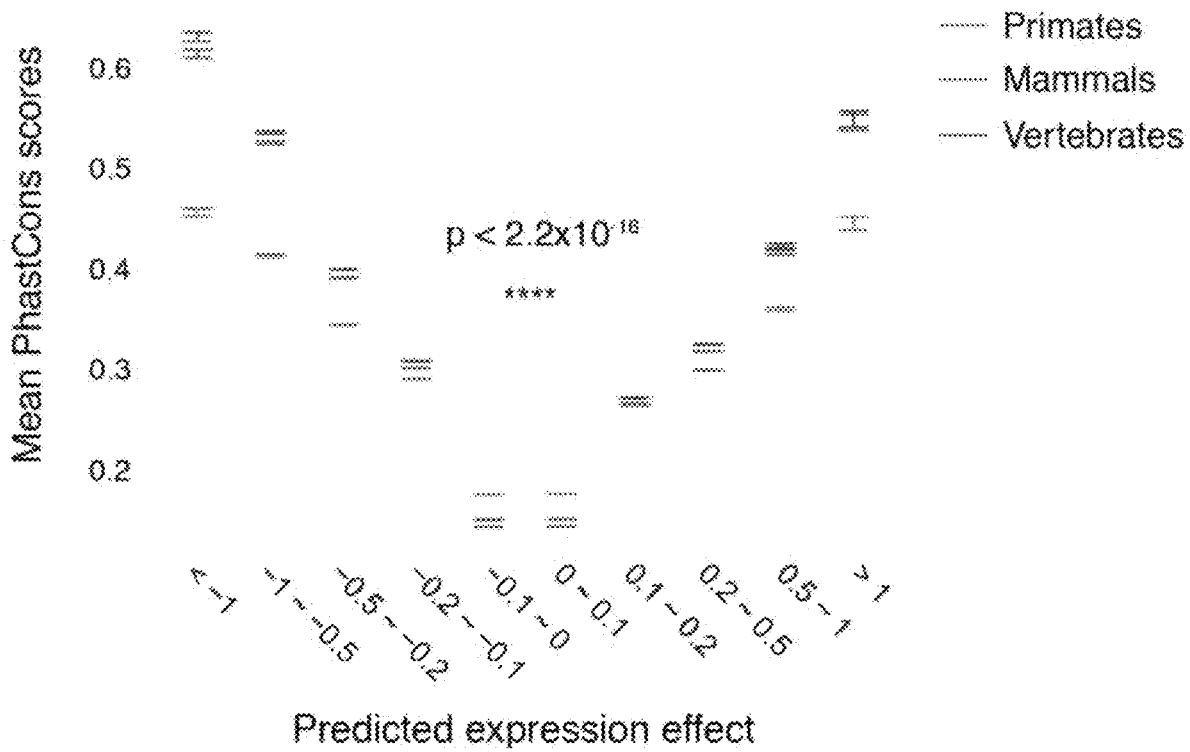

A catalog of predicted effects was computed for more than 140 million mutations that include all possible single nucleotide mutations 1 kb upstream and downstream of the TSS for each Pol I-transcribed gene. This identifies over 1.1 million mutations with a strong predicted expression effect (at high confidence). It was found that mutations predicted to decrease expression were generally positioned at the immediate upstream of the TSS near −50 bp (FIG. 29), which is the typical position of core promoter elements. The bases with stronger predicted mutation effects showed significantly higher evolutionary constraints both in the modern human population (FIG. 30) and in ancestral evolutionary history (FIG. 31).

Figure 32:
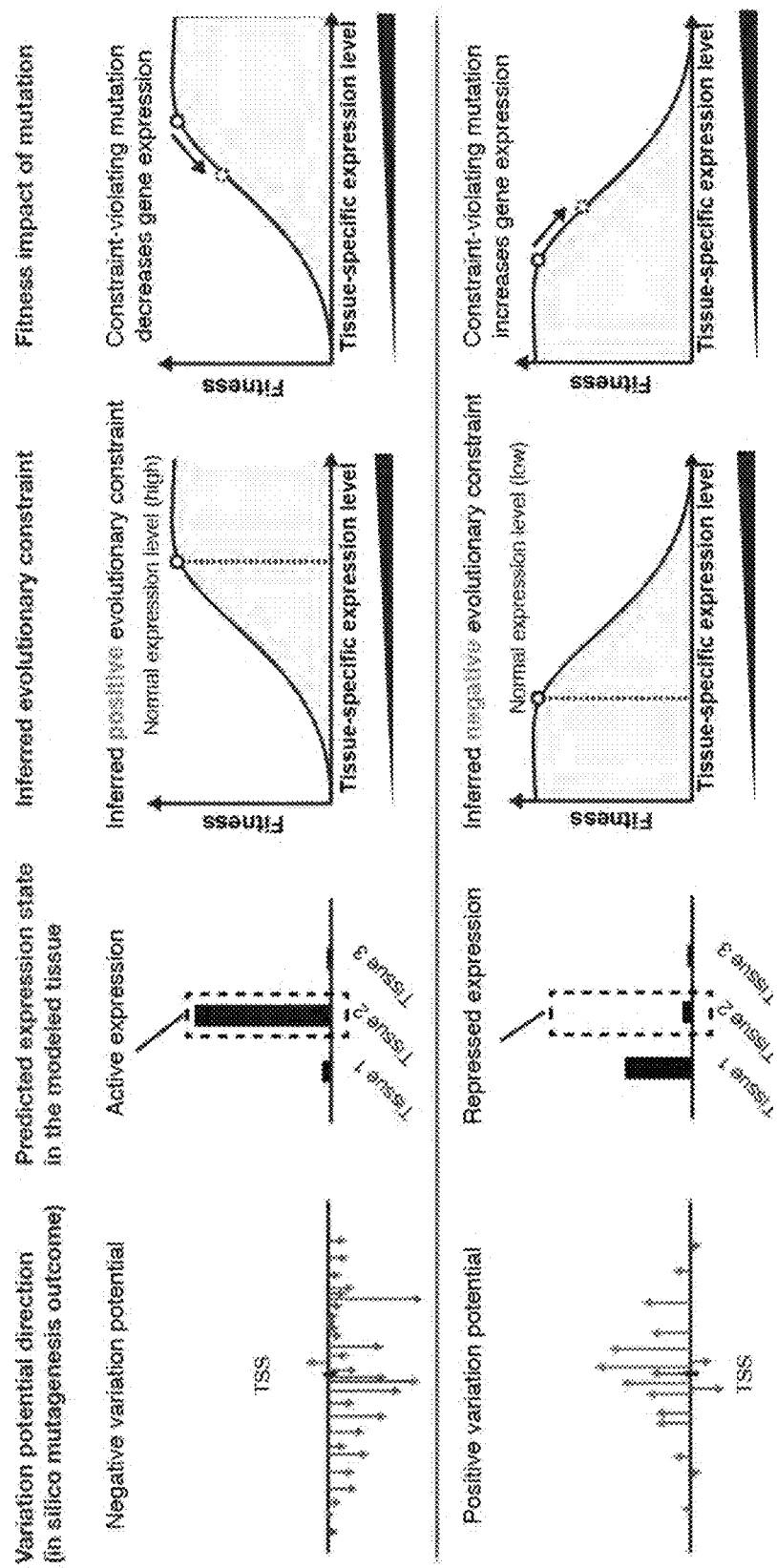
FIG. 32 provides a schematic overview of association between variation potential, gene expression, and evolutionary constraints, utilized in accordance with various embodiments of the invention.
Figure 33:
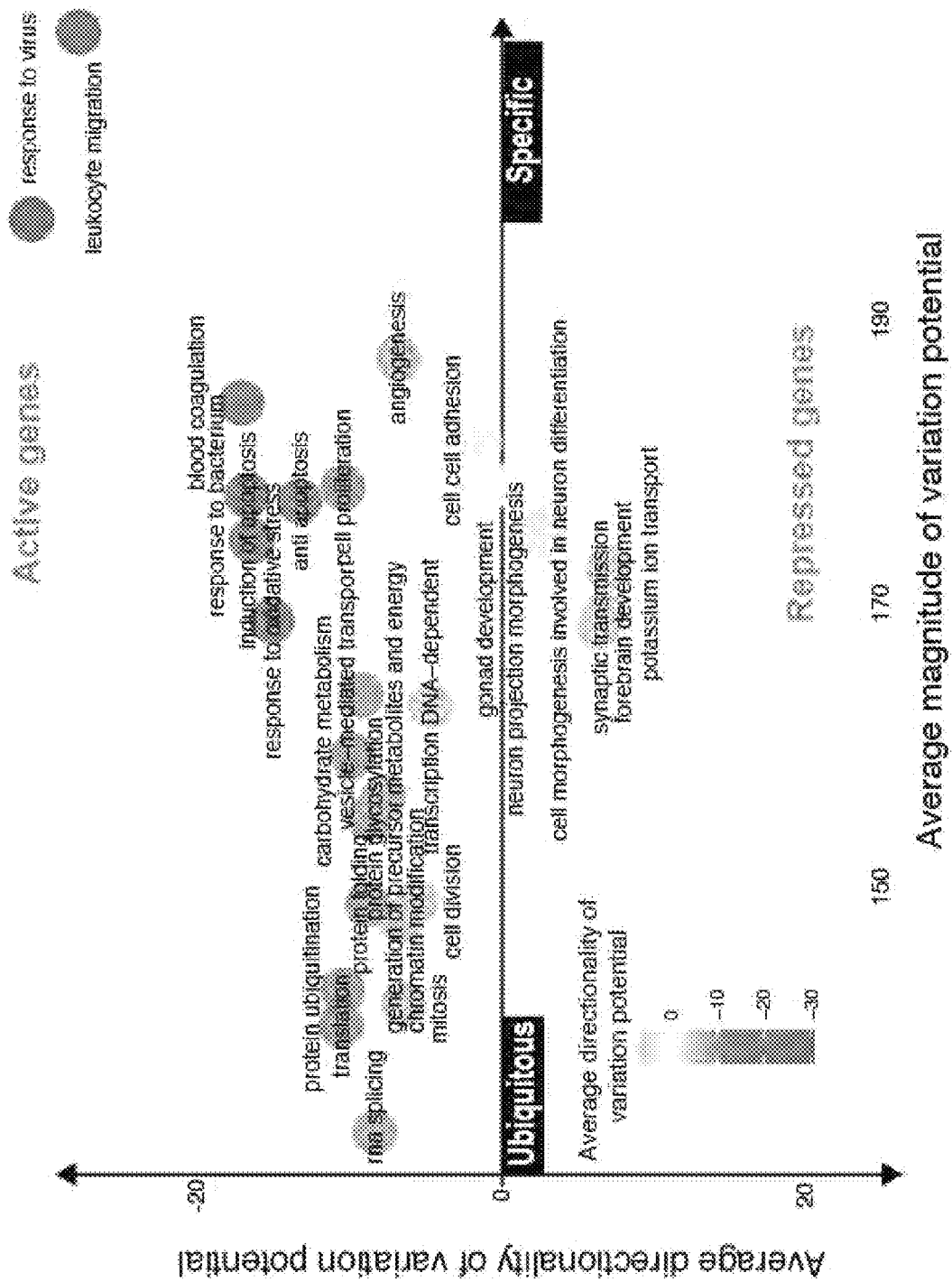
FIG. 33 provides a data graph depicting gene expression specificity and activation status can be predicted form the magnitude and direction of gene variation potential, generated in accordance with various embodiments of the invention.
Figure 34:
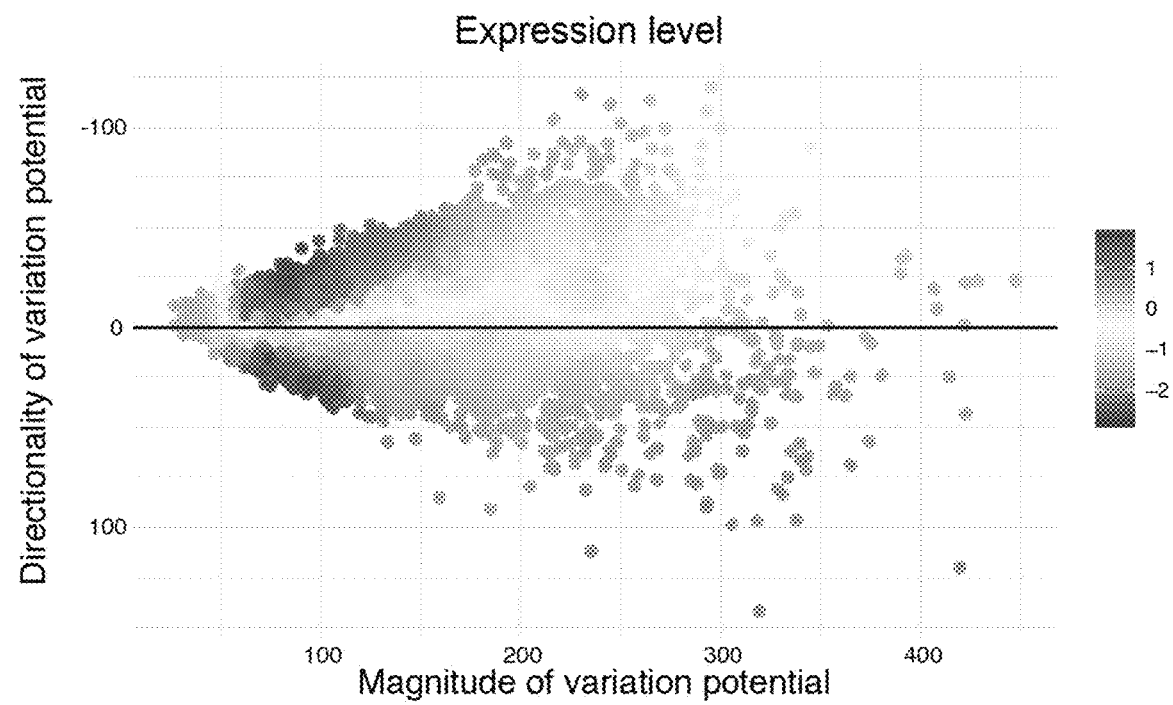
FIGS. 34 and 35 provide data graphs that show variation potential is predictive of gene-wise expression properties, generated in accordance with various embodiments of the invention.
Figure 35:
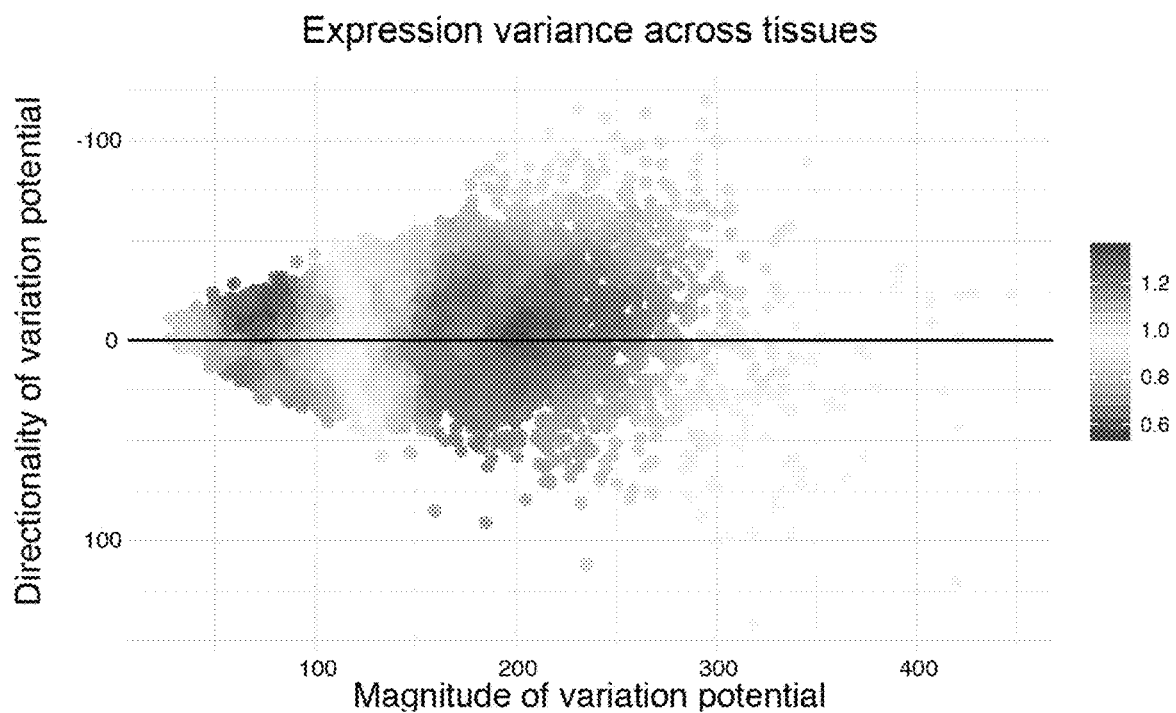
Figure 36:
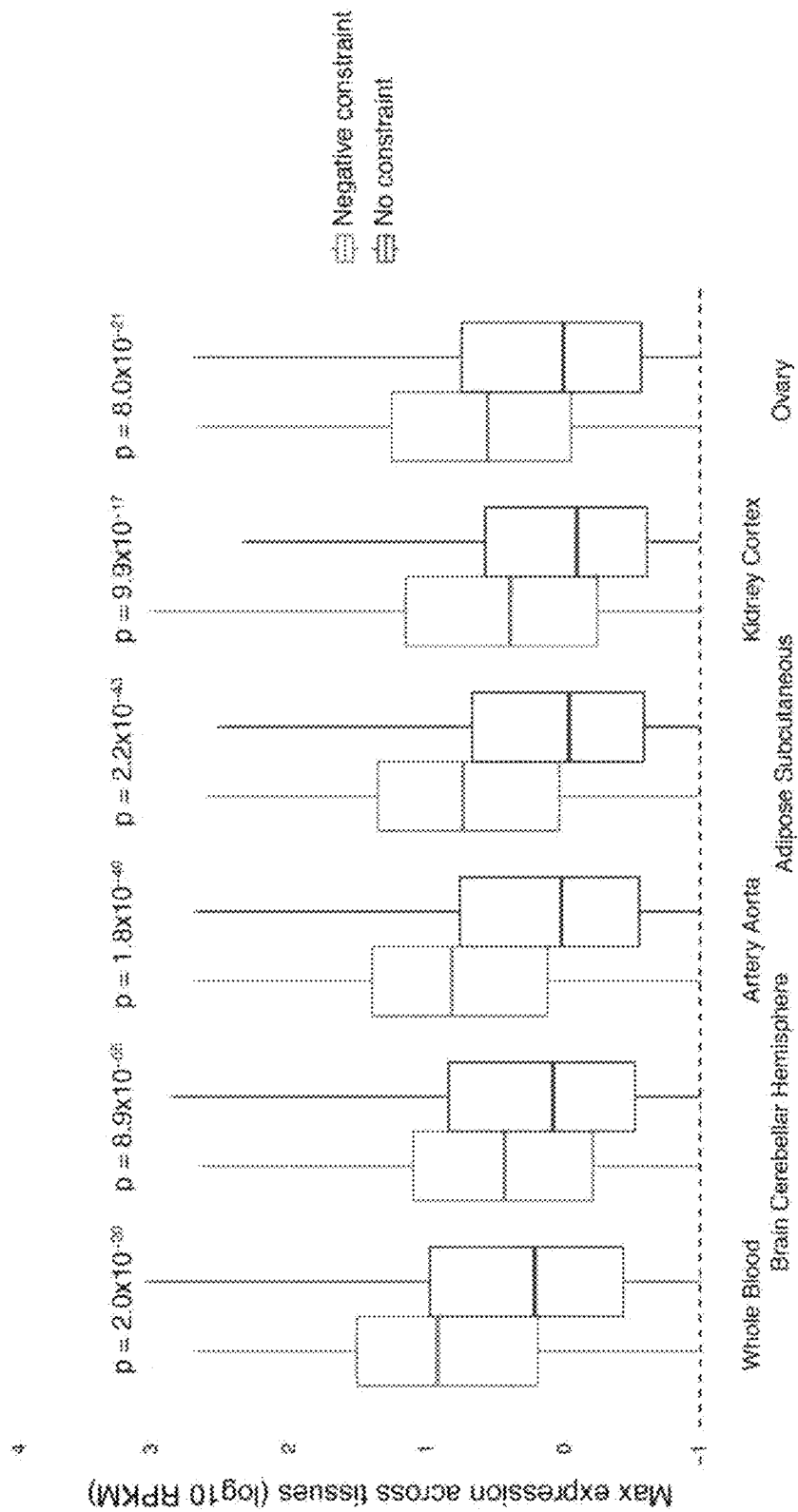
FIG. 36 provides a data graph that shows strong positive variation potential predicts high expression in non-modeled tissues, generated in accordance with various embodiments of the invention.
Figure 37:
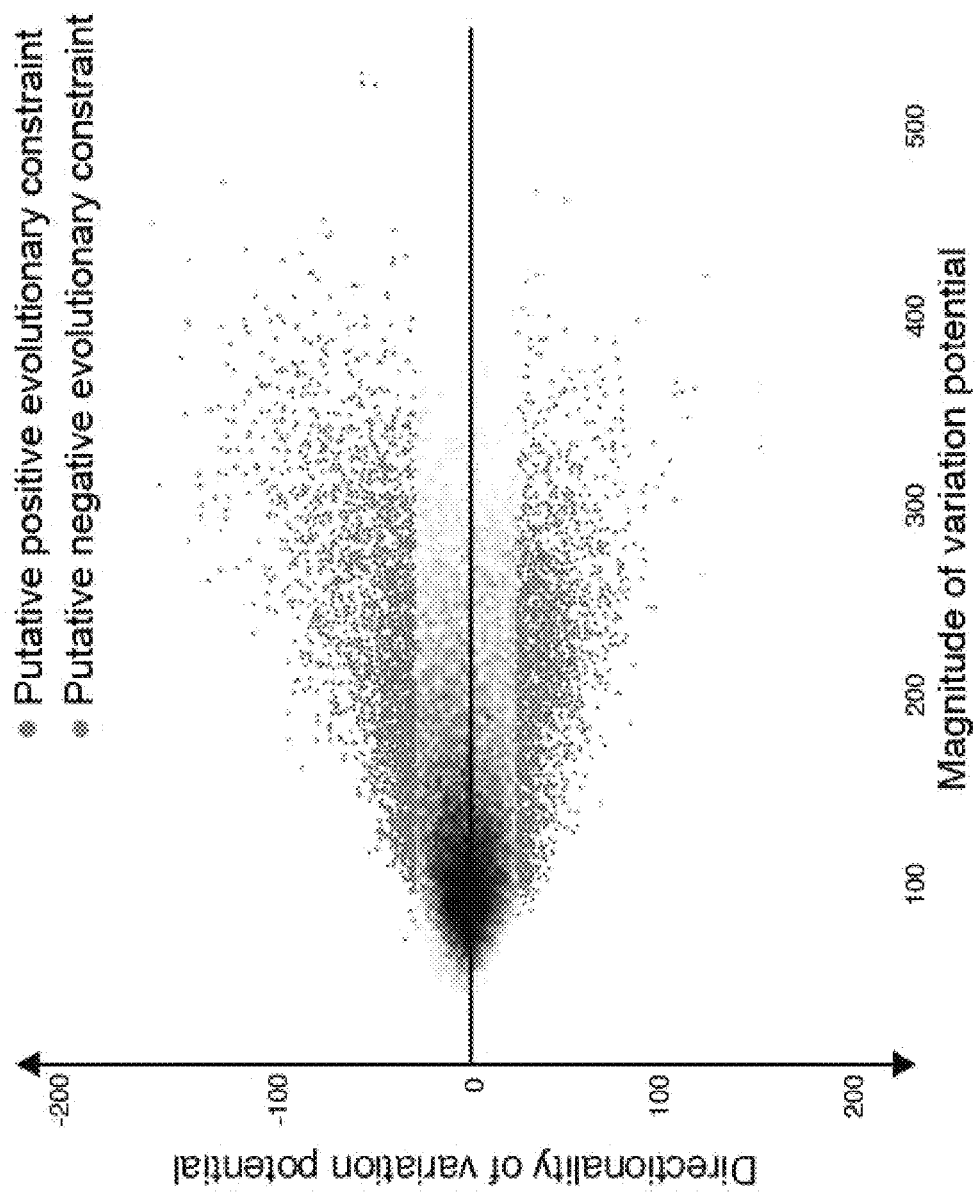
FIG. 37 provides a data graph that show inference of genes with putative directional evolutionary constraints from variation potentials, generated in accordance with various embodiments of the invention.

It was observed that tissue-specific variation potential of a gene is highly predictive of expression properties for that gene. Specifically, ExPecto can predict both whether a gene is ubiquitous versus tissue- or condition-specific and whether a gene is active or repressed (FIGS. 32 to 35, See Supplementary Data 2 of J. Zhou, et al., *Nat. Genet.* 50(8), 1171-1179 (2018)). Genes with low VP magnitude are characteristically ubiquitously expressed genes and often involved in essential cellular processes (e.g., splicing, translation, protein folding, and energy metabolism) (FIG. 33). In contrast, genes with high VP magnitude are tissue-specific (e.g., synaptic transmission genes) or condition-specific (e.g., innate immune response genes) (FIGS. 34 & 35). Among non-ubiquitous genes, VP's directionality (positive/negative cumulative mutation effect) in a given tissue predicts a gene's activity status: negative VP predicts actively expressed genes and positive VP indicates repressed expression in the modeled tissue (FIGS. 34 & 35). For example, in brain tissue, synaptic transmission genes have negative VP and are thus predicted to be actively expressed. On the contrary, in non-neural tissues, synaptic transmission genes have positive VP and are thus predicted to be repressed (as in FIG. 32) (See Supplementary Data 2 of J. Zhou, et al., *Nat. Genet.* 50(8), 1171-1179 (2018)). In a given tissue, genes with strong positive predicted VP indeed appear to be repressed, as they are expressed significantly higher in other tissues compared to genes with similar expression level but low VP magnitude (analysis based on GTEx, FIG. 36). Thus, variation potentials are not simply reflecting the magnitude of gene expression, but inferring expression properties from sequence.

Figure 38:
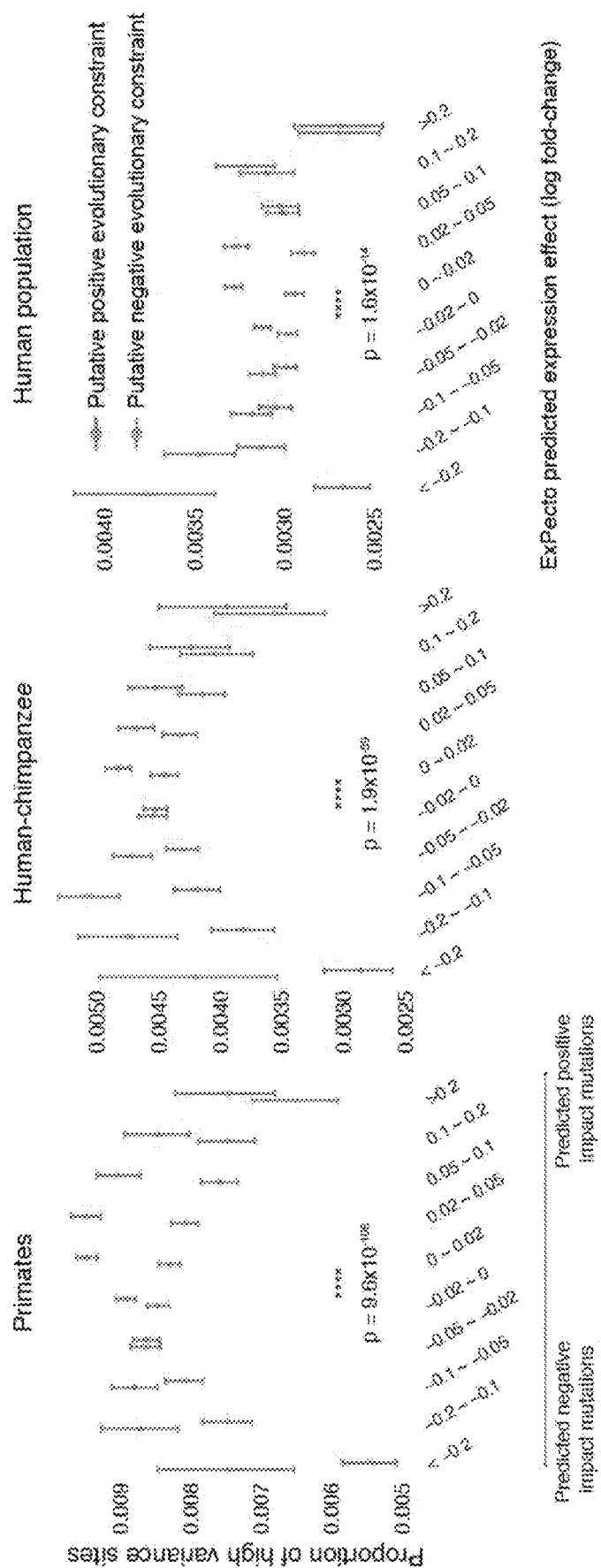
FIG. 38 provides data graphs that show evolution and population signatures have differential selective pressure for mutations in putative positive and negative constraint genes across evolutionary time scales, generated in accordance with various embodiments of the invention.
Figure 40:
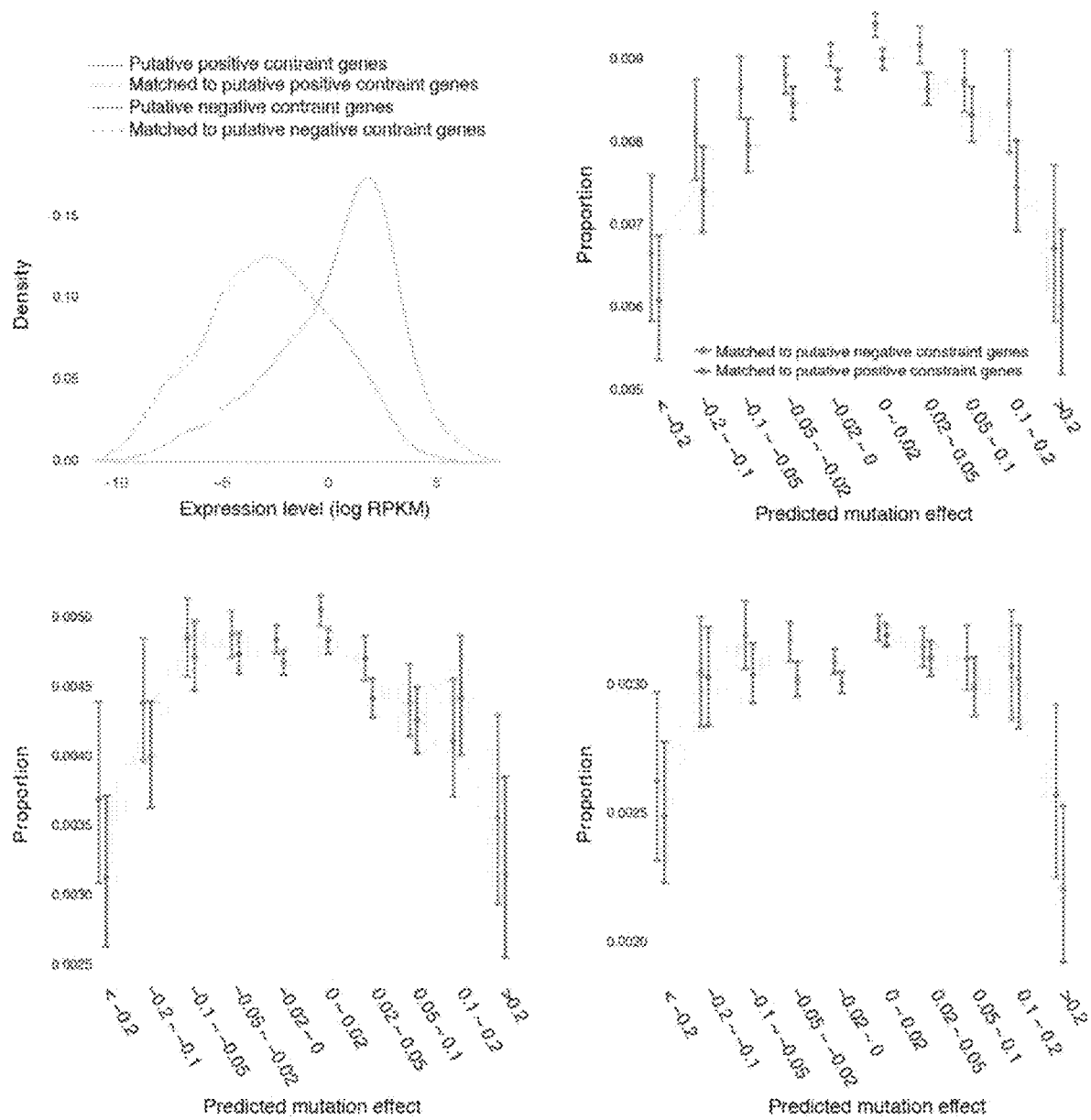
FIG. 40 provides data graphs that show divergent selectin signature for putative positive and negative constraint genes are not due to gene expression levels, generated in accordance with various embodiments of the invention.
Figure 41:
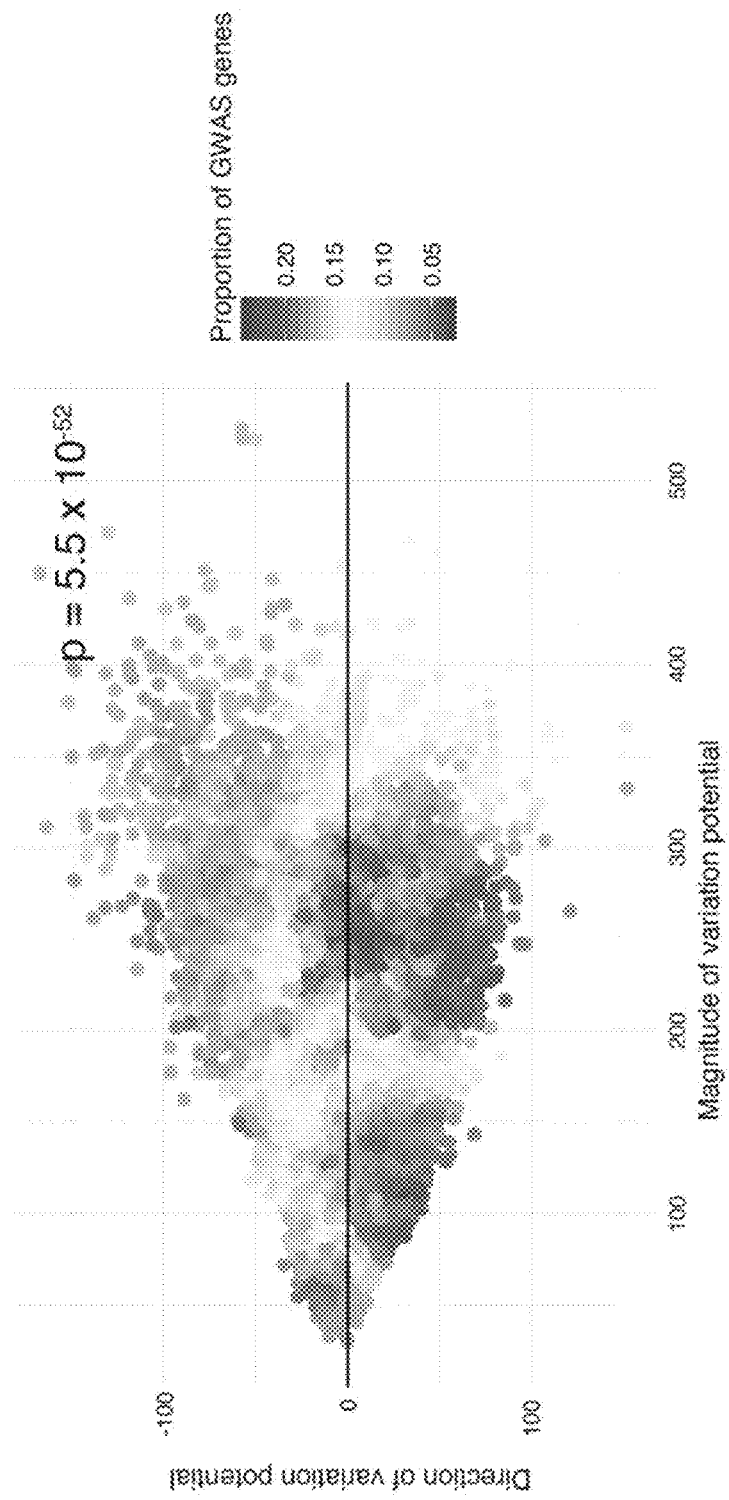
FIG. 41 provides a data graph that shows GWAS disease genes are enriched in high variation potential magnitude genes, generated in accordance with various embodiments of the invention.

It is hypothesized that a connection between variation potentials and expression properties of genes is imposed by evolutionary constraint. Specifically, it is proposed that genes strongly enriched with mutations of predicted negative effects are under positive evolutionary constraint (i.e., decreasing expression of that gene is deleterious) and vice versa (FIGS. 32 third panel, 37 to 39). Supporting this differential evolutionary constraints hypothesis, both variant allele frequencies in human populations and evolutionary conservation evidence supports divergent selection signatures for genes with putative positive and negative constraints ($p<1.6\times10^{-14}$ in all cases by two-sided Wald test with logistic regression on coefficient of interaction term). Specifically, for putative positive constraint genes, variant sites predicted to decrease expression have lower allele frequency and higher evolutionary conservation, as compared to negative constraint genes, and vice versa (FIG. 38). These divergent selection signatures are not simply driven by gene expression levels, because randomly selecting genes with matching expression levels do not show differential selection (FIG. 40). Moreover, genes with stronger inferred evolutionary constraints are significantly more enriched in GWAS disease genes ($p=6.1\times10^{-53}$ two-sided Wald test with logistic regression), indicating that changes in expression of these genes are more likely to lead to adverse consequences (FIG. 41).

With the inference of putative evolutionary constraints, key components for a regulatory disease mutation analysis framework that addresses both the impact of a variant on gene expression and the fitness impact of expression alterations are portrayed (FIG. 32). Recognizing regulatory disease mutations is very challenging because both of these problems are difficult to address experimentally. ExPecto's computational sequence-based approach addresses these problems genome-wide, even for mutations that have not been previously observed experimentally.

The ability of ExPecto to predict disease risk ab initio from sequence was assessed. At the individual variant level, whether a specific sequence alteration is likely to be deleterious or protective via integrating the expression effect and variation-potential-based constraint directionality through the constraint violation score was predicted. For example, if a variant causes a positively constrained highly expressed gene to substantially decrease expression, it is likely to be deleterious (FIG. 32 fourth panel). The predictions were then evaluated on the curated pathogenic regulatory mutations in human gene mutation database (HGMD) and the prioritized putative causal LD SNPs derived from GWAS catalog.

Most of the strong ExPecto predicted effect mutations from HGMD are predicted to decrease expression (FIG. 42), and correspondingly, all of them are near genes with putative positive evolutionary constraints as would be expected based on the findings described herein. Positive constraints are also consistent with the current understandings of these diseases as caused by deficiency of certain proteins, such as coagulation factor genes F7 and F9 for factor VII deficiency and Hemophilia B respectively; PROC and PROS1 genes for blood clotting disorders caused by protein C deficiency and protein S deficiency; APOA1 and LDLR for hypolipoproteinemia and hypercholesterolemia caused by apolipoprotein deficiency and decreased receptor-mediated endocytosis of LDL cholesterol deficiency respectively. UNC13D, essential for intracellular trafficking and exocytosis of lytic granules is associated with hemophagocytic lymphohistiocytosis type 3. Decreased expression of the BTK gene, an essential gene for B cell development and maturation, causes agammaglobulinemia. HNF1A mutation is well known as a major cause for maturity onset of diabetes (MODY) and considered important in beta-cell differentiation.

Figure 42:
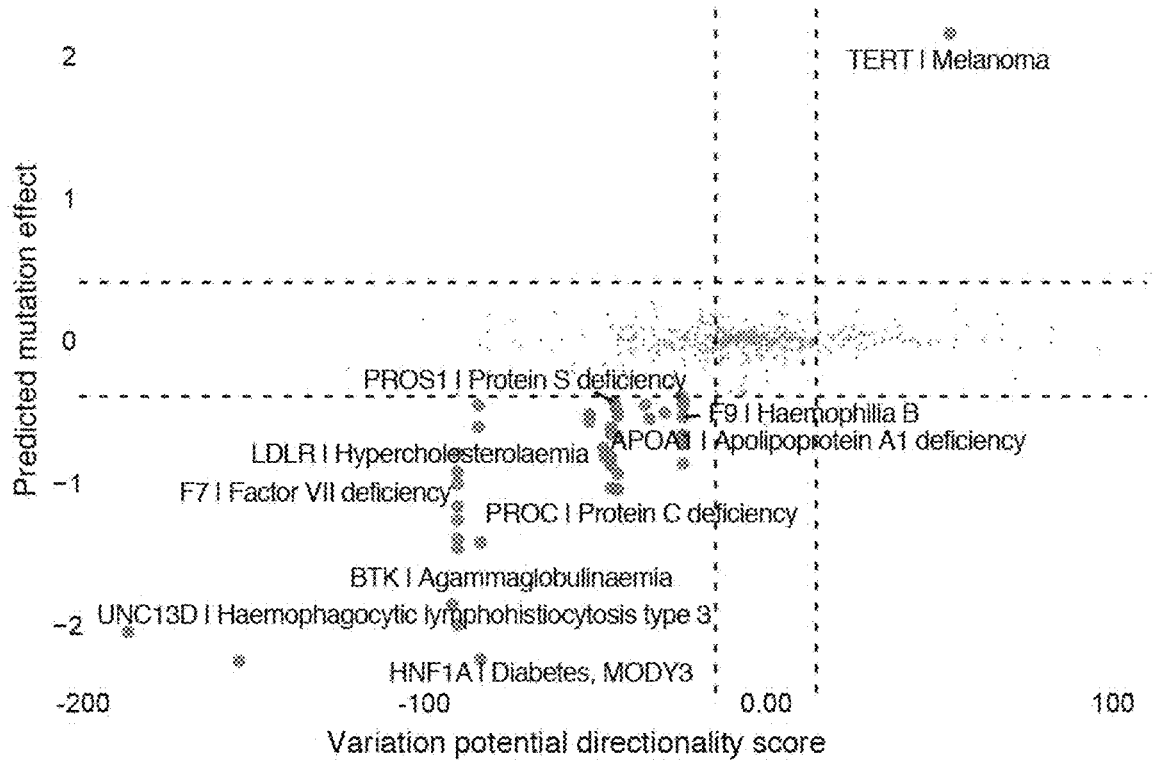
FIGS. 42 and 43 provide data graphs that show ab initio prediction of allele-specific disease risk integrating predicted expression effects and inferred evolutionary constraints, generated in accordance with various embodiments of the invention.

Only one HGMD disease mutation was predicted to strongly increase transcriptional activity and it is near a gene with putative negative constraints in all tissues, TERT (FIG. 42). TERT encodes telomerase reverse transcriptase, and overexpression of TERT thus supports unconstrained proliferation. Indeed, mutations in the TERT promoter were found to be highly recurrent in 71% of melanoma samples, as well as in many other cancer types including bladder and central nervous system cancers, and many of these mutations generate new ETS binding sites and increase transcriptional activity in reporter assays, consistent with our predictions. Note that even though HGMD disease mutations are known to be deleterious, these results demonstrate that ExPecto can correctly predict the disease allele versus the non-disease allele without any prior knowledge of disease association.

Figure 43:
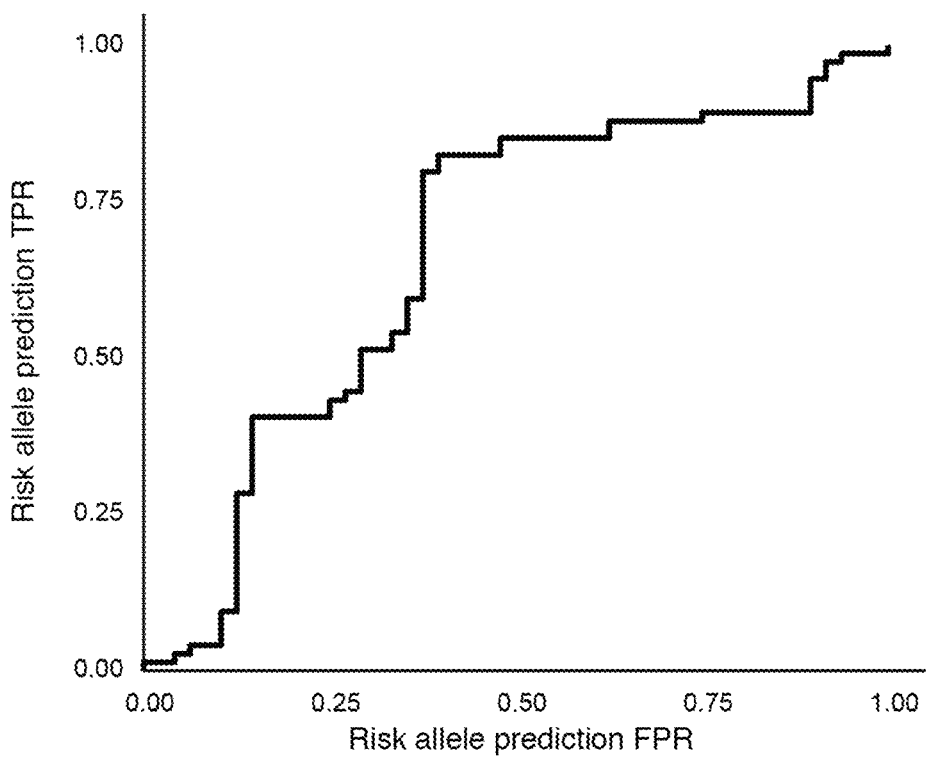

To assess the potential for ExPecto to predict disease risk for relatively common variants in the population, whether constraint violation scores were predictive for GWAS risk loci was evaluated. Positive violation scores suggest the alternative allele is likely more deleterious while a negative violation score suggests the reference allele is likely more deleterious. This GWAS evaluation standard directly includes both deleterious and protective variants (risk alleles are reference alleles for 37 loci, alternative alleles for 63 loci). ExPecto is significantly predictive (p=0.002, Wilcoxon rank sum test, AUC=0.67, FIG. 43, See Supplementary Data 3 of J. Zhou, et al., *Nat. Genet.* 50(8), 1171-1179 (2018)) of the known risk alleles detected from GWAS studies. This evaluation thus demonstrates that predicted effects that violate inferred constraints are predictive of risk alleles in GWAS, indicating that ExPecto can predict which allele is deleterious or protective without any prior variant-disease association information. Together these results suggest this approach as a large-scale prediction of disease risks, which will be especially useful for interpreting the enormous amount of potential disease mutations for which there is with little or no prior knowledge.

Detailed Methods

ExPecto framework architecture: The ExPecto sequence-based expression prediction framework includes three components that act sequentially (FIG. 7). First, a deep neural network epigenomic effects model scans the long input sequence with a moving window and outputs predicted probabilities for histone marks transcription factors, and DNase hypersensitivity profiles at each spatial position. Then a series of spatial transformation functions summarize each predicted spatial pattern of chromatin profiles to generate a reduced set of spatially transformed features (FIG. 8). Last, the spatially-transformed features are used to make tissue-specific predictions of expression for every gene by regularized linear models.

The first component of ExPecto uses a deep convolutional neural network to transform genomic sequences to epigenomic features. The approach generates a cell-type specific model for 2,002 genome-wide histone marks, transcription factor binding and chromatin accessibility profiles (based on training data from ENCODE and Roadmap Epigenomics projects, See Supplementary Data 4 of J. Zhou, et al., *Nat. Genet.* 50(8), 1171-1179 (2018)) (for more on ENCODE and Roadmap, see N. de Souza, *Nat. Methods* 9, 1046-1046 (2012) & B. E. Bernstein *Nat. Biotechnol.* 28, 1045-8 (2010), the disclosures of which are each incorporated herein by reference). Specifically, the model architecture has an extended number of convolution layers for increased model depth, broader genomic context via increased window size (2000 bp), and the model was trained to predict 2002 regulatory features for over 200 cell types (see model architecture below). Critically, this deep learning model does not use any nucleotide variant data for training. The deep convolutional neural network model predicts epigenomic features of a 200 bp region, while also using the 1800 bp surrounding context sequence. For each Pol II-transcribed gene, surrounding its representative transcriptional start site (TSS, see the 'Identification of representative transcription start sites' section below), the deep convolutional neural network model scans the genomic sequence between +20 kb upstream and −20 kb downstream to predict spatial chromatin organization patterns using a moving window with 200 bp step size, yielding 200 spatial bins with a total number of 400400 features.

The model architecture is specified as the following:
Input (Size: 4 bases×2000 bp)=>
(Layer 1): Convolution(4->320, kernel size=8)
(Layer 2): ReLU
(Layer 3): Convolution(320->320, kernel size=8)
(Layer 4): ReLU
(Layer 5): Dropout(Probability=0.2)
(Layer 6): Max pooling(pooling size=4)
(Layer 7): Convolution(320->480, kernel size=8)
(Layer 8): ReLU
(Layer 9): Convolution(480->480, kernel size=8)
(Layer 10): ReLU
(Layer 11): Dropout(Probability=0.2)
(Layer 12): Max pooling(pooling size=4)
(Layer 13): Convolution(480->640, kernel size=8)
(Layer 14): ReLU
(Layer 15): Convolution(640->640, kernel size=8)
(Layer 16): ReLU
(Layer 17): Dropout(Probability=0.5)
(Layer 18): Linear(67840->2003)

(Layer 19): ReLU
(Layer 20): Linear(2003->2002)
(Layer 21): Sigmoid
=>Output (Size: 2002 epigenomic features) ReLU indicates the rectified linear unit activation function. Sigmoid indicates the Sigmoid activation function. Notations such as '4->320' indicate the input and output channel size for each layer. When not indicated, the output channel size is equal to the input channel size.

The second component of ExPecto is the spatial transformation module that reduces the dimensionality of the learning problem by generating spatially-transformed features (FIG. 8). The spatial transformation module reduces the input dimensionality with ten exponential functions weighting upstream and downstream regions separately, with weights based on relative distance to TSS (transformed features with higher decay rate are more concentrated near TSSs). This effectively reduces the number of features 20 fold to 20020. The exponential functions were prespecified (based on empirical selection) and not learned during training. This spatial feature transformation followed by learning linear model retains the flexibility of learning spatial patterns, which is equivalent to learning a smooth nonlinear spatial pattern function $f$ constrained to the space of linear combinations of basic functions corresponding to the feature transformations.

Figure 44:
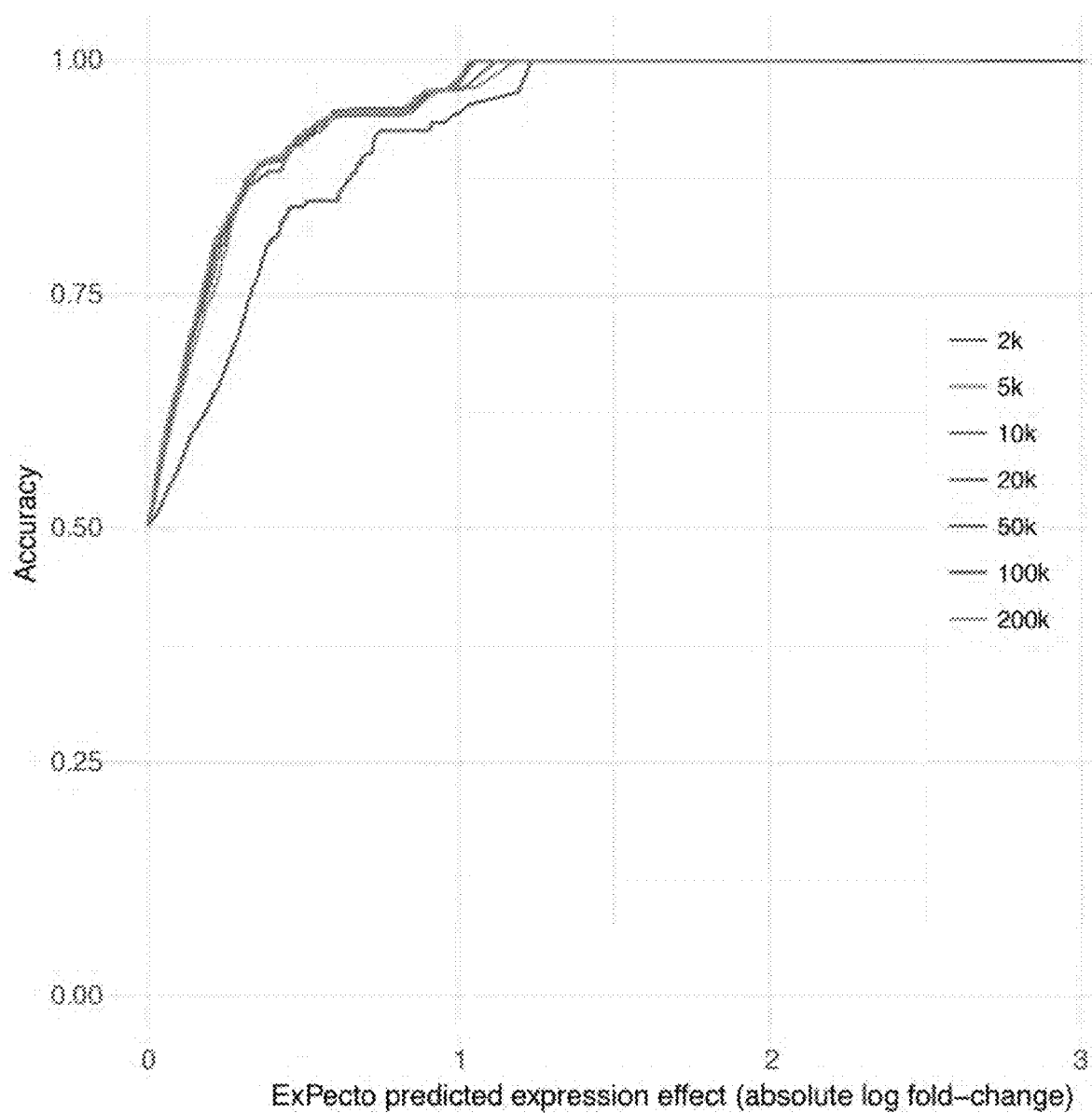
FIG. 44 provides a data graph that compares ExPecto eQTL prediction performance across models trained with different sequence window sizes, generated in accordance with various embodiments of the invention.

Finally, to make tissue-specific expression predictions, spatially-transformed features are used to predict gene expression levels for each tissue (quantified by log RPKM) with L2-regularized linear regression models fitted by gradient boosting algorithm. Specifically, the full models including both spatial transformation and linear models are specified as below.

$$\text{expression} = \sum_{d \in D} \sum_{i} p_{id}$$

$$\left[ \sum_{k} 1(t_d < 0) \, \beta^{up}_{ik} e^{-a_k \lfloor \frac{|t_d|}{200bp} \rfloor} + \sum_{k} 1(t_d > 0) \beta^{down}_{ik} e^{-a_k \lfloor \frac{|t_d|}{200bp} \rfloor} \right]$$

where $p_{id}$ is the predicted probabilities or chromatin feature i at region d relative to the TSS, and D represents the set of 200×200 bp spatial bins within 20 kb of the TSS. 1 represents the indicator function which equals one when the specified condition is satisfied and zero otherwise. $t_d$ represents the mean distance of region d to the TSS. For example, the −200 bp to 0 bp bin has a distance of −100 bp and the −400 bp to −200 bp bin has a distance of −300 bp. $\beta^{up}_{ik}$ and $\beta^{down}_{ik}$ are the learned expression model coefficients of chromatin feature i and exponential function index k for upstream and downstream regions respectively. The decay constant for exponential function k is indicated by $a_k$, where a={0.01, 0.02, 0.05, 0.1, 0.2}. Note that model coefficients $\beta^{up}_{ik}$ and $\beta^{down}_{ik}$ are shared across spatial bins indexed by d due to spatial transformation, thus significantly decreasing the number of fitted parameters (by 20 fold) and reducing overfitting. All hyperparameters of ExPecto are chosen by empirical evaluations, including the number and values of exponential terms, model design, and window sizes, while all the neural network model weights and linear model coefficients are learned from data. The +/−20 kbp (40 Kbp) window size around the TSS maximizes ExPecto accuracy. While smaller windows decrease prediction performance, increasing the window size to 50 kb, 100 kb or even 200 kb gives negligible performance gain (FIG. 44).

Application of ExPecto for sequence-based gene expression level prediction across tissues: ExPecto models can be trained on any expression profile. Here, 218 tissue expression profiles from GTEx, Roadmap epigenomics and ENCODE projects were used. A pseudocount was added before log transformation (0.01, except for 0.0001 for GTEx tissues (which were averaged across individuals) due to high coverage from pooling multiple samples). The linear expression models were trained with L2 regularization parameter lambda=100, shrinkage parameter eta=0.01 and basescore=2 for 100 rounds. The training and prediction time of ExPecto is detailed in Table 2.

The gene-wise expression prediction performance was evaluated on whole chromosome holdout of chr8 (990 genes), which was withheld at all stages of the ExPecto training (sequences were not used for training either the linear expression models or the neural network regulatory effects model). A whole chromosome holdout was tested to provide a more conservative evaluation and minimize overlap of regulatory regions. To further minimize the possibility of overfitting through homology, all chr8 genes with paralogs on other chromosomes were removed, which did not negatively affect performance (Spearman correlation 0.819 for all 990 chr8 genes, 0.821 for after removal of 184 paralogous genes).

For interpretation of tissue-specific signals captured by the models, the most informative cell type-specific sequence features from expression models were extracted as follows:

$$\frac{1}{n_k} \sum_{k} \beta^c_{ik} - \frac{1}{n_k n_{cells}} \sum_{c'} \sum_{k} \beta^{c'}_{ik}$$

$\beta^c_{ik}$ represent in the coefficient for chromatin feature i, exponential function k in cell type/tissue c. $n_k$ represents the number of exponential functions ($n_k$=10 in this case, considering both upstream and downstream coefficients), and $n_{cells}$ represents the number of all cell type/tissue models. c' is index for cell type/tissues. To enable comparison across features from different datasets, models retrained with a uniform pseudocount of 0.0001 were used for all tissue or cell types. The top features with higher than tissue-average coefficients were then selected.

Variant expression effect prediction: Gene expression effect is naturally estimated by the difference of predicted expression levels for reference and alternative allele, which is measured by the predicted log fold change. As the expression effect models are linear combinations of regulatory feature predictions, expression effect prediction computation can be simplified to a function of the variant chromatin effects p and distance to TSS t $$\text{effect}(p, t) = \sum_{\delta \in \Delta} \sum_{i} \left( p^{alt}_{i\delta} - p^{ref}_{i\delta} \right)$$

$$\left[ \sum_{k} 1(t_d < 0) \, \beta^{up}_{ik} e^{-a_k \lfloor \frac{|t_d|}{200bp} \rfloor} + \sum_{k} 1(t_d > 0) \beta^{down}_{ik} e^{-a_k \lfloor \frac{|t_d|}{200bp} \rfloor} \right]$$

where $p^{ref}_{i\delta}$ and $p^{alt}_{i\delta}$ are the predicted probabilities for chromatin feature i with reference allele or alternative allele at position δ relative to the variant position, $\beta^{up}_{ik}$ and $\beta^{down}_{ik}$ are the expression model coefficients of chromatin feature i and exponential function index k for upstream and downstream variants, respectively. The decay constant for exponential function k is indicated by $a_k$ and the distance to TSS is indicated by t. Notably the predicted variant regulatory effect includes both effects at the variant site and at adjacent positions (as long as the variant is within range of 2000 bp context sequence window for that region), thus the variant expression effect considers regulatory effects in 9 positions specified by:
$\Delta$={0 bp, −200 bp, −400 bp, −600 bp, −800 bp, +200 bp, +400 bp, +600 bp, +800 bp}.

For small INDELs, the alternative allele sequence were compensated or truncated equally on both sides to total 2000 bp.

Evaluation of ExPecto tissue-specific expression effect predictions: The GTEx v6 eQTLs, the 1000 Genomes phase 3 variants, and GWAS Catalog data were downloaded. HGMD regulatory mutations were from HGMD professional version 2014.4 and filtered to category DM, which represents "disease-causing/pathological" mutations reported to be disease causing in the original literature.

The in vitro reporter assay eQTL effects were predicted with modifications for adapting to the difference between in vitro reporter assay and in vivo expression, as only a short element is cloned to a fixed position upstream of a reporter gene in reporter assay. Specifically, regulatory effect models trained on 230 bp input window were used instead of 2000 bp, and only the in-place chromatin effect but not effect on adjacent regions were computed, as these sequences were not cloned to the reporter vector. The position relative to TSS is fixed at −100 bp.

Figure 45:
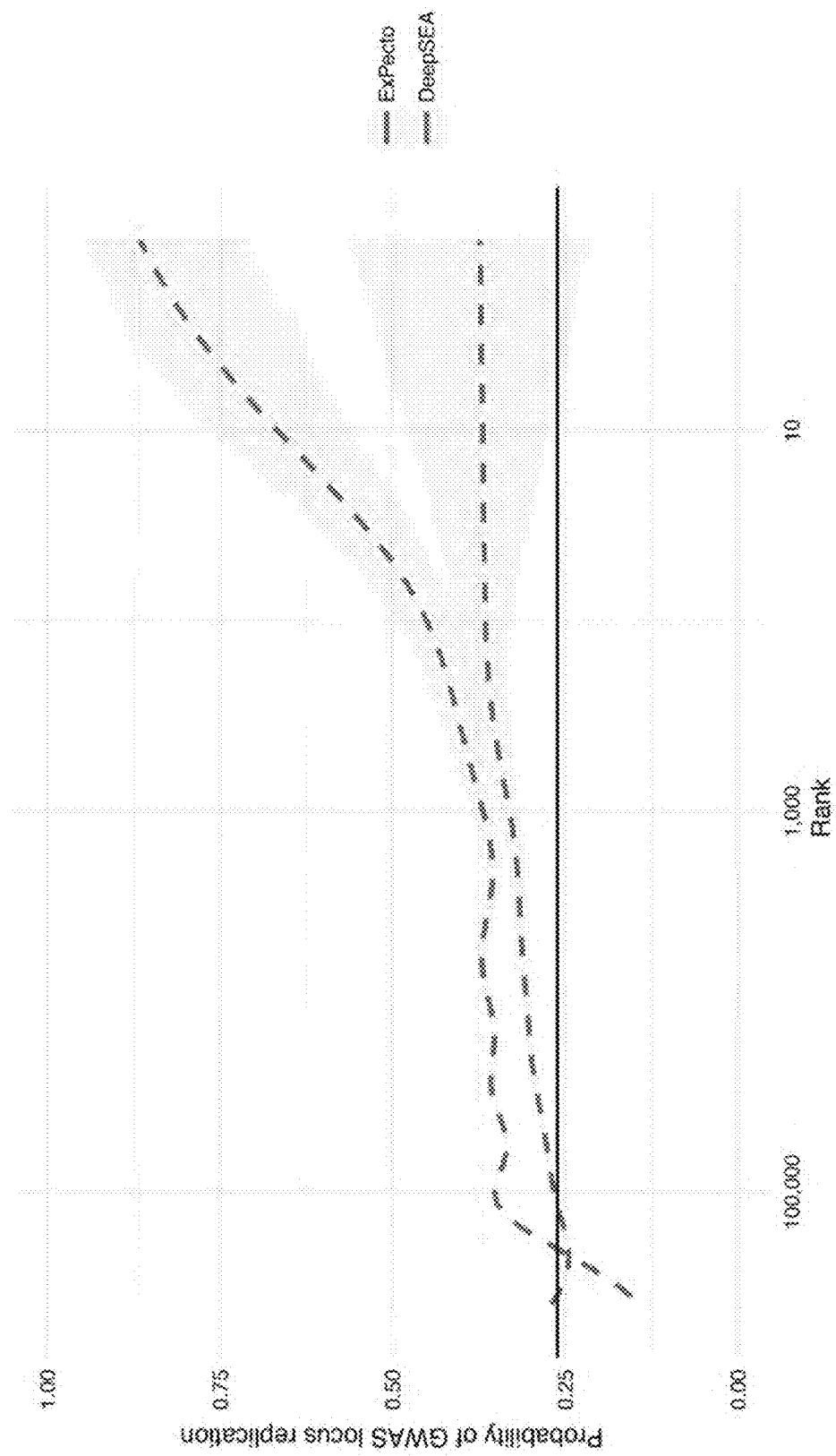
FIG. 45 provides a data graph that compares ExPecto and a previously generated model (DeepSEA) to prioritize GWAS variants, generated in accordance with various embodiments of the invention.

ExPecto prioritization of GWAS loci was evaluated by examining their replication of prioritized loci across studies. In FIG. 45 ExPecto was compared to DeepSEA (which predicts just the epigenomic component of the variant effect) in this task. ExPecto predicts variant effects on gene expression while DeepSEA can identify variant effects that do not lead to significant expression change (for more on DeepSEA, see J. Zhou & O. G. Troyanskaya, *Nat. Methods* 12, 931-4 (2015), the disclosure of which is incorporated herein by reference).

Computation of GWAS linkage disequilibrium SNPs: To systematically screen for SNPs in linkage disequilibrium with the reported GWAS lead SNPs from GWAS catalog, linkage disequilibrium was computed for all 88 million variants in 1000 Genomes phase 3 genotype data, which includes >99% of SNP variants with a frequency of >1% for a variety of ancestries. Linkage disequilibrium between SNPs in five populations EAS, SAS, AMN, AFR and EUR were computed with PLINK v1.90b. In total, 390,085 variants in LD $r^2$>0.75 were found with 15571 distinct GWAS catalog reported variants. ExPecto was then used to systematically predict expression effects for all LD variants to their nearest TSS.

Experimental validation of prioritized candidate GWAS causal SNPs: The top three ExPecto-prioritized variants that had no prior evidence for functionality were experimentally validated, each of which were associated with four immune-related diseases in seven GWAS studies. Specifically, a luciferase assay was used to compare the ability of risk versus non-risk alleles to drive expression for the above ExPecto prioritized variants and the seven lead SNPs reported by the corresponding GWAS studies.

All genomic sequences were retrieved from hg19 human genome assembly. For each risk allele (reference or alternative), Genewiz synthesized a 260 nucleotide fragment: 230 was human genomic sequence and 15 nucleotides matched each flank of the plasmid cloning sites (Table 3). Each fragment was cut with KpnI and BglII and cloned into pGL4.23 (minP firefly luciferase vector) (Promega) cut with the same enzymes. For luciferase assay, $2 \times 10^4$ BE(2)-C cells were plated in 96-well plates, and 24 hours later transfected with Lipofectamine 3000 (L3000-015, Thermofisher Scientific) and 75 ng of variant-containing pGL4.23 plasmid (Table 3), and 4 ng of pNL3.1 NanoLuc plasmid, for normalization of transfection conditions. 42 hours after transfection, luminescence was detected with the Promega NanoGlo Dual Luciferase assay system (N1630) and BioTek Synergy plate reader. Four to six replicates per variant were tested in each experiment. The experiment was performed 2-5 times for the variants. For each sequence tested, the ratio of firefly (variant) luminescence to NanoLuc (transfection control) luminescence was calculated and then normalized to empty vector. Statistics were calculated by combining fold over EV values from each biological replicate.

Systematic profiling of variation potential and evolutionary constraints by in silico mutagenesis: Over 140 million possible single nucleotide substitution variations were systematically predicted across all human promoters within 1 kb of the representative TSS on both sides. Gene-wise variation potentials were summarized by two measures: directionality, which is computed as the sum of predicted log fold-changes for all mutations per gene, and magnitude, which is computed as the sum of all absolute predicted log fold-changes. It was found that genes with negative variation potential directionality (i.e., mutations tend to cause a decrease in tissue-specific expression) are actively expressed in the modeled tissue (see FIGS. 33 to 35). It was inferred that these genes are under positive evolutionary constraint, and thus are vulnerable to inactivating mutations. On the other hand, it was found that expression of genes with positive variation potential (i.e., mutations cause an increase in tissue-specific expression) is repressed in the modeled tissue (see FIGS. 33 to 35). It was inferred that these genes are under negative evolutionary constraint, and thus are vulnerable to activating mutations. Note that evolutionary constraints cannot simply be inferred from gene expression levels (FIG. 40).

Figure 39:
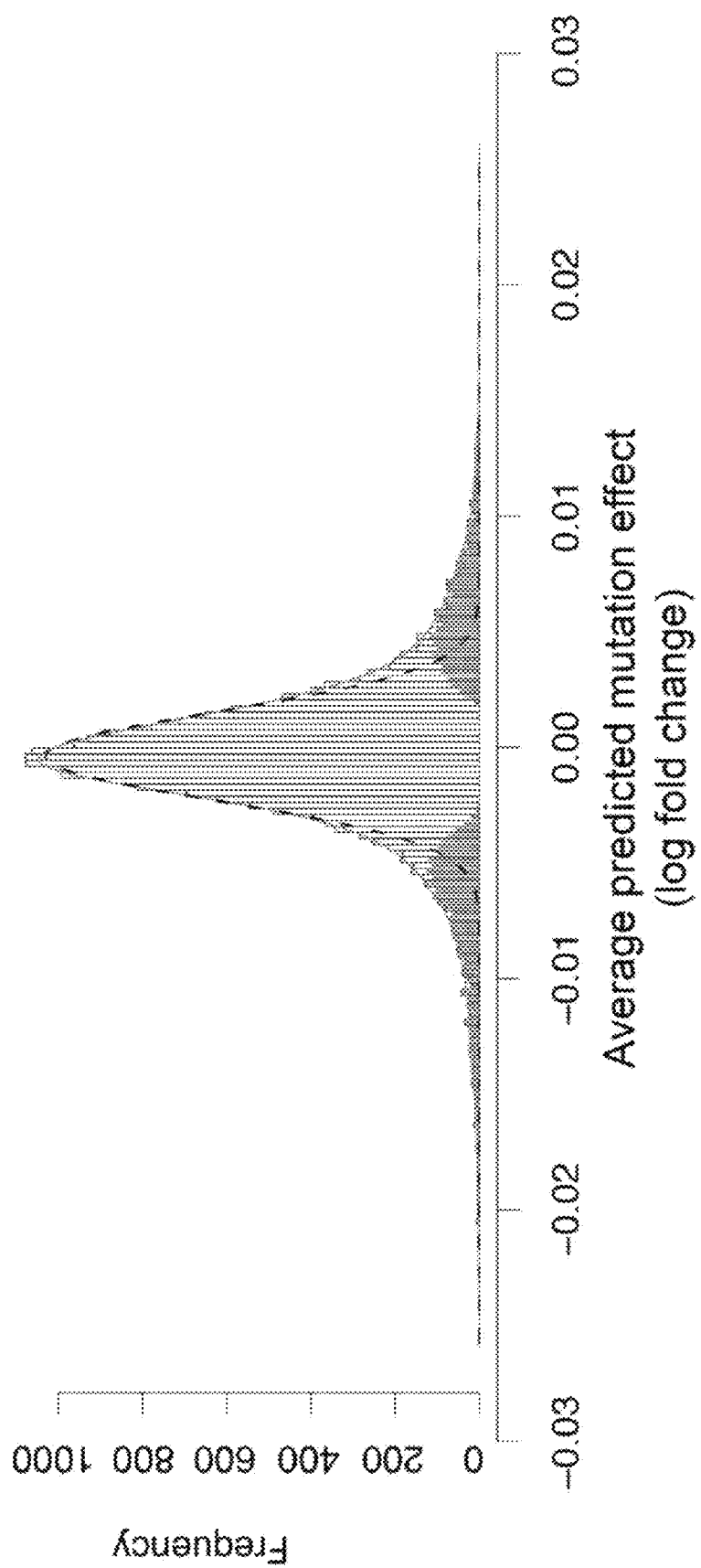
FIG. 39 provides a data graph that shows inference of genes with putative directional evolutionary constraints from variation potentials, generated in accordance with various embodiments of the invention.

The directionality score was used to measure the tendency of the potential mutation effect to be biased toward positive or negative, which indicates negative and positive evolutionary constraints, respectively (FIG. 39). The distribution of mean predicted mutation effects across genes was modeled as a mixture of a Gaussian null distribution, a positive constraint component and a negative constraint component. While the true null distribution is unknown, a conservative estimate of empirical null distribution can be obtained by assuming the other components are only observed at the two tails and estimating a Gaussian distribution using central quantiles of the data, similar to the idea used for measuring local FDR. The empirical null distribution was fit with the truncated Gaussian MLE method implemented in the locfdr R package (see B. Efron, *Ann. Stat.* 35, 1351-1377 (2007), the disclosure of which is incorporated herein by reference). With empirical null distribution estimation and density estimation of overall distribution of gene-wise average predicted effects, one can then compute probabilities of genes belonging to the positive or negative constraint components. Probability >0.5 for each component is used for assigning genes to putative positive or negative evolutionarily constrained genes.

Analysis of conservation and allele frequency for variants: For estimating recent divergence in the modern human population, allele frequencies among the 1000 Genomes project phase 3 individuals were used. For estimating divergence from human-chimpanzee common ancestor, the proportion of divergent sites was computed from the high confidence divergence sites from. For estimating divergence among 10 primate species (including humans), proportion of accelerated evolution sites based on primates phylop scores was computed. Accelerated evolution sites were decided with the threshold of phyloP <−2.3 which corresponds to p-value<0.005 for accelerated evolution.

Ab initio inference of disease risk alleles: The ExPecto-prioritized GWAS LD variants were used (as described above) for risk allele prediction. GWAS LD variants with $r^2>0.75$ were included in a matched 1000 Genomes population, and variants for which the risk allele is ambiguous (different GWAS studies pointing to conflicting risk alleles) were excluded. Only GWAS studies for disease or disease related traits were included. The constraint violation score was computed as the product of the predicted variant effect of the prioritized LD variant and the variation potential directionality score of the nearest TSS. The median constraint violation score across all non-cancer tissue or cell types for each variant was used.

Figure 46:
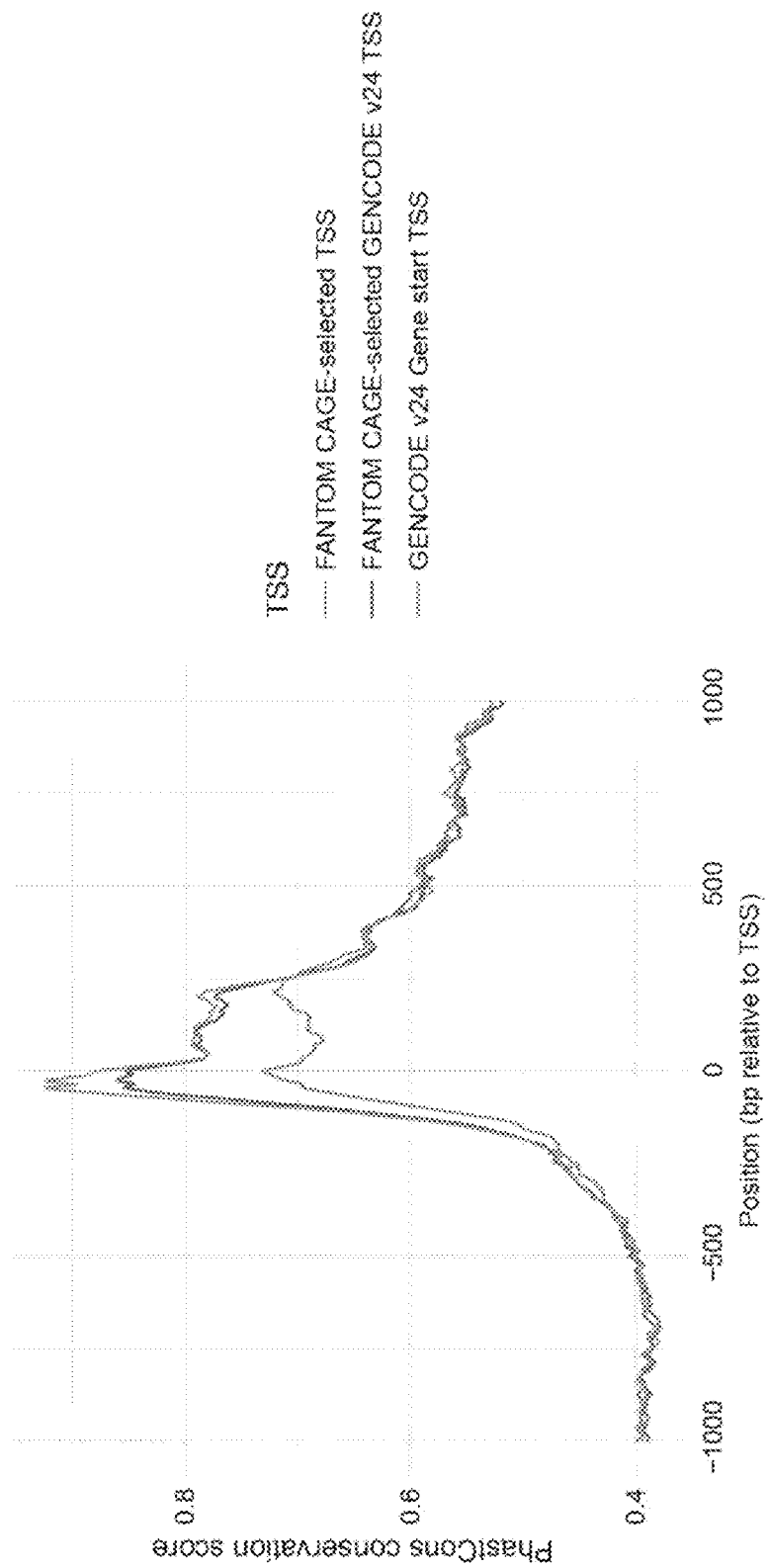
FIG. 46 provides a data graph that shows evolutionary conservation of CAGE-based representative transcription start sites and gene start sites, generated in accordance with various embodiments of the invention.

Identification of representative transcription start sites: Most expression profiling datasets were quantified to gene level, as it is often challenging to achieve accurate quantification of TSS expression level from short read sequencing. Even though training expression model should ideally utilize TSS-specific expression quantification, gene level expression measured by RNA-seq or microarray are usually a good approximation of transcription level from the representative TSS of each gene, and are usually measured with higher sequencing depth. A representative TSS was determined for each Pol 11 transcribed gene based on quantification of aggregated cap analysis of gene expression (CAGE) reads in the FANTOM5 project (see A. R. R. Forrest, et al., *Nature* 507, 462-470 (2014), the disclosure of which is incorporated herein by reference). Specifically, a CAGE peak is associated to a GENCODE gene if it is within 1000 bp from a GENCODE v24 annotated transcription start site (lifted to GRCh37 coordinates). Peaks within 1000 bp to rRNA, snRNA, snoRNA or tRNA genes were removed to avoid confusion. Next, we selected the most abundant CAGE peak for each gene, and took the TSS position reported for the CAGE peak as the selected representative TSS for the gene. For genes with no CAGE peaks assigned, the annotated gene was kept start position as the representative TSS. The selected TSSs showed significantly higher conservation level compared to the annotated gene start positions ($p=5.7\times10^{-8}$, FIG. 46).

Statistical analysis: Details of the statistical tests are specified in the associated text. Association between two variables is tested via linear regression (or logistic regression if one the variable is categorical) with the null hypothesis that the slope coefficient is zero. For comparing evolution and population genetics signatures between putative positive and putative negative constraint genes, the null hypotheses that the coefficient of the interaction term is zero was tested in a logistic regression model specified by the formula y~e+t+e·t, where y is a binary variable representing evolutionary or population genetic information about a site, e represents the ExPecto predicted expression effect, t represents the inferred putative constraint type, and e·t represents the interaction term.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

TABLE 1

Genes that Affect Drug Metabolism

| Medication | Gene(s) |
|---|---|
| abacavir | HLA-B |
| acenocoumarol | VKORC1, CYP2C9 |
| allopurinol | HLA-B |
| amitriptyline | CYP2C19, CYP2D6 |
| aripiprazole | CYP2D6 |
| atazanavir | UGT1A1 |
| atomoxetine | CYP2D6 |
| azathioprine | TPMT |
| capecitabine | DPYD |
| carbamazepine | HLA-A, HLA-B |
| carvedilol | CYP2D6 |
| cisplatin | TPMT |
| citalopram | CYP2C19 |
| clomipramine | CYP2C19, CYP2D6 |
| clopidogrel | CYP2C19 |
| clozapine | CYP2D6 |
| codeine | CYP2D6 |
| daunorubicin | RARG, SLC28A3, UGT1A6 |
| desflurane | CACNA1S, RYR1 |
| desipramine | CYP2D6 |
| doxepin | CYP2C19, CYP2D6 |
| doxorubicin | RARG, SLC28A3, UGT1A6 |
| duloxetine | CYP2D6 |
| enflurane | CACNA1S, RYR1 |
| escitalopram | CYP2C19 |
| esomeprazole | CYP2C19 |
| flecainide | CYP2D6 |
| fluorouracil | DPYD |
| flupenthixol | CYP2D6 |
| fluvoxamine | CYP2D6 |
| glibenclamide | CYP2C9 |
| gliclazide | CYP2C9 |
| glimepiride | CYP2C9 |
| haloperidol | CYP2D6 |
| halothane | CACNA1S, RYR1 |
| imipramine | CYP2C19, CYP2D6 |
| irinotecan | UGT1A1 |
| isoflurane | CACNA1S, RYR1 |
| ivacaftor | CFTR |
| lansoprazole | CYP2C19 |
| mercaptopurine | TPMT |
| methoxyflurane | CACNA1S, RYR1 |
| metoprolol | CYP2D6 |
| mirtazapine | CYP2D6 |
| moclobemide | CYP2C19 |
| nortriptyline | CYP2D6 |
| olanzapine | CYP2D6 |
| omeprazole | CYP2C19 |
| ondansetron | CYP2D6 |
| oxcarbazepine | HLA-B |
| oxycodone | CYP2D6 |
| pantoprazole | CYP2C19 |
| paroxetine | CYP2D6 |
| peginterferon alpha-2a | IFNL3 |
| peginterferon alpha-2b | IFNL3 |
| phenprocoumon | VKORC1, CYP2C9 |
| phenytoin | CYP2C9, HLA-B |
| propafenone | CYP2D6 |
| rabeprazole | CYP2C19 |
| rasburicase | G6PD |
| ribavirin | IFNL3, HLA-B |
| risperidone | CYP2D6 |
| sertraline | CYP2C19 |
| sevoflurane | CACNA1S, RYR1 |
| simvastin | SLCO1B1 |
| succinylcholine | CACNA1S, RYR1 |
| tacrolimus | CYP3A5 |
| tamoxifen | CYP2D6 |
| tegafur | DPYD |

TABLE 1-continued

Genes that Affect Drug Metabolism

| Medication | Gene(s) |
|---|---|
| thioguanine | TPMT |
| tolbutamide | CYP2C9 |
| tramadol | CYP2D6 |
| trimipramine | CYP2C19, CYP2D6 |
| tropisetron | CYP2D6 |
| venlafaxine | CYP2D6 |
| voriconazole | CYP2C19 |
| warfarin | CYP2C9, CYP4F2, VKORC1 |
| zuclopenthixol | CYP2D6 |

TABLE 2

ExPecto training and prediction time requirements.

| Task | Time | Hardware |
|---|---|---|
| ExPecto training: Regularized linear model (deep convolutional network and spatial transformation are precomputed and don't require retraining) | 8 min/ ExPecto model | Intel Xeon E7-4870 2.40 GHz |
| ExPecto prediction: Deep convolutional neural network | 0.06 s/ variant | NVIDIA Tesla P100 |
| ExPecto prediction: Spatial transformation and regularized linear models | 0.01 s/ variant × 218 ExPecto models | Intel Xeon E7-4870 2.40 GHz |

TABLE 3

Experimental Validation of Causal Variants

| Insert Name | Coord | Seq ID No. | rsID | Sequence | Allele type | GWAS trait | Reference |
|---|---|---|---|---|---|---|---|
| G > T_Alt | chr6:32977420 | 1 | rs381218 | AGGGCCATTACACTCTGTGCTTTAATCAAATCAGTTCAGTCCGTTGTGGTGAAGACAGGAACAAGGCGGAGTAAAGAAGAAAACAGATTCGAGGATGGGGCGACCCCTTCTGTCTTCAGCCAATCACAGAAATTCTCTGAGTGAATGTATCTGTTGCTGGGTAAAGAGGGAAAGAGCCGGGGTGAGAAGGTGAAGGATTCACTGGGCCCCCAGGAGAGGCCAG | Non-risk | Predicted causal SNP | Chronic Hep B | This disclosure |
| G > T_Ref | chr6:32977420 | 2 | rs381218 | AGGGCCATTACACTCTGTGCTTTAATCAAATCAGTTCAGTCCGTGTGGTGAAGACAGGAACAAGGCGGAGTAAAGAAGAAAACAGATTCGAGGATGGGGCGACCCCTGCTGTCTTCAGCCAATCACAGAAATTCTCTGAGTGAATGTATCTGTTGCTGGGTAAAGAGGGAAAGAGCCGGGGTGAGAAGGTGAAGGATTCACTGGGCCCCCAGGAGAGGCCAG | Risk | | Chronic Hep B | This disclosure |
| G > A_Alt | chr6:32974934 | 3 | rs378352 | TCCTCCCCCACCCCCAGACTCCCGGGGCCTCTGCACCTGGGGACACTGGACACATATGTGCCCATGATGATGAGGACGGTGCCCACGAGGAAGCCCACCAGGCCGATGGCCAGACCCAGGGCACAGACCAGGGTCTCCATGGCATCTGGTGGTGGAATAGGCACCTGGAGCTCTAGGAGAGAAGGAAGGAGTTGGTGGTATATGAAAGATTCTAGAGTAAAGGAAAC | Non-risk | Reported lead SNP | Chronic Hep B | Jiang et al., 2015 |
| G > A_Ref | chr6:32974934 | 4 | rs378352 | TCCTCCCCCACCCCCAGACTCCCGGGGCCTCTGCACCTGGGGACACTGGACACATATGTGCCCATGATGATGAGGACGGTGCCCACGAGGAAGCCCACCAGGCCGATGGCCAGGCCCAGGGCACAGACCAGGGTCTCCATGGCATCTGGTGGTGGAATAGGCACCTGGAGCTCTAGGAGAGAAAGGAAGGAGTTGGTGGTATATGAAAGATTCTAGAGTAAAGGAAAC | Risk | | Chronic Hep B | Jiang et al., 2015 |
| GTTC > G_Alt | chr3:46249943 | 5 | rs147398495 | TTATGAATTCAAGTTTCAAGATCCTGACCAAGTAGGAGTACTCAGCTTCCTGTGTGATGATGGAGAATTGCTCCAGTTTCACAGTCTTTCAAAATGACAAGAAAGGGACAAAGTTCTTCTTTTTGTGTTTGTGCTCATGAATGGCCACAACGCCCACCAGTGGCCACTTCCTGGAAGCCAAGTTAACTGCCGAGGATTTCTCTGCTCACTCTGAGCCTCTTGAG | Non-risk | Predicted causal SNP | Behcet's disease CCR1 locus | This paper |

TABLE 3-continued

Experimental Validation of Causal Variants

| Insert Name | Coord | Sequence | Seq ID No. | rsID | Allele type | GWAS trait | Reference |
|---|---|---|---|---|---|---|---|
| GTTC > G_Ref | chr3:46249943 | TTATGAATTCAAGTTTGAAGATCCTGACCA AGTAGGAAGTACTGAGCTTCCTGTGAT GATGGAGAATTGGCTCCAGTTCACAGTCT TTCAAAATGACAAGAAAGGGACAAAGTTCT TTTTGTGTGGTTTGGTGCTCATGAATGCC ACAACGCCCACCAGTGGCCACTTCCTGA AGCCAAGTTAACTGCGAGGATTTTCTCTGC TCACTCTGAGCCTCTTGAG | 6 | rs147398495 | Risk | Behcet's disease CCR1 locus | This paper |
| C > T_Alt | chr3:46205686 | GTTTCCCTGGGTCACACATTCACTCACGG CTTCTCTTGGCTGGGAGTGGGGGTTCCCT TGGGTCTGTGTTGCTCCTGGGTGGGCTGA CATCCTGCCCTGCTTTTCTACATTCTCTGT GGGTTGAACAGTTTCTCTGATCAGTCCTAA TGTGAGCACCTGGATGTTTTAGTTGAAGGT GCTGAATTTACTCACCCTTTTGTCCATCT CCGTGAGTGCCACACCCTGTAGC | 7 | rs7616215 | Non-risk | Reported lead SNP | Behcet's disease Kirino at al., 2013 CCR1 locus |
| C > T_Ref | chr3:46205686 | GTTTCCCTGGGTCACACATTCACTCACGG CTTCTCTTGGCTGGGAGTGGGGGTTCCCT TGGGTCTGTGTTGCTCCTGGGTGGGCTGA CATCCTGCCCTGCTTTTCTACATTCTCCGT GGGTTGAACAGTTTCTCTGATCAGTCCTAA TGTGAGCACCTGGATGTTTTAGTTGAAGGT GCTGAATTTACTCACCCTTTTGTCCATCT CCGTGAGTGCCACACCCTGTAGC | 8 | rs7616215 | Risk | | Behcet's disease Kirino at al., 2013 CCR1 locus |
| C > T_Alt | chr5:150226345 | CCTGTGAAACAACGAACCCCCCGGGAGA AACGAACAACTCCAGACTCGCCGCCTGAA GAGCTGTAACTCTCACTTCGAAGGTCTGC AGCTTCGCTCCTGAGTCAGTGAAACCATG AACCCACCGGAAGGAAGAAACTCTGAACA CATCCAAACATCAGAAGGAACAAACTCCG GACACGCAGCCTTTAAGAATTGTAACACTC ACCCGCGAGGGTCCCGTGGCTTCATTCT | 9 | rs11748158 | Non-risk | Predicted causal | Crohn's, etc. This paper |
| C > T_Ref | chr5:150226345 | CCTGTGAAACAACGAACCCCCCGGGAGA AACGAACAACTCCAGACTCGCCGCCTGAA GAGCTGTAACTCTCACTTCGAAGGTCTGC AGCTTCGCTCCTGAGTCAGTGAAACCACG AACCCACCGGAAGGAAGAAACTCTGAACA CATCCAAACATCAGAAGGAACAAACTCCG GACACGCAGCCTTTAAGAATTGTAACACTC ACCCGCGAGGGTCCCGTGGCTTCATTCT | 10 | rs11748158 | Risk | | Crohn's, etc. This paper |
| T > C_Alt | chr5:150223387 | CACAGAAAAGCTGGAAACTATAGGGT TTTCTGCTGACCTCCCACACTCACCATGA | 11 | rs13361189 | Non-risk | Reported lead for IRGM | Crohn's, etc. Parkes et al., 2007 |

TABLE 3-continued

Experimental Validation of Causal Variantts

| Insert Name | Coord | Sequence | Seq ID No. | rsID | Allele type | GWAS trait | Reference |
|---|---|---|---|---|---|---|---|
| | | CAGTCAGTACCCTGCACTGGCCCGTGTCG TACCCAAGCAGAGTGTGCTTGAAAATCGG ATGTATATTAGTAGACCCCGTGCTCAGCG GGTACAGTTTAGAAAGGGAAGTTAACTTAT CTGTCAATTAGTAAGTTAACAACACACAAA GGTACTATGTTTTATTAATCAAA | | | | | |
| T > C_Ref | chr5:150223387 | CACAGAAAAAGCCTGGAAAACTATAGGGT TTTCTGCTGACCTCCCACTCACCATGGA CAGTCAGTACCCTGCACTGGCCCGTGTCG TACCCAAGCAGAGTGTGCTTGAAAATCGG ATGTATATTAGTAGACCCCGTGCTCAGCG GGTACAGTTTAGAAAGGGAAGTTAACTTAT CTGTCAATTAGTAAGTTAACAACACACAAA GGTACTATGTTTTATTAATCAAA | 12 | rs13361189 | Risk | Crohn's, etc. | Parkes et al., 2007 |
| C > T_Alt | chr3:46205686 | GTGGGTGTTTTCTTGGCACTGATGCAACA GTGTTCAAAACTGGACATTCTGAACTTTTG GGGGAATCCTAAATCCTAATAACTCCAATA TACTTGATTGCAATGCCCATGTGTATGCTG TTATTTTGTAATAGTTTACTAAGAAACTTTA CTTCCTGAGCAACCACAGTCCCTGTCCTG GAGCTCATGCCAAAGAGTTAATAATTATGC AGGCACCACAGGAACAAGGTC | 13 | rs1000113 | Non-risk | Reported lead | WTCCC 2007 |
| C > T_Ref | chr3:46205686 | GTGGGTGTTTTCTTGGCACTGATGCAACA GTGTTCAAAACTGGACATTCTGAACTTTTG GGGGAATCCTAAATCCTAATAACTCCAATA TACTTGATTGCAATGCCCATGTGTACGCTG TTATTTTGTAATAGTTTACTAAGAAACTTTA CTTCCTGAGCAACCACAGTCCCTGTCCTG GAGCTCATGCCAAAGAGTTAATAATTATGC AGGCACCACAGGAACAAGGTC | 14 | rs1000113 | Risk | Reported lead | WTCCC 2007 |
| A > G_Alt | chr5:150258867 | GAAGCTTCCAAGGATGTGCAGGTTATCCA AAAATTAATTGCATGCCAGTGTTTATTTTT GTTAAACTGGCTTACTTGCTTCCATCAGAA GTAAGAAATGTAGATGAGGTCTGTGTTACA TAAATGTGCATTGAAACACCAGTGTCAATC AGAAAATTAGAAAAATCTTTGTTTTCAGAT TCTCTTTTGCATTTATTGGTAATTTAAGCACT AAAGAATTATTCATGTGT | 15 | rs111747270 | Non-risk | | Barrett et al., 2008 |
| A > G_Ref | chr5:150258867 | GAAGCTTCCAAGGATGTGCAGGTTATCCA AAAATTAATTGCATGCCAGTGTTTATTTTT GTTAAACTGGCTTACTTGCTTCCATCAGAA GTAAGAAATGTAGATGAGGTCTGTATTACA | 16 | rs111747270 | Risk | Reported lead | Barrett et al., 2008 |

TABLE 3-continued

Experimental Validation of Causal Variants

| Insert Name | Coord | Seq ID No. | rsID | Sequence | Allele type | GWAS trait | Reference |
|---|---|---|---|---|---|---|---|
| A > G_Alt | chr5:150270420 | 17 | rs7714584 | TCCATATATTTGGTATTTTCCACATATTTTC ATGTTATTTATTTCTAATGTAATTGATTTCTA ATGAATTAAATTAGAATCACATGAGAATGA GTCACCTTACCTTTTAAATTTGTTGCTCTGT CTTGGTAAATGCTTGACATGGACTTAAAAA TGTGTATTGTACCATTTTGGGGTGGGATGT TCTACAAATGTCAACTAGGTCAAATTGGTT GATTTGCTGTTCAAG | Non-risk | Crohn's, etc. | Franke at al., 2010 |
| A > G_Ref | chr5:150270420 | 18 | rs7714584 | TCCATATATTTGGTATTTTCCACATATTTTC ATGTTATTTATTTCTAATGTAATTGATTTCTA ATGAATTAAATTAGAATCACATGAGAATGA GTCACCTTACCTTTTAAATTTATTGCTCTGT CTTGGTAAATGCTTCACATGGACTTAAAAA TGTGTATTGTACCATTTTGGGGTGGGATGT TCTACAAATGTCAACTAGGTCAAATTGGTT GATTTGCTGTTCAAG | Risk Reported lead | Crohn's, etc. | Franke et al., 2010 |
| A > G_Alt | chr5:150277909 | 19 | rs11741861 | AAAGAGAAGGTGCAGTTTCAGATGGTCTA CAATAAAGCTGTCCAGTTAGCCCTCAACAA AGGCATAACCTCCATTTGCAAAGGTATGAA GGTCATAAAAGTCATGACATATGTCGGGAA CAATCTAATCACAGCAACTAGTAAGGAAAG GCACTTGATTGGACAACTCTGAGTTATTCA GGGAAGCCATCCTTACCCATTGAGACCAG GTGGCTGTAGTTCTCCAGCATC | Non-risk | Crohn's, etc. | Jostins et al., 2012; Liu et al., 2015 |
| A > G_Ref | chr5:150277909 | 20 | rs11741861 | AAAGAGAAGGTGCAGTTTCAGATGGTCTA CAATAAAGCTGTCCAGTTAGCCCTCAACAA AGGCATAACCTCCATTTGCAAAGGTATGAA GGTCATAAAAGTCATGACATATGTCAGGAA CAATCTAATCACAGCAACTAGTAAGGAAAG GCACTTGATTGGACAACTCTGAGTTATTCA GGGAAGCCATCCTTACCCATTGAGACCAG GTGGCTGTAGTTCTCCAGCATC | Risk Reported lead | Crohn's, etc. | Jostins et al., 2012; Liu et al., 2015 |

*Common 5' Sequence matching plasmid cloning sites: TCGCCGGTACCTGAG (Seq. ID No. 21)
*Common 3' Sequence matching plasmid cloning sites: ATCAAGATCTGGCCT (Seq. ID No. 22)

What is claimed is:

1. A method to perform site-directed mutagenesis on a biological cell, the method comprising:
    obtaining genetic sequence data that includes a nucleotide sequence of a sequence structure of at least one gene;
    determining, utilizing a computational framework, an expression level of the at least one gene,
        wherein the computational framework includes a deep convolutional neural network and a linear regression model,
        wherein the deep convolutional neural network of the computational framework utilizes the genetic sequence data to determine epigenetic regulatory features along a genetic sequence that includes the nucleotide sequence of the sequence structure of the at least one gene,
        wherein the linear regression model of the computational framework determines the expression level of the at least one gene based on the epigenetic regulatory features along the genetic sequence that includes the nucleotide sequence of the sequence structure of the at least one gene sequence;
    identifying, utilizing the computational framework, a set of one or more genetic variants within the genetic sequence data that includes the nucleotide sequence of the sequence structure of the at least one gene, wherein the set of one or more genetic variants alter the expression level of the at least one gene as determined by an effect of the set of one or more genetic variants on the epigenetic regulatory features along the genetic sequence that includes the nucleotide sequence of the sequence structure of at least one gene sequence; and
    based on the identification of the set of variants that alter the expression level of the at least one gene, performing site-directed mutagenesis on DNA of a biological cell to introduce the identified genetic set of variants within a corresponding genetic sequence of the DNA that includes a corresponding nucleotide sequence of the sequence structure of the at least one gene such that the expression level of the at least one gene is altered in the biological cell.

2. The method of claim 1, wherein the genetic sequence data has been obtained by: extracting and sequencing DNA from a biological sample or obtaining the genetic sequence data from a database.

3. The method of claim 1, wherein the epigenetic regulatory features include at least one of: sites of chromatin accessibility, chromatin marks, and transcription factor binding sites.

4. The method of claim 1, wherein the deep convolutional neural network is trained on epigenetic regulatory data acquired by at least one epigenetic assay.

5. The method of claim 4, wherein the epigenetic is assay is one of: chromatin immunoprecipitation sequencing (ChIP-seq), DNAse I hypersensitivity sequencing (DNase-seq), Assay for Transposase-Accessible Chromatin sequencing (ATAC-seq), Formaldehyde-Assisted Isolation of Regulatory Elements (FAIRE-seq), Hi-C capture sequencing, bisulfite sequencing (BS-seq), or methyl array.

6. The method of claim 1, wherein the deep convolutional neural network determines the epigenetic regulatory features spatially along the genetic sequence that includes the nucleotide sequence of the sequence structure of the at least one gene sequence by considering single nucleotide variants, insertions, and deletions within the genetic sequence that includes the nucleotide sequence of the sequence structure of the at least one gene sequence.

7. The method of claim 1, wherein the computational framework is trained for a particular cell-type or tissue, wherein the biological cell is of the particular cell-type or tissue.

8. The method of claim 1, wherein the computational framework determines the epigenetic regulatory features spatially along the genetic sequence for all Poll II transcribed genes of an organismal genome.

9. The method of claim 1, wherein the sequence structure is a transcription start site or promoter sequence of the at least one gene.

10. The method of claim 1, wherein the genetic sequence that includes the nucleotide sequence of the sequence structure of the at least one gene further includes nucleotide sequence 1 kb upstream of the gene sequence structure or 1 kb downstream of the gene sequence structure.

11. The method of claim 1, wherein the computational framework determines the epigenetic regulatory features spatially along the genetic sequence in sequence bins, wherein the sequence bins are 50 bp, 100 bp, 150 bp, 200 bp, 250 bp, 300 bp, 400 bp, or 500 bp in length.

12. The method of claim 11, wherein the computational framework considers the surrounding sequence context to determine the epigenetic regulatory features for each sequence bin.

13. The method of claim 1, wherein the computational framework spatially transforms the epigenetic regulatory features that are determined from the sequence data, wherein spatially transforming the epigenetic regulatory features reduces the number of epigenetic regulatory features that are used to determine the expression level of the at least one gene.

14. The method of claim 1, wherein the linear regression model is L2 regularized.

15. The method of claim 1, wherein the site-directed mutagenesis is performed by one of: CRISPR mutagenesis, Zinc-finger mutagenesis, or TALEN mutagenesis.

16. The method as in claim 1, wherein the genetic sequence data is derived from a biological sample having the identified genetic set of variants, and wherein the biological sample is derived from an individual having a medical disorder.

17. The method of claim 1, wherein the identified genetic set of variants that alter the expression level of the at least one gene are hypothetical variants that are not present in the genetic sequence and not present in the biological cell prior to performing the site-directed mutagenesis.

\* \* \* \* \*

SEQUENCE LISTING

<160> NUMBER OF SEQ ID NOS: 22

<210> SEQ ID NO 1
<211> LENGTH: 230
<212> TYPE: DNA
<213> ORGANISM: Homo sapiens

<400> SEQUENCE: 1
agggccatta cactctggtg ctttaatcaa atcagtctca gtccgtgtgg tgaggacagg      60
aacaaggcgg aggtaaagaa gaagaaaaca gattcgagga tgggggcgac cccttctgtc     120
ttcagccaat cacagaaatt ctctgagtga atgtatctgt tgctgggtaa agagggaaag    180
agccggggtg agaaggtgga aggattcact gggcccccag gagaggccag                230

<210> SEQ ID NO 2
<211> LENGTH: 230
<212> TYPE: DNA
<213> ORGANISM: Homo sapiens

<400> SEQUENCE: 2
agggccatta cactctggtg ctttaatcaa atcagtctca gtccgtgtgg tgaggacagg      60
aacaaggcgg aggtaaagaa gaagaaaaca gattcgagga tgggggcgac ccctgctgtc    120
ttcagccaat cacagaaatt ctctgagtga atgtatctgt tgctgggtaa agagggaaag    180
agccggggtg agaaggtgga aggattcact gggcccccag gagaggccag                230

<210> SEQ ID NO 3
<211> LENGTH: 230
<212> TYPE: DNA
<213> ORGANISM: Homo sapiens

<400> SEQUENCE: 3
tcctccccca cccccagac tcccggggcc tctgcacctg ggacactgg acacatatgt        60 gcccatgatg atgaggacgg tgcccacgag gaagcccacc aggccgatgg ccagacccag    120
ggcacagacc agggtctcca tggcatctgg tggtggaata ggcacctgga gctctaggag    180
agaaaggaag gagttggtgg tatatgaaag gattctagag taaaggaaac                230

<210> SEQ ID NO 4
<211> LENGTH: 230
<212> TYPE: DNA
<213> ORGANISM: Homo sapiens

<400> SEQUENCE: 4
tcctccccca cccccagac tcccggggcc tctgcacctg ggacactgg acacatatgt        60 gcccatgatg atgaggacgg tgcccacgag gaagcccacc aggccgatgg ccaggcccag    120
ggcacagacc agggtctcca tggcatctgg tggtggaata ggcacctgga gctctaggag    180
agaaaggaag gagttggtgg tatatgaaag gattctagag taaaggaaac                230

<210> SEQ ID NO 5
<211> LENGTH: 230
<212> TYPE: DNA
<213> ORGANISM: Homo sapiens

<400> SEQUENCE: 5
ttatgaattc aagtttcaag atcctgacca agtaggaagt actcagcttc ctgtgtgatg      60
atggagaatt ggctccagtt tcacagtctt tcaaaatgac aagaaaggga caaagttctt    120 cttttttgtgt ggtttggtgc tcatgaatgg ccacaacgcc caccagtggc cacttcctgg    180
aagccaagtt aactgcgagg attttctctg ctcactctga gcctcttgag        230

<210> SEQ ID NO 6
<211> LENGTH: 227
<212> TYPE: DNA
<213> ORGANISM: Homo sapiens

<400> SEQUENCE: 6
ttatgaattc aagtttcaag atcctgacca agtaggaagt actcagcttc ctgtgtgatg        60
atggagaatt ggctccagtt tcacagtctt tcaaaatgac aagaaaggga caaagttctt        120
tttgtgtggt ttggtgctca tgaatggcca caacgcccac cagtggccac ttcctggaag        180
ccaagttaac tgcgaggatt ttctctgctc actctgagcc tcttgag                      227

<210> SEQ ID NO 7
<211> LENGTH: 230
<212> TYPE: DNA
<213> ORGANISM: Homo sapiens

<400> SEQUENCE: 7
gtttccctgg gtcacacatt cactcacggc ttctcttggc tgggagtggg ggttcccttg        60
ggtctgtgtt gctcctgggt gggctgacat cctgccctgc ttttctacat tctctgtggg        120
ttgaacagtt tctctgatca gtcctaatgt gagcacctgg atgttttagt tgaaggtgct        180
gaatttactc accccttttg tccatctccg tgagtgccac accctgtagc                   230

<210> SEQ ID NO 8
<211> LENGTH: 230
<212> TYPE: DNA
<213> ORGANISM: Homo sapiens

<400> SEQUENCE: 8
gtttccctgg gtcacacatt cactcacggc ttctcttggc tgggagtggg ggttcccttg        60
ggtctgtgtt gctcctgggt gggctgacat cctgccctgc ttttctacat tctccgtggg        120
ttgaacagtt tctctgatca gtcctaatgt gagcacctgg atgttttagt tgaaggtgct        180
gaatttactc accccttttg tccatctccg tgagtgccac accctgtagc                   230

<210> SEQ ID NO 9
<211> LENGTH: 230
<212> TYPE: DNA
<213> ORGANISM: Homo sapiens

<400> SEQUENCE: 9
cctgtgaaac aacgaacccc ccggggagaa acgaacaact ccagactcgc cgcctgaaga        60
gctgtaactc tcacttcgaa ggtctgcagc ttcgctcctg agtcagtgaa accatgaacc        120
caccggaagg aagaaactct gaacacatcc aaacatcaga aggaacaaac tccggacacg        180
cagcctttaa gaattgtaac actcaccgcg agggtccgtg gcttcattct                   230

<210> SEQ ID NO 10
<211> LENGTH: 230
<212> TYPE: DNA
<213> ORGANISM: Homo sapiens

<400> SEQUENCE: 10
cctgtgaaac aacgaacccc ccggggagaa acgaacaact ccagactcgc cgcctgaaga        60
gctgtaactc tcacttcgaa ggtctgcagc ttcgctcctg agtcagtgaa accacgaacc        120

| | |
|---|---|
| caccggaagg aagaaactct gaacacatcc aaacatcaga aggaacaaac tccggacacg | 180 |
| cagcctttaa gaattgtaac actcaccgcg agggtccgtg gcttcattct | 230 |

<210> SEQ ID NO 11
<211> LENGTH: 230
<212> TYPE: DNA
<213> ORGANISM: Homo sapiens

<400> SEQUENCE: 11

| | |
|---|---|
| cacagaaaaa gcctggaaaa ctatagggtt ttctgctgac ctcccacact caccatggac | 60 |
| agtcagtacc ctgcactggc ccgtgtcgta cccaagcaga gtgtgcttga aaatcggatg | 120 |
| tatattagta gaccccgtgc tcagcgggta cagtttagaa agggaagtta acttatctgt | 180 |
| caattagtaa gttaacaaca cacaaagtgt actatgtttt attaatcaaa | 230 |

<210> SEQ ID NO 12
<211> LENGTH: 230
<212> TYPE: DNA
<213> ORGANISM: Homo sapiens

<400> SEQUENCE: 12

| | |
|---|---|
| cacagaaaaa gcctggaaaa ctatagggtt ttctgctgac ctcccacact caccatggac | 60 |
| agtcagtacc ctgcactggc ccgtgtcgta cccaagcaga gtgtgcttga aaattggatg | 120 |
| tatattagta gaccccgtgc tcagcgggta cagtttagaa agggaagtta acttatctgt | 180 |
| caattagtaa gttaacaaca cacaaagtgt actatgtttt attaatcaaa | 230 |

<210> SEQ ID NO 13
<211> LENGTH: 230
<212> TYPE: DNA
<213> ORGANISM: Homo sapiens

<400> SEQUENCE: 13

| | |
|---|---|
| gtgggtgttt tcttggcact gatgcaacag tgttcaaaac tggacattct gaacttttgg | 60 |
| gggaatccta atcctaata actccaatat acttgattgc aatgcccatg tgtatgctgt | 120 |
| tattttgtaa tagtttacta agaaacttta cttcctgagc aaccacagtc cctgtcctgg | 180 |
| agctcatgcc aaagagttaa taattatgca ggcaccacag gaacaaggtc | 230 |

<210> SEQ ID NO 14
<211> LENGTH: 230
<212> TYPE: DNA
<213> ORGANISM: Homo sapiens

<400> SEQUENCE: 14

| | |
|---|---|
| gtgggtgttt tcttggcact gatgcaacag tgttcaaaac tggacattct gaacttttgg | 60 |
| gggaatccta atcctaata actccaatat acttgattgc aatgcccatg tgtacgctgt | 120 |
| tattttgtaa tagtttacta agaaacttta cttcctgagc aaccacagtc cctgtcctgg | 180 |
| agctcatgcc aaagagttaa taattatgca ggcaccacag gaacaaggtc | 230 |

<210> SEQ ID NO 15
<211> LENGTH: 230
<212> TYPE: DNA
<213> ORGANISM: Homo sapiens

<400> SEQUENCE: 15

| | |
|---|---|
| gaagcttcca aggatgtgca ggttatccaa aaatttaatt gcatgccagt gtttattttt | 60 |
| gttaaactgg cttacttgct tccatcagaa gtaagaaatg tagatgaggt ctgtgttaca | 120 |

| | |
|---|---|
| taaatgtgca ttgaaacacc agtgtcaatc agaaaaatta gaaaaatctt tgttttcaga | 180 |
| ttctctttgc atttattggt aatttaagca ctaagaatt attcatgtgt | 230 |

<210> SEQ ID NO 16
<211> LENGTH: 230
<212> TYPE: DNA
<213> ORGANISM: Homo sapiens

<400> SEQUENCE: 16

| | |
|---|---|
| gaagcttcca aggatgtgca ggttatccaa aaatttaatt gcatgccagt gtttattttt | 60 |
| gttaaactgg cttacttgct tccatcagaa gtaagaaatg tagatgaggt ctgtattaca | 120 |
| taaatgtgca ttgaaacacc agtgtcaatc agaaaaatta gaaaaatctt tgttttcaga | 180 |
| ttctctttgc atttattggt aatttaagca ctaaagaatt attcatgtgt | 230 |

<210> SEQ ID NO 17
<211> LENGTH: 230
<212> TYPE: DNA
<213> ORGANISM: Homo sapiens

<400> SEQUENCE: 17

| | |
|---|---|
| tccatatatt tggtattttc cacatatttt catgttattt atttctaatg taattgattt | 60 |
| ctaatgaatt aaattagaat cacatgagaa tgagtcacct tacctttaa atttgttgct | 120 |
| ctgtcttggt aaatgcttca catggactta aaaatgtgta ttgtaccatt ttggggtggg | 180 |
| atgttctaca aatgtcaact aggtcaaatt ggttgatttt gctgttcaag | 230 |

<210> SEQ ID NO 18
<211> LENGTH: 230
<212> TYPE: DNA
<213> ORGANISM: Homo sapiens

<400> SEQUENCE: 18

| | |
|---|---|
| tccatatatt tggtattttc cacatatttt catgttattt atttctaatg taattgattt | 60 |
| ctaatgaatt aaattagaat cacatgagaa tgagtcacct tacctttaa atttattgct | 120 |
| ctgtcttggt aaatgcttca catggactta aaaatgtgta ttgtaccatt ttggggtggg | 180 |
| atgttctaca aatgtcaact aggtcaaatt ggttgatttt gctgttcaag | 230 |

<210> SEQ ID NO 19
<211> LENGTH: 230
<212> TYPE: DNA
<213> ORGANISM: Homo sapiens

<400> SEQUENCE: 19

| | |
|---|---|
| aaagagaagg tgcagtttca gatggtctac aataaagctg tccagttagc cctcaacaaa | 60 |
| ggcataacct ccatttgcaa aggtatgaag gtcataaaag tcatgacata tgtcgggaac | 120 |
| aatctaatca cagcaactag taaggaaagg cacttgattg acaactctg agttattcag | 180 |
| ggaagccatc cttacccatt gagaccaggt ggctgtagtt ctccagcatc | 230 |

<210> SEQ ID NO 20
<211> LENGTH: 230
<212> TYPE: DNA
<213> ORGANISM: Homo sapiens -continued

```
<400> SEQUENCE: 20
aaagagaagg tgcagtttca gatggtctac aataaagctg tccagttagc cctcaacaaa      60
ggcataacct ccatttgcaa aggtatgaag gtcataaaag tcatgacata tgtcaggaac     120
aatctaatca cagcaactag taaggaaagg cacttgattg gacaactctg agttattcag     180
ggaagccatc cttacccatt gagaccaggt ggctgtagtt ctccagcatc                230

<210> SEQ ID NO 21
<211> LENGTH: 15
<212> TYPE: DNA
<213> ORGANISM: Artificial Sequence
<220> FEATURE:
<223> OTHER INFORMATION: Cloning Site

<400> SEQUENCE: 21
tggccggtac ctgag                                                       15

<210> SEQ ID NO 22
<211> LENGTH: 15
<212> TYPE: DNA
<213> ORGANISM: Artificial Sequence
<220> FEATURE:
<223> OTHER INFORMATION: Cloning site

<400> SEQUENCE: 22
atcaagatct ggcct                                                       15
```